US009453996B2

(12) United States Patent
Delahunt et al.

(10) Patent No.: US 9,453,996 B2
(45) Date of Patent: Sep. 27, 2016

(54) DEVICES AND METHODS FOR STAINING AND MICROSCOPY

(71) Applicant: Tokitae LLC, Bellevue, WA (US)

(72) Inventors: Charles Delahunt, Seattle, WA (US); David Gasperino, Lake Forest Park, WA (US); Matthew P. Horning, Kirkland, WA (US); Kevin P. F. Nichols, Seattle, WA (US); Benjamin K. Wilson, Kirkland, WA (US)

(73) Assignee: Tokitae LLC, Bellevue, WA (US)

( * ) Notice: Subject to any disclaimer, the term of this patent is extended or adjusted under 35 U.S.C. 154(b) by 149 days.

(21) Appl. No.: 14/061,009

(22) Filed: Oct. 23, 2013

(65) Prior Publication Data

US 2015/0111216 A1 Apr. 23, 2015

(51) Int. Cl.
| | | |
|---|---|---|
| *G02B 21/34* | (2006.01) | |
| *B01L 3/00* | (2006.01) | |
| *G01N 1/31* | (2006.01) | |
| *B01L 9/00* | (2006.01) | |

(52) U.S. Cl.
CPC .......... *G02B 21/34* (2013.01); *B01L 3/5023* (2013.01); *B01L 3/50273* (2013.01); *B01L 9/527* (2013.01); *B01L 2300/0816* (2013.01); *B01L 2300/0822* (2013.01); *B01L 2400/0406* (2013.01); *C12Q 2563/107* (2013.01); *G01N 1/312* (2013.01)

(58) Field of Classification Search
CPC .............................. G01N 1/312; B01L 9/527
USPC .................................................. 422/502, 563
See application file for complete search history.

(56) References Cited

U.S. PATENT DOCUMENTS

| | | | |
|---|---|---|---|
| 4,171,866 | A | 10/1979 | Tolles |
| 5,021,294 | A | 6/1991 | Karasawa et al. |
| 5,376,337 | A | 12/1994 | Seymour |
| 5,700,559 | A | 12/1997 | Sheu et al. |
| 6,551,554 | B1 | 4/2003 | Vermeiden et al. |
| 6,555,361 | B1 | 4/2003 | Lyman et al. |

(Continued)

FOREIGN PATENT DOCUMENTS

| | | |
|---|---|---|
| EP | 0215419 B1 | 5/1991 |
| EP | 2 559 806 A1 | 2/2013 |

(Continued)

OTHER PUBLICATIONS

PCT International Search Report; International App. No. PCT/US2014/061742; Feb. 10, 2015; pp. 1-4.

(Continued)

*Primary Examiner* — Lyle Alexander
*Assistant Examiner* — Bryan Kilpatrick

(57) ABSTRACT

Devices and methods for preparing and assessing a liquid sample are described which include: a microfluidic microscopy device including an absorbent structure including at least one dry dye for a liquid and configured to convey a polar liquid from a first end of the absorbent structure through the at least one dry dye for a liquid to a second end of the absorbent structure, a support structure positioned adjacent to a first surface of the absorbent structure, a lid structure positioned adjacent to a second surface of the absorbent structure, and a clamping structure positioned to maintain a relative position of the support structure and the lid structure to form a tapered internal chamber adjacent to the second end of the absorbent structure.

16 Claims, 14 Drawing Sheets

(56) References Cited

U.S. PATENT DOCUMENTS

| | | | |
|---|---|---|---|
| 6,911,535 | B2 | 6/2005 | Schwartz |
| 7,282,241 | B2 | 10/2007 | Kim et al. |
| 7,867,756 | B2 * | 1/2011 | Hirao et al. .......... B01L 3/5023 435/287.1 |
| 2002/0192701 | A1 | 12/2002 | Adey |
| 2004/0266024 | A1 * | 12/2004 | Saito et al. ................... 436/514 |
| 2012/0097272 | A1 | 4/2012 | Vulto et al. |
| 2012/0225446 | A1 | 9/2012 | Wimberger-Friedl et al. |
| 2012/0230891 | A1 | 9/2012 | Meathrel et al. |

FOREIGN PATENT DOCUMENTS

| | | |
|---|---|---|
| JP | 2003-529768 A | 10/2003 |
| WO | WO 00/22409 | 4/2000 |
| WO | WO 2010/008524 A1 | 1/2010 |

OTHER PUBLICATIONS

Al-Tamimi et al.; "Validation of Paper-Based Assay for Rapid Blood Typing"; Analytical Chemistry; Dec. 12, 2011; pp. 1661-1668; vol. 84; American Chemical Society.

Bishara et al.; "Handheld, lensless microscope identifies malaria parasites"; SPIE Newsroom; 2011; pp. 1-3; SPIE.

"Clinical laboratory News: μPADs(Microfluidic Paper-based Analytical Devices)"; Jul. 22, 2013; pp. 1-5; labweekly.blogspot.in/2012/07/pads.html.

Douglas-Hamilton et al.; "Particle Distribution in Low-Volume Capillary-Loaded Chambers"; Journal of Andrology; Jan./Feb. 2005; p. 107-114; vol. 26; No. 1; American Society of Andrology.

Flynn et al.; "Control of Pore Structure Formation in Cellulose Nitrate Polymer Membranes"; Advances in Chemical Science; Jun. 2013; pp. 9-18; vol. 2; Issue 2; www.seipub.org/acs.

Fridley et al.; "Controlled release of dry reagents in porous media for tunable temporal and spatial distribution upon rehydration"; Lab Chip; 2012; pp. 4321-4327; vol. 12; The Royal Society of Chemistry.

Guy et al.; "The use of fluorescence enhancement to improve the microscopic diagnosis of falciparum malaria"; Malaria Journal; Jul. 6, 2007; pp. 1-8; vol. 6; No. 89; BioMed Central Ltd.

Herricks et al.; "Deformability limits of Plasmodium falciparum-infected red blood cells"; Cellular Microbiology; 2009; pp. 1340-1353; vol. 11; No. 9.

Hou et al.; "Deformability based cell margination—A simple microfluidic design for malaria-infected erythrocyte separation"; Lab on a Chip; 2010; pp. 2605-2613; vol. 10; The Royal Society of Chemistry.

Isikman et al.; "Field-portable lensfree tomographic microscope"; Lab on a Chip; Jul. 7, 2011; pp. 2222-2230; vol. 11; No. 13; The Royal Society of Chemistry.

Jahanshahi-Anbuhi et al.; "Creating fast flow channels in paper fluidic devices to control timing of sequential reactions"; Lab on a Chip; 2012; pp. 5079-5085; vol. 12; The Royal Society of Chemistry.

Jouin et al.; "Double Staining of Plasmodium falciparum Nucleic Acids With Hydroethidine and Thiazole Orange for Cell Cycle Stage Analysis by Flow Cytometry"; Cytometry Part A; 2004; pp. 34-38; vol. 57A; Wiley-Liss, Inc.

Kachouie et al.; "Arraycount, an algorithm for automatic cell counting in microwell arrays"; Biotechniques; Sep. 2009; pp. x-xvi; vol. 47, No. 3; NIH-PA Author Manuscript.

Li et al.; "A perspective on paper-based microfluidics: Current status and future trends"; Biomicrofluidics; 2012; pp. 011301-1-0011309-13; vol. 6; American Institute of Physics.

Moody, Anthony; "Rapid Diagnostic Tests for Malaria Parasites"; Clinical Microbiology Reviews; Jan. 2002; pp. 66-78; vol. 15; No. 1; American Society for Microbiology.

Rossi et al.; "Tapered microfluidic chip for the study of biochemical and mechanical response at subcellular level of endothelial cells to shear flow"; Lab on a Chip; 2009; pp. 1403-1411; vol. 9; The Royal Society of Chemistry.

Vink et al.; "An automatic vision-based malaria diagnosis system"; Journal of Microscopy; 2013; pp. 1-13; The Authors Journal of Microscopy et al.

Vulto et al.; "Phaseguides: a paradigm shift in microfluidic priming and emptying"; Lab on a Chip; 2011; 8 pages; The Royal Society of Chemistry.

Washburn, Edward W.; "The Dynamics of Capillary Flow"; The Physical Review; Mar. 1921; pp. 273-283; vol. XVII; No. 3; Second Series.

Wei et al.; "Fluorescent Imaging of Single Nanoparticles and Viruses on a Smart Phone"; ACS Nano; 2013; pp. A-I; vol. XXX; No. XX; American Chemical Society.

Yetisen et al.; "Paper-based microfluidic point-of-care diagnostic devices"; Lab on a Chip; 2013; pp. 2210-2251; vol. 13; The Royal Society of Chemistry.

* cited by examiner

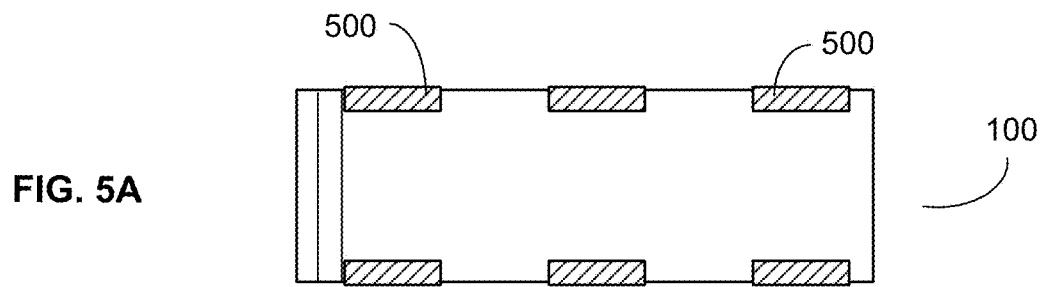
FIG. 5A
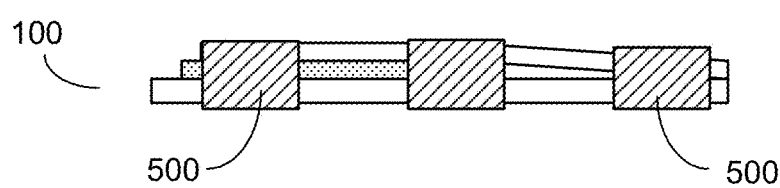
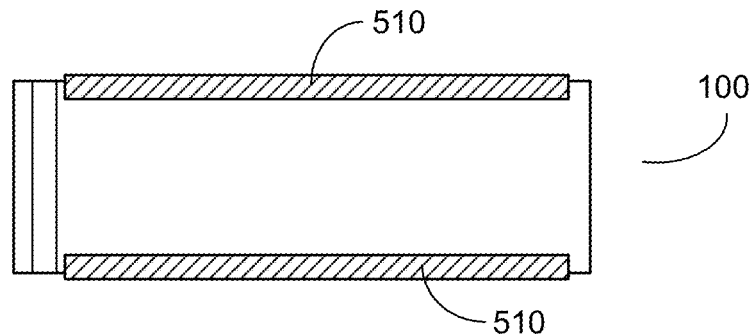
FIG. 5B
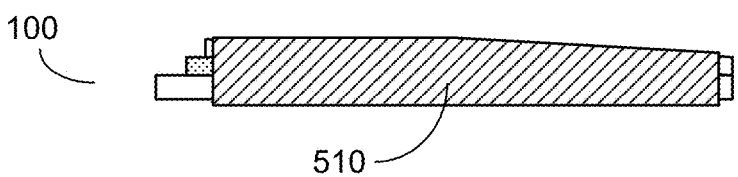
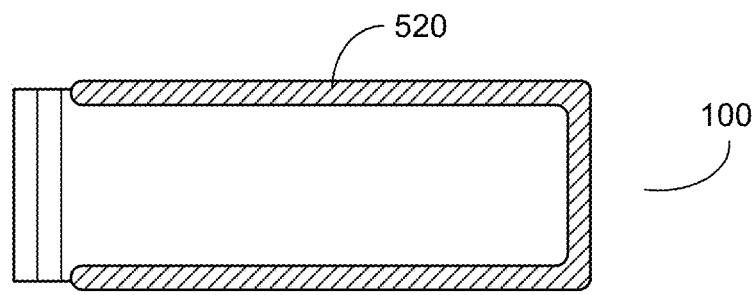
FIG. 5C
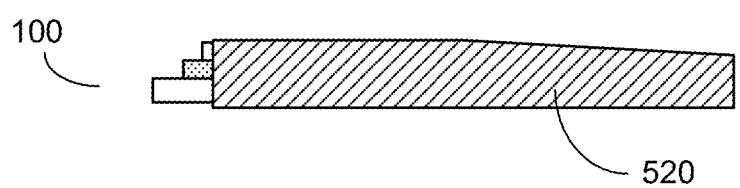

FIG. 17

1700
Receiving a liquid sample at a first end of a microfluidics microscopy device, the microfluidics microscopy device including
- an absorbent structure with a first end and a second end, the absorbent structure including an interior hydrophilic region with at least one dry dye for a liquid;
- a support structure positioned adjacent to a first surface of the absorbent structure, the support structure including a first end and a second end, the second end of the support structure including a second end region positioned adjacent to the second end of the absorbent structure;
- a lid structure positioned adjacent to a second surface of the absorbent structure, the lid structure including a first end and a second end, the second end of the lid structure projecting beyond the second end of the absorbent structure, the second end of the lid structure including a second end region positioned adjacent to the second end of the absorbent structure and overlapping with the second end region of the support structure; and
- a clamping structure positioned to maintain a relative position of the support structure and the lid structure to form a tapered internal chamber adjacent to the second end of the absorbent structure, the tapered internal chamber including an internal surface of the second end region of the support structure facing an internal surface of the second end region of the lid structure, the tapered internal chamber including an outflow region.

1710
Migrating the liquid sample from the first end of the absorbent structure to the second end of the absorbent structure through the interior hydrophilic region including the at least one dry dye for a liquid

1720
Dissolving the at least one dry dye for a liquid in the liquid sample while migrating the liquid sample through the interior hydrophilic region

1730
Migrating the liquid sample with the dissolved at least one dry dye for a liquid from the second end of the absorbent structure into the tapered internal chamber

1740
Filling the tapered internal chamber with the liquid sample with the dissolved at least one dry dye while pushing air out of the tapered internal chamber through the outflow region

FIG. 18

| 1800
Providing an optical detector |

| 1810
Using the optical detector to measure an optical property of a liquid sample in a tapered internal chamber of a microfluidic microscopy device, the microfluidic microscopy device including
    an absorbent structure with a first end and a second end, the absorbent structure including an interior hydrophilic region with at least one dry dye for a liquid, the absorbent structure configured to convey a polar liquid from the first end of the absorbent structure through the interior hydrophilic region and the at least one dry dye for a liquid to the second end of the absorbent structure;
    a support structure positioned adjacent to a first surface of the absorbent structure, the support structure including a first end and a second end, the second end of the support structure including a second end region positioned adjacent to the second end of the absorbent structure;
    a lid structure positioned adjacent to a second surface of the absorbent structure, the lid structure including a first end and a second end, the second end of the lid structure projecting beyond the second end of the absorbent structure, the second end of the lid structure including a second end region positioned adjacent to the second end of the absorbent structure and overlapping with the second end region of the support structure; and
    a clamping structure positioned to maintain a relative position of the support structure and the lid structure to form the tapered internal chamber adjacent to the second end of the absorbent structure, the tapered internal chamber including an internal surface of the second end region of the support structure facing an internal surface of the second end region of the lid structure, the tapered internal chamber including an outflow region. |

DEVICES AND METHODS FOR STAINING AND MICROSCOPY

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None

RELATED APPLICATIONS

None

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

In an aspect, a microfluidic microscopy device includes, but is not limited to, an absorbent structure with a first end and a second end, the absorbent structure including an interior hydrophilic region, the absorbent structure configured to convey a polar liquid from the first end of the absorbent structure through the interior hydrophilic region to the second end of the absorbent structure; a support structure positioned adjacent to a first surface of the absorbent structure, the support structure including a first end and a second end, the second end of the support structure including a second end region positioned adjacent to the second end of the absorbent structure; a lid structure positioned adjacent to a second surface of the absorbent structure, the lid structure including a first end and a second end, the second end of the lid structure including a second end region positioned adjacent to the second end of the absorbent structure and overlapping with the second end region of the support structure; and a clamping structure positioned to maintain a relative position of the support structure and the lid structure to form a tapered internal chamber adjacent to the second end of the absorbent structure, the tapered internal chamber including an internal surface of the second end region of the support structure facing an internal surface of the second end region of the lid structure, the tapered internal chamber including an outflow region. In addition to the foregoing, other device aspects are described in the claims, drawings, and text forming a part of the present disclosure.

In an aspect, a microfluidic microscopy device includes, but is not limited to, an absorbent structure with a first end and a second end, the absorbent structure including an interior hydrophilic region with at least one dry dye for a liquid, the absorbent structure configured to convey a polar liquid from the first end of the absorbent structure through the interior hydrophilic region and the at least one dry dye for a liquid to the second end of the absorbent structure; a support structure positioned adjacent to a first surface of the absorbent structure, the support structure including a first end and a second end, the second end of the support structure including a second end region positioned adjacent to the second end of the absorbent structure; a lid structure positioned adjacent to a second surface of the absorbent structure, the lid structure including a first end and a second end, the second end of the lid structure projecting beyond the second end of the absorbent structure, the second end of the lid structure including a second end region positioned adjacent to the second end of the absorbent structure and overlapping with the second end region of the support structure; a clamping structure positioned to maintain a relative position of the support structure and the lid structure to form a tapered internal chamber adjacent to the second end of the absorbent structure, the tapered internal chamber including an internal surface of the second end region of the support structure facing an internal surface of the second end region of the lid structure; and an interior hydrophobic region positioned adjacent to the interior hydrophilic region of the absorbent structure, a first end of the interior hydrophobic region extending beyond the first end of the lid structure and open to a position adjacent to the device and a second end of the interior hydrophobic region positioned adjacent to the tapered internal chamber. In addition to the foregoing, other device aspects are described in the claims, drawings, and text forming a part of the present disclosure.

In an aspect, a method for processing a liquid sample with a microfluidic microscopy device includes, but is not limited to, receiving a liquid sample at a first end of a microfluidic microscopy device, the microfluidic microscopy device including an absorbent structure with a first end and a second end, the absorbent structure including an interior hydrophilic region with at least one dry dye for a liquid; a support structure positioned adjacent to a first surface of the absorbent structure, the support structure including a first end and a second end, the second end of the support structure including a second end region positioned adjacent to the second end of the absorbent structure; a lid structure positioned adjacent to a second surface of the absorbent structure, the lid structure including a first end and a second end, the second end of the lid structure projecting beyond the second end of the absorbent structure, the second end of the lid structure including a second end region positioned adjacent to the second end of the absorbent structure and overlapping with the second end region of the support structure; and a clamping structure positioned to maintain a relative position of the support structure and the lid structure to form a tapered internal chamber adjacent to the second end of the absorbent structure, the tapered internal chamber including an internal surface of the second end region of the support structure facing an internal surface of the second end region of the lid structure, the tapered internal chamber including an outflow region; migrating the liquid sample from the first end of the absorbent structure to the second end of the absorbent structure through the interior hydrophilic region including the at least one dry dye for a liquid; dissolving the at least one dry dye for a liquid in the liquid sample while migrating the liquid sample through the interior hydrophilic region; migrating the liquid sample with the dissolved at least one dry dye for a liquid from the second end of the absorbent structure into the tapered internal chamber; and filling the tapered internal chamber with the liquid sample with the dissolved at least one dry dye for a liquid while pushing air out of the tapered internal chamber through the outflow region. In addition to the foregoing, other method aspects are described in the claims, drawings, and text forming a part of the present disclosure.

In an aspect, a method for analyzing a liquid sample in a tapered internal chamber of a microfluidic microscopy device includes, but is not limited to, providing an optical detector; and using the optical detector to measure an optical property of a liquid sample in a tapered internal chamber of a microfluidic microscopy device, the microfluidic microscopy device including an absorbent structure with a first end and a second end, the absorbent structure including an interior hydrophilic region with at least one dry dye for a liquid, the absorbent structure configured to convey a polar liquid from the first end of the absorbent structure through the interior hydrophilic region and the at least one dry dye for a liquid to the second end of the absorbent structure; a support structure positioned adjacent to a first surface of the absorbent structure, the support structure including a first end and a second end, the second end of the support structure including a second end region positioned adjacent to the second end of the absorbent structure; a lid structure positioned adjacent to a second surface of the absorbent structure, the lid structure including a first end and a second end, the second end of the lid structure projecting beyond the second end of the absorbent structure, the second end of the lid structure including a second end region positioned adjacent to the second end of the absorbent structure and overlapping with the second end region of the support structure; and a clamping structure positioned to maintain a relative position of the support structure and the lid structure to form the tapered internal chamber adjacent to the second end of the absorbent structure, the tapered internal chamber including an internal surface of the second end region of the support structure facing an internal surface of the second end region of the lid structure, the tampered internal chamber including an outflow region. In addition to the foregoing, other method aspects are described in the claims, drawings, and text forming a part of the present disclosure.

BRIEF DESCRIPTION OF THE FIGURES

FIG. 5A is a schematic of a top view and a side view of an embodiment of clamping structure for a microfluidic microscopy device.

FIG. 5B is a schematic of a top view and a side view of an embodiment of clamping structure for a microfluidic microscopy device.

FIG. 5C is a schematic of a top view and a side view of an embodiment of clamping structure for a microfluidic microscopy device.

FIG. 17 is a flow diagram of a method for processing a liquid in a microfluidic microscopy device.

FIG. 18 is a flow diagram of a method of analyzing a liquid sample with a microfluidic microscopy device.

DETAILED DESCRIPTION

Figure 1:
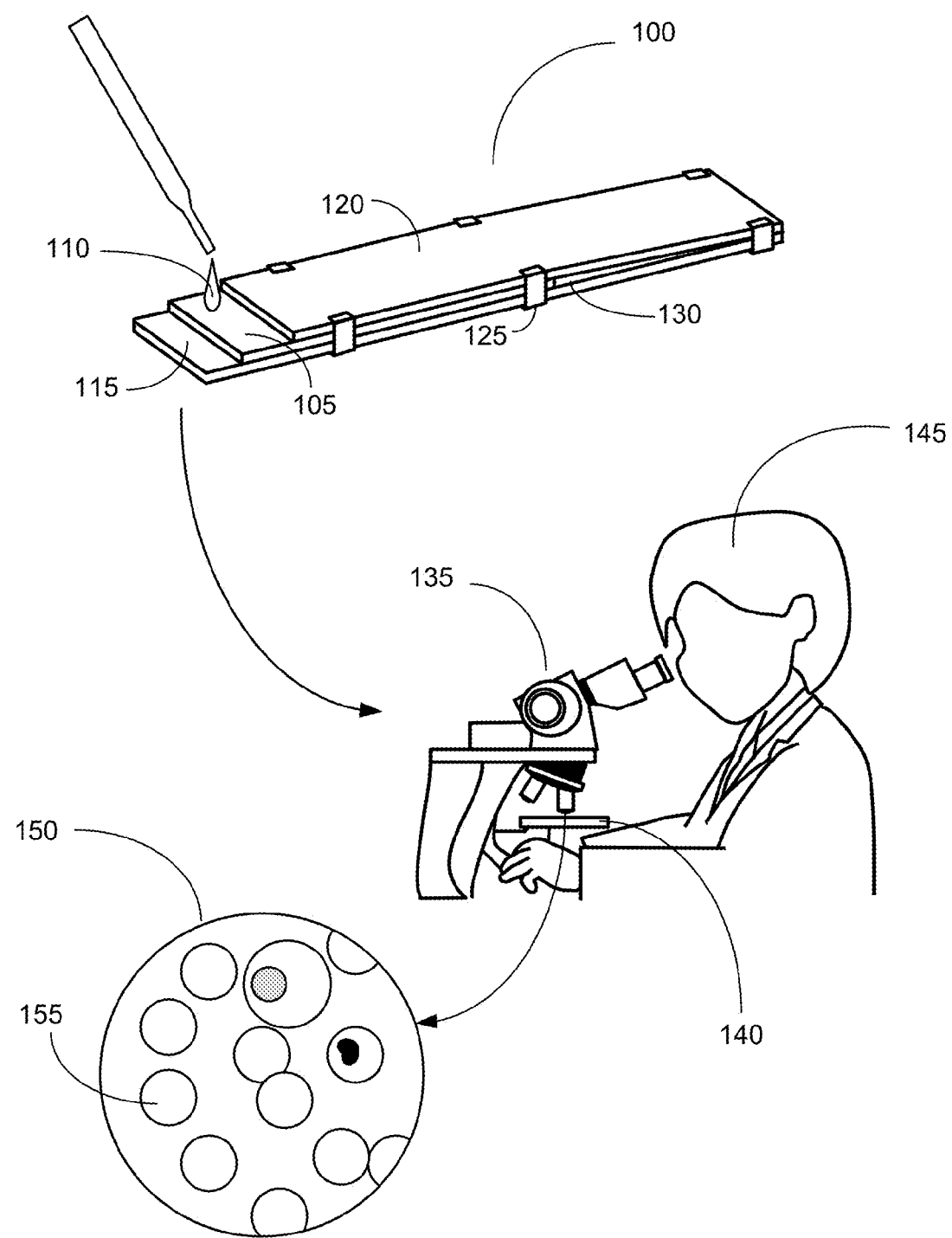
FIG. 1 illustrates aspects of a microfluidic microscopy device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Embodiments of a microfluidic microscopy device and methods are described herein for preparing and assessing a liquid sample for use in diagnosing a disorder. In an aspect, the microfluidic microscopy device includes an absorbent structure including at least one dry dye for a liquid to stain one or more components of a polar liquid, e.g., one or more components of a blood sample, as the polar liquid migrates through the microfluidic microscopy device. The microfluidic microscopy device further includes an optically transparent chamber allowing for microscopic observation of the stained one or more components of the polar liquid for aiding diagnosis of a medical condition.

With reference to FIG. 1, shown is an example of a microfluidic microscopy device 100 receiving polar liquid 110 and subsequently being viewed by user 145 with microscope 135, which can serve as a context for one or more devices and/or processes described herein. As shown, device 100 includes absorbent structure 105, support structure 115, lid structure 120, clamping structure 125, and tapered internal chamber 130. Absorbent structure 105 is configured to receive polar liquid 110 at a first end of absorbent structure 105 and to convey polar liquid 110 from the first end of absorbent structure 105 through an interior hydrophilic region to a second end of the absorbent structure 105 and into tapered internal chamber 130. For example, absorbent structure 105 can be an appropriately sized piece of absorbent paper. Polar liquid 110 can include a body fluid, e.g., a blood sample derived from a finger prick or blood draw of an individual. Other non-limiting examples of body fluids include amniotic fluid, bile, cerebrospinal fluid, peritoneal fluid, pleural fluid, saliva, seminal fluid, synovial fluid, tears, sweat, vaginal secretion, or urine. In an aspect, absorbent structure 105 includes at least one dry dye for a liquid wherein absorbent structure 105 is configured to convey polar liquid 110 from the first end of absorbent structure 105 through the hydrophilic region and the at least one dry dye for a liquid to the second end of absorbent structure 105. In an aspect, the at least one dry dye for a liquid is incorporated into absorbent structure 105 and solubilized or rehydrated in the presence of polar liquid 110 as it is conveyed through absorbent structure 105. For example, the at least one dry dye for a liquid can include a dye of a type to stain one or more cellular components, e.g., blood cells, in the polar liquid.

Device 100 further includes support structure 115 positioned adjacent to a first surface of absorbent structure 105. For example, support structure 115 may be positioned below absorbent structure 105, e.g., positioned adjacent to a lower surface of absorbent structure 105. However, in some embodiments, support structure 115 may be positioned adjacent to an upper surface or side surface of absorbent structure 105. In some embodiments, support structure 115 may be positioned adjacent to the entirety of the first surface of absorbent structure 105. In an aspect, support structure 115 includes a rigid structure, e.g., a non-deformable or non-flexible structure. In an aspect, support structure 115 includes glass and/or plastic. For example, support structure 115 can include a borosilicate microscope slide or similarly shaped glass or plastic structure. Support structure 115 includes a first end and a second end. In an aspect, the first end and/or the second end of support structure 115 extends beyond the first end and/or the second end of the adjacent surface of absorbent structure 105. The second end of support structure 115 includes a second end region positioned adjacent to the second end of absorbent structure 105.

Device 100 further includes lid structure 120 positioned adjacent to a second surface of absorbent structure 105. For example, lid structure 120 may be positioned above absorbent structure 105, e.g., positioned adjacent to an upper surface of absorbent structure 105. However, in some embodiments, lid structure 120 may be positioned adjacent to a lower surface or side surface of absorbent structure 105. In some embodiments, lid structure 120 may be positioned adjacent to the entirety of the second surface of absorbent structure 105. In an aspect, lid structure 120 is deformable, e.g., a flexible structure. For example, lid structure 120 can include a thin sheet of glass or plastic that bends when clamped together with absorbent structure 105 and support structure 115 with clamping structure 125. In an aspect, lid structure 120 includes glass and/or plastic. For example, lid structure 120 can include a borosilicate coverslip or similarly shaped glass or plastic structure. Lid structure 120 includes a first end and a second end. The second end of lid structure 120 projects beyond the second end of absorbent structure 105 and includes a second end region positioned adjacent to the second end of the absorbent structure and overlapping with the second end region of the support structure. In an aspect, the first end of lid structure 120 projects beyond the first end of absorbent structure 105. At least a portion of lid structure 120 and support structure 115 are optically transparent and suitable for microscopy.

Device 100 further includes clamping structure 125 positioned to maintain a relative position of support structure 115 and lid structure 120 to form tapered internal chamber 130. Polar liquid 110 is conveyed by capillary action from the first end of absorbent structure 105 through the at least one dry dye for a liquid to the second end of absorbent structure 105 and into tapered internal chamber 130. Tapered internal chamber 130 includes a variable internal depth dictated by the distance between an internal surface of support structure 115 facing an internal surface of lid structure 120. At least a portion of lid structure 120 and/or support structure 115 forming tapered internal chamber 130 is optically transparent and suitable for microscopy.

In some embodiments, device 100 is sized for use with a microscope. In the schematic shown in FIG. 1, device 100 is sized for placement on microscope stage 140 of microscope 135. Polar liquid 110 and its contents in tapered internal chamber 130 are viewed by user 145 through one or more objective lens of microscope 135. In this example, the microscopic field of view 150 of the contents of polar liquid 110 in tapered internal chamber 130 includes one or more cells 155 stained with the solubilized at least one dry dye for a liquid. Microscopic field of view 150 includes more or less of one or more cells 155 depending upon the internal thickness of tapered internal chamber 130. For example, the microscopic field of view 150 includes more cells near the second edge of absorbent structure 105 where tapered internal chamber 130 is at a maximum height, e.g., a "thick" view, as opposed to the end of tapered internal chamber 130 where the second ends of support structure 115 and lid structure 120 meet, e.g., a "thin" view. For example, the microscopic field of view 150 in tapered internal chamber 130 near the second edge of absorbent structure 105 may include multiple layers of cells while the microscopic field of view 150 toward where the second ends of support structure 115 and lid structure 120 meet may include a monolayer of cells. The variable depth of tapered internal chamber 130 allows variable depth viewing within microscopic field of view 150. In an aspect, a "thick" view and a "thin" view of a blood sample in tapered internal chamber 130 respectively simulate a thick blood smear and a thin blood smear.

Although user 145 is shown/described herein as a single illustrated figure, those skilled in the art will appreciate that user 145 may be representative of a human user, a robotic user (e.g., computational entity), and/or substantially any combination thereof (e.g., a user may be assisted by one or more robotic agents) unless context dictates otherwise.

Figure 2A:
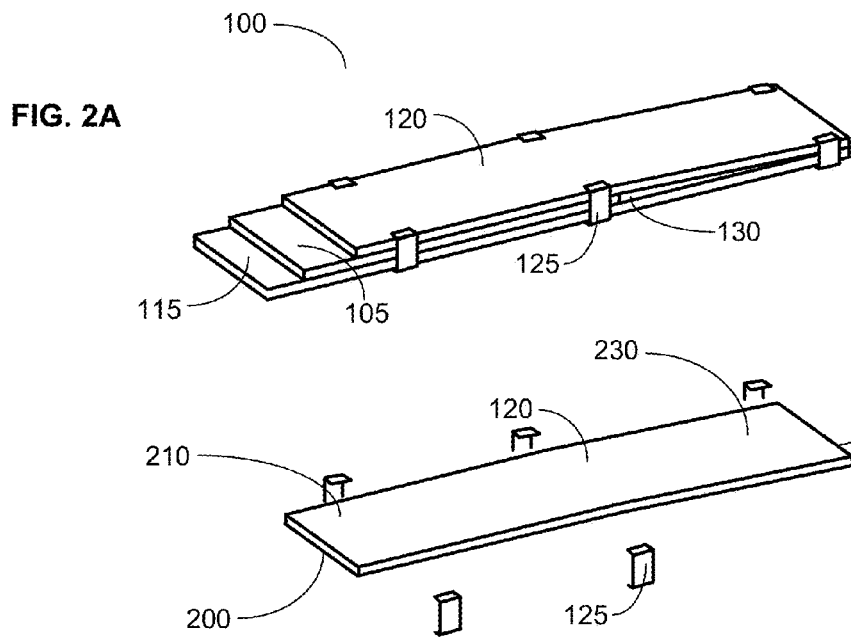
FIG. 2A is a schematic of a three-dimensional view of a microfluidic microscopy device.

FIG. 2 illustrates further aspects of microfluidic microscopy device 100. FIG. 2A is a schematic of an embodiment of a constructed device 100 including absorbent structure 105 positioned between support structure 115 and lid structure 120 and held together with clamping structure 125. Clamping structure 125 is positioned to maintain a relative position of support structure 115 and lid structure 120 to form tapered internal chamber 130.

Figure 2B:
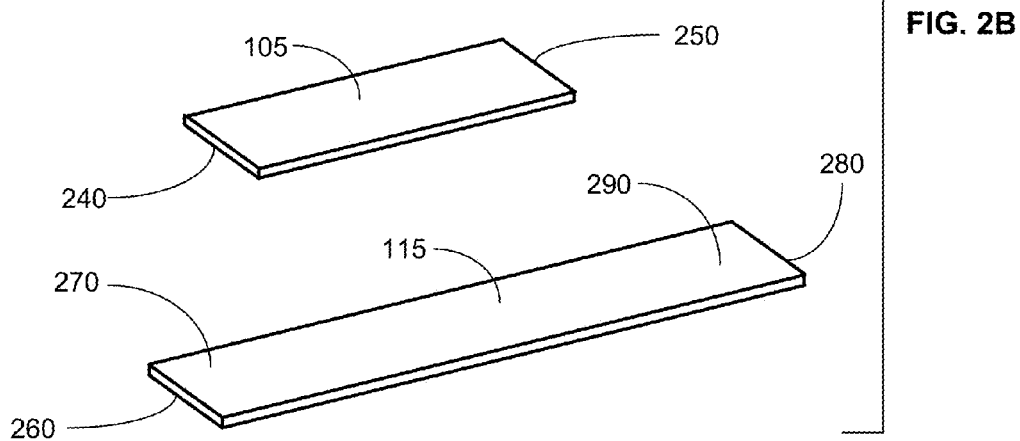
FIG. 2B is a schematic of a three-dimensional view of the microfluidic microscopy device shown in FIG. 2A.

FIG. 2B is a schematic of an embodiment of a deconstructed device 100, showing the individual components, e.g., lid structure 120, absorbent structure 105, support structure 115, and clamping structure 125. Lid structure 120 includes a first end 200 with a first end region 210 and a second end 220 and a second end region 230. Absorbent structure 105 includes first end 240 and second end 250. Support structure 115 includes a first end 260 with a first end region 270 and a second end 280 with a second end region 290.

Figure 2C:
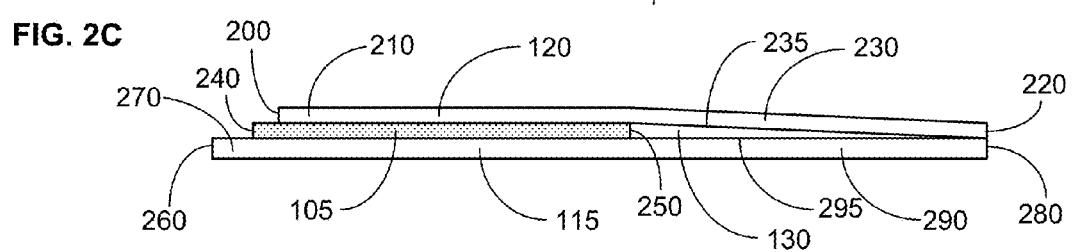
FIG. 2C is a schematic of a cross-sectional view through the microfluidic microscopy device shown in FIG. 2A.

FIG. 2C is a schematic of a cross-section through device 100. Device 100 includes absorbent structure 105 with a first end 240 and a second end 250, absorbent structure 115 including an interior hydrophilic region. Absorbent structure 105 is configured to convey a polar liquid from first end 240 through the interior hydrophilic region to second end 250. In some embodiments, the interior hydrophilic region of absorbent structure 105 includes at least one dry dye for a liquid and absorbent structure 105 is configured to convey a polar liquid from first end 240 through the interior hydrophilic region and the at least one dry dye for a liquid to second end 250 and into tapered internal chamber 130. Device 100 further includes support structure 115 positioned adjacent to a first surface of absorbent structure 105, support structure 115 including first end 260 and second end 280, first end 260 of support structure 115 including first end region 270 and second end 280 of support structure 115 including second end region 290 positioned adjacent to second end 250 of absorbent structure 105. Device 100 further includes lid structure 120 adjacent to a second surface of absorbent structure 105, lid structure 120 including first end 200 and second end 220, first end 200 of lid structure 120 including first end region 210 and second end 220 of lid structure 120 including second end region 230 positioned adjacent to second end 250 of absorbent structure 105 and overlapping with second end region 290 of support structure 115. Device 100 further includes clamping structure 125, as shown in FIGS. 2A and 2B, positioned to maintain a relative position of support structure 115 and lid structure 120 to form tapered internal chamber 130 adjacent to second end 250 of absorbent structure 105, tapered internal chamber 130 including internal surface 295 of second end region 290 of support structure 115 facing internal surface 235 of second end region 230 of lid structure 120. Tapered internal chamber 130 further includes an outflow region (not shown in this view).

Absorbent Structure

Device 100 includes an absorbent structure. The absorbent structure includes an interior hydrophilic region and is configured to convey a polar liquid from a first end of the absorbent structure through the interior hydrophilic region to a second end of the absorbent structure and into the tapered internal chamber of the device. When wetted with the polar liquid, the absorbent structure provides a motive force to convey the polar liquid from the wet portions of the absorbent structure to the dry portions of the absorbent structure. In an embodiment, the main motive force includes capillary action. The absorbent structure further provides a motive force to convey the polar liquid from the second end of the absorbent structure and into the tapered internal chamber formed from an internal surface of the support structure facing an internal surface of the lid structure.

In an aspect, the absorbent structure can be characterized based on surface characteristics, surface area, shape, capillary flow rate, thickness, porosity, and pore size. In an aspect, the absorbent structure is a flat structure, e.g., a piece of paper, configured for positioning between a support structure and a lid structure. In an aspect, the absorbent structure has a rectangular shape in a first and second dimension, e.g., plan view, and is relatively thin in a third dimension. For example, in some embodiments, the absorbent structure includes an appropriately sized sheet of absorbent paper, e.g., filter or chromatography paper. In an embodiment, the absorbent structure has a flat, square shape. In an embodiment, the absorbent structure has a flat, triangular shape. In an embodiment, the absorbent structure is a flat structure including 5 sides. In an embodiment, the absorbent structure is a flat structure including 6 or more sides. For example, in some embodiments, the absorbent structure in a plan view includes 6 sides, 7 sides, 8 sides, 9 sides, 10 sides, or more sides. In some embodiments, the absorbent structure includes a combination of at least one straight side and at least one curved side. In an embodiment, the absorbent structure is circular or oval in shape in a plan view. In some embodiments, the shape of the absorbent structure is long and narrow.

In some embodiments, the shape of the absorbent structure influences the rate of flow through the absorbent structure. For example, a fluid front moves more quickly through a long, narrow, rectangular absorbent structure versus less quickly though a wider rectangular absorbent structure. See, e.g., International Patent Publication WO 2010/008524 to Sibbett & Lopez titled "Capillary Driven Lateral Flow Device", which is incorporated herein by reference. In an aspect, the shape of the absorbent structure may be formed using a computer controlled X-Y knife plotter. In an aspect, the shape of the absorbent structure may be formed using a $CO_2$ laser.

In an aspect, the thickness of the absorbent structure at the second end of the absorbent structure adjacent to the tapered internal chamber dictates the maximum height or depth of the tapered internal chamber. For example, if the absorbent structure is 0.5 mm in thickness, the maximal height within the tapered internal chamber can be 0.5 mm. In an aspect, the thickness of the absorbent structure ranges from about 0.01 mm thick to about 5 mm thick. For example, in some embodiments, the thickness of the absorbent structure can be 0.01 mm, 0.02 mm, 0.03 mm, 0.04 mm, 0.05 mm, 0.06 mm, 0.07 mm, 0.08 mm, 0.09 mm, 0.1 mm, 0.12 mm, 0.14 mm, 0.16 mm, 0.18 mm, 0.2 mm, 0.22 mm, 0.24 mm, 0.26 mm, 0.28 mm, 0.30 mm, 0.35 mm, 0.40 mm, 0.45 mm, 0.50 mm, 0.55 mm, 0.60 mm, 0.65 mm, 0.70 mm, 0.75 mm, 0.80 mm, 0.85 mm, 0.90 mm, 0.95, 1.0 mm, 2.0 mm, 3.0 mm, 4.0 mm, or 5.0 mm. In an aspect, the thickness of the absorbent structure influences the bed volume of the absorbent structure, wherein the bed volume is the total accessible volume of the absorbent material for the polar liquid and is a function of the dimensions of the absorbent structure and the porosity of the absorbent structure.

In an aspect, the absorbent structure includes one or more layers of a porous material. In an aspect, the absorbent structure includes a thin sheet of paper material formed from cellulosic fibers. Non-limiting sources of cellulosic fibers for generating paper include wood, cotton, jute, flax, hemp, bamboo, ramie, sisal, bagasse, grass, or straw. In an aspect, the absorbent structure includes a form of fibrous paper, e.g., filter paper or chromatography paper. In an aspect, the absorbent structure includes a form of glass fiber. In an aspect, the absorbent structure includes ceramic foam. In an aspect, the absorbent structure includes porous silicon. Other non-limiting examples of porous materials for use in the absorbent structure include cellulose, sodium polyacrylate, silica fiber, nitrocellulose, cellulose ester, polyether sulfone, polysulfone, polyethylene tetrafluoride, polyvinylidene fluoride, polycarbonate, polypropylene, polyamide, nylon, polyester, cotton, or stainless steel fiber.

In an aspect, the absorbent structure can include a paper that is a form of filter paper or chromatography paper. For example, the absorbent structure can include a filter or chromatography paper fabricated from high-quality cotton linters with high alpha-cellulose content. For example, in some embodiments, the absorbent structure can include an appropriately sized piece of commercially available, standard grade filter paper. Non-limiting examples of standard grade filter/chromatography paper range in thickness from 0.15 mm to 1.5 mm with particle retention sizes ranging from about 2 microns to greater than 25 microns. For example, Whatman Grade 1 filter paper has a thickness of 0.18 mm, a medium particle retention value of 11 microns and a linear flow rate of 130 mm/30 min. Other non-limiting examples of commercially available filter papers are provided by Ahlstrom North America, LLC (Alpharetta, Ga.); GE Healthcare (Fairfield, Conn.); Sartorius USA (Bohemia, N.Y.).

In an aspect, the absorbent structure includes a structure composed at least in part of glass fibers. In an aspect, the absorbent structure includes borosilicate glass fiber membranes. Glass fiber membranes or pads are available from commercial sources (from, e.g., Sterlitech, Corp., Kent, Wash.; Alhstrom, Helsinki, Finland).

In an aspect, the absorbent structure includes nitrocellulose. For example, the absorbent structure can include cellulose esterfied with a nitrating acid (e.g., sulfuric acid and nitric acid). In an aspect, the absorbent structure includes a combination of cellulose nitrate and cellulose acetate. Non-limiting examples of nitrocellulose/cellulose acetate membranes with uniform pore structures ranging from 0.1 micron to 8 micron are available from commercial sources (from, e.g., Sterlitech Corp., Kent, Wash.; Life Sciences Products, Inc., Denver, Colo.). Methods for generating cellulose nitrate polymer membranes and controlling pore structure are described in Flynn, et al. (2013) "Control of Pore Structure Formation in Cellulose Nitrate Polymer Membranes" *Adv. Chem. Sci.* 2:9-18, which is incorporated herein by reference.

In an aspect, the absorbent structure includes one or more layers of open, small diameter channels. See, e.g., U.S. Patent Application 2012/0225446 to Wimberger-Friedl et al. titled "Preparation of thin layers of fluid containing cells for analysis," which is incorporated herein by reference. In an aspect, the surfaces of the open, small diameter channels include at least one dry dye for a liquid.

In an aspect, the flow properties through the absorbent structure are dependent upon the pore size of the absorbent material, e.g., the larger the pore size, the faster the flow rate. In an aspect, the flow properties through the absorbent structure are dependent on the porosity of the absorbent material, e.g., the percentage of the absorbent structure taken up by pores relative to the total volume. In an aspect, the porosity of the absorbent structure is configured to allow the polar liquid and at least a part of its contents, e.g., cells, to be drawn from the first end of the absorbent structure to the second end of the absorbent structure. For example, the porosity of the absorbent structure can be configured to accommodate flow of cells found in the blood stream, examples of which include red blood cells, white blood cells, and platelets. In an aspect, the average pore size of the absorbent structure ranges from about 0.1 microns to about 100 microns. For example, in some embodiments, the average pore size of the absorbent structure can be 0.1 microns, 0.2 microns, 0.5 microns, 0.7 microns, 1 micron, 2 micron, 3 micron, 4 micron, 5 micron, 6 micron, 7 micron, 8 micron, 9 micron, 10 micron, 11 micron, 12 micron, 13 micron, 14 micron, 15 micron, 16 micron, 17 micron, 18 micron, 20 micron, 25 micron, 30 micron, 40 micron, 50 micron, 60 micron, 70 micron, 80 micron, 90 micron, or 100 micron.

In an aspect, the absorbent structure includes an average pore size sufficient to allow passage of one or more cellular components of the polar liquid. In an aspect, the porosity of the absorbent structure is configured to accommodate red blood cells, e.g., an average pore size and porosity sufficiently large to allow red blood cells in the polar liquid to flow from the first end of the absorbent structure to the second end of the absorbent structure. Red blood cells range in diameter from 6-8 microns, but are deformable to as small as 2-3 microns in diameter. In an aspect, the porosity of the absorbent structure is configured to accommodate white blood cells, e.g., an average pore size and porosity sufficiently large to allow white blood cells in the polar liquid to flow from the first end of the absorbent structure to the second end of the absorbent structure. White blood cells range in diameter from 7 microns to 20 microns and include neutrophils and eosinophils (10-12 microns), basophils (12-15 um), lymphocytes (7-15 um), and monocytes (12-20 um). In an aspect, the porosity of the absorbent structure is sufficient to accommodate macrophages, the latter of which can be as large as 60-80 microns.

In an aspect, the porosity is configured to allow red blood cells infected with a parasite, e.g., *Plasmodium*-infected red blood cells, to be drawn through the absorbent material. *Plasmodium*-infected red blood cells are about the same size as uninfected red blood cells (about 6-8 microns) but are less deformable. For example, the minimum cylindrical diameter of a deformed uninfected red blood cell ranges from 2 to 3 um while minimum cylindrical diameter of a deformed *Plasmodium* infected red blood cell ranges from 2.5 to 4.5 um. See, e.g., Herricks et al. (2009) "Deformability limits of *Plasmodium falciparium*-infected red blood cells" Cellular Microbiology, 11:1340-1353; and Hou et al. (2010) "Deformability based cell margination—A simple microfluidic design for malaria-infected erythrocyte separation" *Lab Chip* 10:2605-2613, which are incorporated herein by reference.

In an aspect, the properties of the absorbent structure contribute to the capillary flow rate or migration speed of a polar liquid front moving along the length of the absorbent structure. In an aspect, the migration speed decays exponentially as the polar liquid front travels along the membrane. In an aspect, capillary flow time is measured. This is the time required for the polar liquid to move from the first end of the absorbent structure to the second end of the absorbent structure and is inversely related to the flow rate.

Hydrophilic Region

The absorbent structure includes an interior hydrophilic region suited for conveying a polar liquid from a first end of the absorbent structure to the second end of the absorbent structure. In an aspect, the hydrophilic region of the absorbent structure is an inherent property of the absorbent structure. For example, cellulose, a common component of paper, is naturally hydrophilic. In an aspect, the hydrophilic region is manufactured into the absorbent structure. Non-limiting examples of methods for increasing the hydrophilicity of a material include various gas plasma treatments, e.g., plasma with non-polymerized gases, oxygen, nitrogen, sulfur, and combinations thereof, and coatings, e.g., Si—N, Si—O or Si—H coatings, polyamine, fluoride coatings. See, e.g., European Patent Application EP2559806 to Mozetic et al. titled "Method for increasing hydrophilicity of polymeric materials," and Clinical Laboratory News "µPADS (Microfluidic Paper-based Analytical Devices)" published online Jul. 27, 2012, accessed online Jul. 22, 2013, which are incorporated herein by reference.

Hydrophobic Region

In an embodiment, the absorbent structure includes at least one interior hydrophobic region. In an aspect, the at least one interior hydrophobic region is configured to repel the polar liquid. In an aspect, the at least one interior hydrophobic region is configured to absorb the polar liquid at a slower rate than the surrounding hydrophilic regions of the absorbent structure. In an aspect, the at least one interior hydrophobic region can be incorporated into the absorbent structure to modulate the flow of polar liquid through the absorbent structure. In an aspect, the placement/pattern of interior hydrophobic regions in the absorbent structure dictates flow properties. For example, one or more interior hydrophobic region can be used to channel the polar liquid in specific directions through the absorbent structure. For example, one or more interior hydrophobic regions can be used to create a narrowing, e.g., bottle-neck, in the flow path that alters the flow rate of a polar liquid through the absorbent structure.

In an aspect, the interior hydrophobic region is constructed using any of a number of fabrication methods, non-limiting example of which include photolithography, plotting, ink jet etching, plasma treatment, wax printing, ink jet printing, flexography printing, screen printing, or laser treatment. In an aspect, the interior hydrophobic region is generated by physically blocking pores in the absorbent structure using, for example, photoresist and polydimethylsiloxane (PDMS). In an aspect, the interior hydrophobic region is generated by physical deposition of one or more reagents on the absorbent structure, for example, paraffin wax or polystyrene. For example, a hydrophobic material, e.g., wax, can be printed onto the absorbent structure, e.g., filter paper, based on a digital pattern using a printer, e.g., a wax printer (Xerox Phaser 6580, Norwalk, Conn.). See, e.g., Jahanshahi-Anbuhi et al. (2012) "Creating fast flow channels in paper fluidic devices to control timing of sequential reactions" *Lab Chip* 12:5079-5085, which is incorporated herein by reference. In an aspect, the interior hydrophobic region is generated by chemical modification of the absorbent structure, for example, chemical modification with alkyl ketene dimer (AKD). For example, chemical modification of a cellulose-based absorbent structure can be achieved by applying agents that react with the —OH groups of cellulose, imparting hydrophocity to the fibers. See, e.g., Li et al. (2012) "A perspective on paper-based microfluidics: Current status and future trends" *Biomicrofluidic* 6:011301, which is incorporated herein by reference. Other non-limiting examples of hydrophobic materials include silanes, including fluoroalkylsilanes, phenyl silanes, and chlorosilanes; nylon, polyethylene, polychlorotrifluoroethylene, polypropylene, poly t-butyl methacrylate, fluorinated ethylene propylene, hexatriacontane, polytetrafluoroethylene, poly(hexafluoropropylene) and polyisobutylene.

Flow Through the Absorbent Material

In an aspect, flow through the absorbent material and into the tapered internal chamber occurs by capillary flow and can be described in terms of Washburn's equation:

$$L_2 = \frac{\gamma Dt}{4\eta}$$

where t is the time for a liquid of a dynamic viscosity $\eta$ and surface tension $\gamma$ to penetrate a distance L into the capillary whose pore diameter is D. In some embodiments, this equation can be used to calculate how long it will take for the leading edge of the polar liquid to pass through the absorbent structure and into the tapered internal chamber. For example, the rate of flow through horizontal capillaries can be described as $$\frac{dl}{dt} = \frac{r}{\eta}\frac{\gamma}{4l}\cos\theta$$

or the rate at which a liquid penetrates any horizontal capillary under its own capillary pressure and is directly proportional to the radius r of the capillary, the cosine of the angle of contact cos $\theta$, to the ratio of the surface tension $\gamma$ to the viscosity of the liquid $\eta$ and inversely proportional to the length l already filled by the liquid. See, e.g., Washburn (1921) "The Dynamics of Capillary Flow" *Physical Review* 17:273-283, which is incorporated herein by reference.

In an aspect, flow through the absorbent structure and into the tapered internal chamber can be described in terms of Darcy's law, which describes flow of a liquid through a porous medium. Darcy's law is a proportional relationship between the discharge rate through the porous medium, the viscosity of the fluid, and the pressure drop over a given distance.

$$Q = \frac{-kA}{\mu}\frac{(P_b - P_a)}{L}$$

where Q is volumetric flow rate, k is permeability of the material, A is the normal cross-sectional are of the porous material, $P_b$–$P_a$ is the pressure difference across the length of the material from point A to point B, $\mu$ is viscosity of the liquid, and L is the length of the material in the direction of fluid. Fluid flows from high pressure to low pressure and will flow from point A to point B when the change in pressure is negative (where $P_a$>$P_b$).

In an aspect, the thickness gradient created by the positioning of the support structure and the lid structure on either side of the absorbent structure to form the tapered internal chamber as well as the presence of hydrophilic surfaces drives fluid flow from the first end of the absorbent structure through the second end of the absorbent structure and into the tapered internal chamber.

In an aspect, the properties of the absorbent structure dictate the flow properties through the absorbent structure. Non-limiting examples of properties of the absorbent structure that can dictate flow properties through the absorbent structure include shape, thickness, pore size, porosity, and the presence and patterning of interior hydrophobic regions.

In an aspect, the shape of the absorbent structure dictates the flow properties of the liquid through the absorbent structure. For example, the absorbent structure can be shaped to include areas of narrowing, e.g., with notches cut out of the absorbent structure, to reduce the width of the flow path and change the flow rate. For example, the absorbent structure can be shaped to include a first shape, e.g., a rectangle, followed by a second shape, e.g., a flared shape. See, e.g., International Patent Publication WO 2010/008524 to Sibbett & Lopez titled "Capillary Driven Lateral Flow Device", which is incorporated herein by reference.

In an aspect, the placement/pattern of interior hydrophobic regions within the absorbent structure may be used to modulate the flow properties through the absorbent structure. For example, one or more interior hydrophobic regions can be used to create a narrowing, e.g., bottle-neck, in the flow path that alters the flow rate of a polar liquid through the absorbent structure.

Dry Dye for a Liquid

In an aspect, the microfluidic microscopy device includes an absorbent structure with at least one dry dye for a liquid. The at least one dry dye for a liquid is configured to mix with a polar liquid sample as it passes from a first end of the absorbent structure to a second end of the absorbent structure. For example, the at least one dry dye for a liquid can be configured to mix with a blood sample or other body fluid sample as the sample and its cellular components migrate from the first end of the absorbent structure to the second end of the absorbent structure and into the tapered internal chamber. The at least one dry dye is of a chemical structure to be at least partially soluble in the polar liquid.

In an aspect, the at least one dry dye for a liquid is positioned within the absorbent structure to be uniformly dispersed in the polar liquid for use as a calibration tool. The intensity of the solubilized dye at any depth along the tapered internal channel can be used to calibrate the volume at that depth. In an aspect, a calibration curve is generated from the intensity of the solubilized dye at the maximal depth of the tapered internal chamber, e.g., adjacent to the second end of the absorbent material, and the intensity of the solubilized dye at the minimal depth of the tapered internal chamber, e.g., where the internal surface of the second end region of the support structure and the internal surface of the second end region of the lid structure meet under the constrains of the clamping structure.

In an aspect, the at least one dry dye for a liquid is of a type to stain one or more cells in the polar liquid. For example, the at least one dry dye for a liquid can be of a type to stain one or more of red blood cells and/or white blood cells in a blood sample. Non-limiting examples of cells in a blood sample include red blood cells, white blood cells, platelets, bacteria, metastatic tumor cells, parasites, and parasite-infected cells, e.g., *Plasmodium*-infected red blood cells. The at least one dry dye for a liquid can be of a type to stain one or more components of a cell. In an aspect, the at least one dry dye is of a type to stain one or more components on the exterior of a cell, e.g., one or more components of a cell membrane or a cell wall. In an aspect, the at least one dry dye is of a type to stain one or more components in the interior of a cell, e.g., lipids, DNA, RNA, proteins, organelles, and the like. In an aspect, the at least one dry dye for a liquid is of a type to stain one or more organelles of a cell, non-limiting examples of which include adiposomes, cytoplasm, cytoskeleton, endoplasmic reticulum, Golgi complex, intracellular membranes, lysosomes, endosomes, mitochondria, nuclear envelope, nucleoli, nucleus, peroxisomes, plasma membrane.

In an aspect, the at least one dry dye for a liquid is conjugated to a binding agent, the binding agent configured to recognize one or more specific components of the polar liquid. For example, the binding agent may include an antibody configured to recognize and bind one or more specific components of the polar liquid, e.g., one or more specific cell types or parts thereof. For example, the binding agent may include an aptamer configured to recognize and bind one or more specific components of the polar liquid.

Non-limiting examples of binding agents include antibodies, aptamers, ligands, receptors, peptide nucleic acids, oligonucleotides, and lectins.

In an aspect, the at least one dry dye for a liquid can be conjugated to a binding agent using any of a number of crosslinking reagents. For example, the at least one dry dye for a liquid can be conjugated to the binding agent through amine groups, carbohydrate groups, sulfhydryl groups, or combinations thereof using a homobifunctional, heterobifunctional, and/or photoreactive crosslinking reagent. For example, a fluorescing dye, e.g., fluorescein, can be conjugated to a binding agent, e.g., an antibody using 5-carboxyfluorescein succinimidylester. See, e.g., U.S. Pat. No. 6,911,535 to Schwartz titled "Biomolecule/Polymer Conjugates," which is incorporated herein by reference. A variety of crosslinking agents for adding a fluorescing dye are available from commercial sources (from, e.g., Solulink, Inc., San Diego, Calif.; Life Technologies Corp., Carlsbad, Calif.; and Pierce-Thermo Scientific, Rockford, Ill.).

In an aspect, the at least one dry dye for a liquid can include at least one fluorescent dye. A non-limiting example of a fluorescent dye for staining proteins includes RuBPS (tetrasodium tris(bathopheanthroline disulfonate)ruthenium (II). Non-limiting examples of fluorescent dyes for staining nucleic acid include propidium iodine, ethidium bromide, ethidium monoazide, acridine orange, GelRed™ and GelGreen™ (Biotium Inc., Hayward, Calif.), Hoechst 33258, Hoechst 33342, SYBR Green (Invitrogen, Carlsbad, Calif.), SYTO Red Fluorescent Nucleic Acid Stains (Invitrogen, Carlsbad, Calif.), SYTO Blue Fluorescent Nucleic Acid Stains (Invitrogen, Carlsbad, Calif.), YOYO Nucleic Acid Stains (Invitrogen, Carlsbad, Calif.), hydroethidine, thiazole orange, DAPI (4',6-diamidno-2-phenylindol), Pico Green, Vybrant Dye-Cycle Green, others. See, e.g., Jouin et al. (2004) "Double staining of *Plasmodium falciparum* nucleic acids with hydroethidine and thiazole orange for cell cycle stage analysis by flow cytometry" *Cytometry Part A* 57A: 34-38; and Guy et al. (2007) "The use of fluorescence enhancement to improve the microscopic diagnosis of falciparum malaria" *Malaria J.* 6:89, which are incorporated herein by reference.

In an aspect, the at least one dry dye for a liquid can include a fluorophore or fluorescing dye conjugated to a binding agent. Non-limiting examples of fluorophores or fluorescing dyes include fluorescein (FITC), indocyanine green (ICG) and rhodamine B, red and near infrared emitting fluorophores (600-1200 nm) including cyanine dyes such as Cy5, Cy5.5, and Cy7 (Amersham Biosciences, Piscataway, N.J., USA) and/or a variety of Alexa Fluor dyes such as Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., USA). Additional fluorophores include IRDye800, IRDye700, and IRDye680 (LI-COR, Lincoln, Nebr., USA), NIR-1 and 105-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, CA), NIAD-4 (ICx Technologies, Arlington, Va.). Other fluorescing dyes include BODIPY-FL, europium, green, yellow and red fluorescent proteins, and/or luciferase.

In an aspect, the at least one dry dye for a liquid can include at least one colored dye or vital stain. In an aspect, the at least one dry dye for a liquid is of a chemical structure to stain one or more components of a cell. Non-limiting examples of colored dyes or stains for use in staining cells include eosin, hematoxylin, methylene blue, azure A, azure B, Bismarck brown, carmine, coomassie blue, crystal violet, fuchsin, iodine, malachite green, methyl green, toluoylene red, Nile blue, and Nile red, osmium tetroxide, and safranin.

In an aspect, the absorbent structure includes two or more dyes configured to stain different components of a cell or different types of cells. For example, cells can be stained with a combination of hematoxylin and eosin in which hematoxylin stains the nuclei blue and eosin stains intracellular or extracellular proteins red, pink, and orange. For example, cellular components of a blood sample can be differentially stained using a Romanowsky stain, a combination of a cationic dye, e.g., azure A, B, and/or methylene blue, and an anionic dye, e.g., eosin Y. Non-limiting variations of the Romanowsky stain include Giemsa, Wright, or Field stains, containing various amounts of oxidized methylene blue, azure A, azure B, and eosin Y dyes. Eosin Y stains the cytoplasm of cells an orange or pink color while methylene blue and azure B stain the nucleus varying shades of blue to purple. In an aspect, the at least one dry dye for a liquid includes the components of Giemsa or Field stain for use in staining *Plasmodium*-infected red blood cells to diagnose malaria.

In an aspect, the at least one dry dye for a liquid includes a first fluorescing dye for staining DNA and/or RNA and a second fluorescing dye for staining a plasma membrane or cytoplasmic component. In an aspect, the second fluorescing dye is conjugated to a binding agent. For example, the absorbent structure may include reagents for detecting *Plasmodium*-infected red blood cells that include a first fluorescing dye, e.g., acridine orange, for staining DNA and/or RNA and a second fluorescing dye attached to an antibody, e.g., an antibody that recognizes *Plasmodium falciparum* erythrocyte membrane protein 1 (PfEMP1), a parasite protein exported to the surface of infected red blood cells.

Figure 3A:
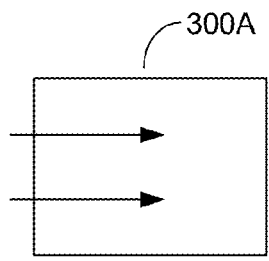
FIG. 3A is a schematic of a top view of an absorbent structure.
Figure 3B:
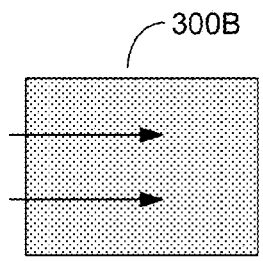
FIG. 3B is a schematic of a top view of an absorbent structure with a dry dye for a liquid.
Figure 3C:
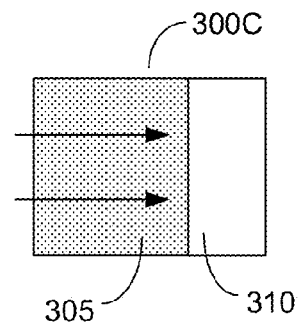
FIG. 3C is a schematic of a top view of an absorbent structure with a first portion including a dry dye for a liquid and a second portion.

In an aspect, two or more dyes are mixed together such that staining of cells in the polar liquid with one or more dyes occurs simultaneously. In an aspect, two or more dyes are separated in different regions of the absorbent structure such that staining of cells in the polar liquid with two or more dyes occurs sequentially. FIGS. 3A-3I are top view schematics of embodiments of an absorbent structure. The arrows moving from left to right indicate the flow of a polar liquid from a first end of an absorbent structure to a second end of the absorbent structure. FIG. 3A is a schematic of an absorbent structure 300A lacking at least one dry dye for a liquid. In an aspect, absorbent structure 300A may be used when the polar liquid is pre-treated with at least one dye prior to applying the polar liquid to the first end of a microfluidic microscopy device, absorbent structure 300A configured to remove excess dye that is not otherwise taken up by one or more components of the polar sample, e.g., one or more cells. FIG. 3B is a schematic of an absorbent structure 300B including at least one dry dye for a liquid uniformly distributed throughout the absorbent structure. In an aspect, a portion of the absorbent structure includes at least one dry dye for a liquid. For example, FIG. 3C is a schematic of absorbent structure 300C including a first portion 305 including at least one dry dye for a liquid and a second portion 310 lacking at least one dry dye for a liquid. In an aspect, absorbent structure 300C may be used to stain one or more components of the polar liquid in first portion 305 and to remove excess dye in second portion 310 prior to migrating the polar liquid into the tapered internal chamber of the device.

Figure 3D:
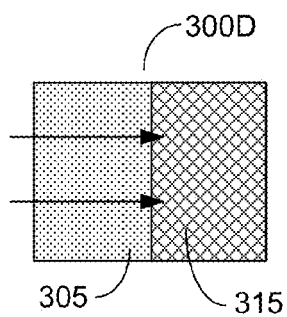
FIG. 3D is a schematic of a top view of an absorbent structure with a first portion including a dry dye of a first type for a liquid and a second portion including a dry dye of a second type for a liquid.
Figure 3E:
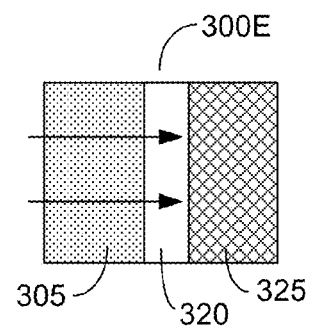
FIG. 3E is a schematic of a top view of an absorbent structure with a first portion including a dry dye of a first type for a liquid, a second portion, a third portion including a dry dye of a second type for a liquid.
Figure 3F:
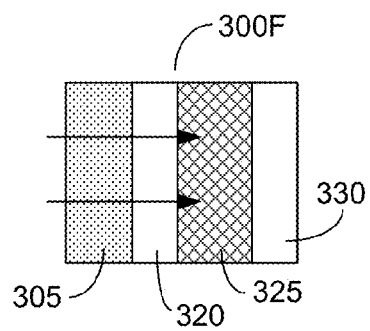
FIG. 3F is a schematic of a top view of an absorbent structure with a first portion including a dry dye of a first type for a liquid, a second portion, a third portion including a dry dye of a second type for a liquid, and a fourth portion.

In an aspect, at least one first portion of the absorbent structure includes at least one dry dye of a first type for a liquid and at least one second portion of the absorbent structure includes at least one dry dye of a second type for a liquid. In an aspect, the at least one first portion of the absorbent structure including the at least one dry dye of the first type for a liquid is positioned in a region which is parallel to the at least one second portion of the absorbent structure including the at least one dry dye of the second type for a liquid and perpendicular to flow of the polar liquid from the first end of the absorbent structure to the second end of the absorbent structure. For example, FIG. 3D is a schematic of absorbent structure 300D including a first portion 305 including at least one dry dye of a first type for a liquid and a second portion 315 including at least one dry dye of a second type for a liquid. For example, absorbent structure 300D may be used to sequentially stain one or more components of the polar liquid with two or more dry dyes for a liquid. For example, absorbent structure 300D might include a first portion including eosin and a second portion including hematoxylin. FIG. 3E is a schematic of absorbent structure 300E including a first portion 305 including at least one dry dye of a first type for a liquid, a second portion 320 lacking at least one dry dye of a liquid, and a third portion 325 including at least one dry dye of a second type for a liquid. For example, absorbent structure 300E may be used to sequentially stain one or more components of a polar liquid with at least one first dye type in first portion 305, remove excess of the at least one first dye type in second portion 320, and stain the one or more components of the polar liquid with at least one second dye type in third portion 325. FIG. 3F is a schematic of absorbent structure 300F including a first portion 305 including at least one dry dye of a first type for a liquid, a second portion 320 lacking at least one dry dye for a liquid, a third portion 325 including at least one dry dye of a second type for a liquid, and fourth portion 330 lacking at least one dry dye for a liquid. For example, absorbent structure 300F may be used to sequentially stain one or more components of a polar liquid with at least one first dye type in first portion 305, remove any excess of the at least one first dye type in second portion 320, stain the one or more components of the polar liquid with at least one second dye type in third portion 325, and remove any excess of the at least one second dye type in fourth portion 330 before migrating the polar liquid into the tapered internal chamber.

Figure 3G:
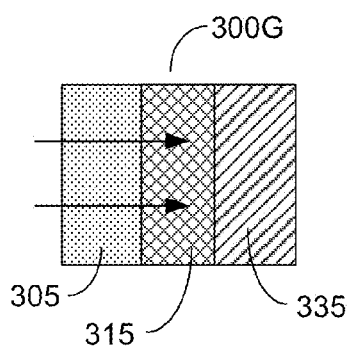
FIG. 3G is a schematic of a top view of an absorbent structure with a first portion including a dry dye of a first type for a liquid, a second portion including a dry dye of a second type for a liquid, and a third portion including a dry dye of a third type for a liquid.
Figure 3H:
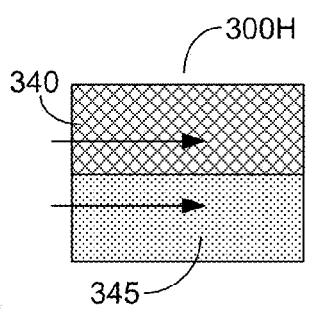
FIG. 3H is a schematic of a top view of an absorbent structure with a first portion including a dry dye of a first type for a liquid and a second portion including a dry dye of a second type for a liquid.

In an aspect, the absorbent structure may include three or more portions, each portion including one or more dry dyes for a liquid. For example, FIG. 3G is a schematic of absorbent structure 300G including a first portion 305 including at least one dry dye of a first type for a liquid, a second portion 315 including at least one dry dye of a second type for a liquid, and a third portion 335 including at least one dry dye of a third type of a liquid. It is contemplated that additional portions may be included in the absorbent structure. For example, the absorbent structure may include additional portions lacking at least one dry dye for a liquid placed after each of first portion 305, second portion 315, and/or third portion 335. For example, the absorbent structure may include additional portions including additional dye types.

Figure 3I:
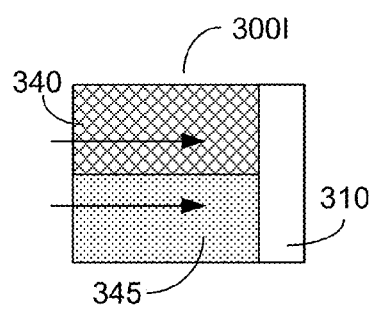
FIG. 3I is a schematic of a top view of an absorbent structure with a first portion including a dry dye of a first type for a liquid, a second portion including a dry dye of a second type for a liquid, and a third portion.

In an aspect, the absorbent structure may be configured to migrate the polar liquid simultaneously but separately through different dye types. In an aspect, the at least one first portion of the absorbent structure including the at least one dry dye of a first type of a liquid is positioned in a region which is parallel to the at least one second portion of the absorbent structure including at least one dry dye of a second type for a liquid and parallel to the flow of the polar liquid from the first end of the absorbent structure to the second end of the absorbent structure. For example, FIG. 300H is a schematic of absorbent structure 300H including a first portion 340 including at least one dry dye of a first type for a liquid positioned parallel to second portion 345 including at least one dry dye of a second type for a liquid and parallel to the direction of liquid flow. Absorbent structure 300H may be used to simultaneously, but separately, stain one or more components of the polar liquid with separate dyes. For example, a first portion 340 might include eosin for staining the cytoplasm of cells in a polar liquid while second portion 345 includes hematoxylin for staining the nuclei of the cells in the polar liquid. FIG. 3I is a schematic of absorbent structure 300I including first portion 340 including at least one dry dye of a first type for a liquid, second portion 345 including at least one dry dye of a second type for a liquid, and third portion 310 lacking at least one dry dye for a liquid. Absorbent structure 3I may be used to simultaneously, but separately, stain one or more components of the polar liquid with separate dye first portion 340 and second portion 345, followed by removing excess dye in portion 310 prior to migrating the polar liquid into the tapered internal chamber.

Figure 3J:
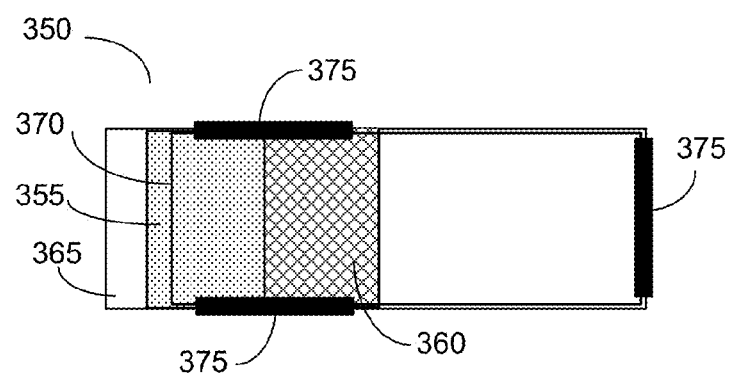
FIG. 3J is a schematic of a top view a microfluidic microscopy device including an absorbent structure with a first portion including a dry dye of a first type for a liquid and a second portion including a dry dye of a second type for a liquid.

FIG. 3J is a top-view schematic of a microfluidic microscopy device. Device 350 includes an absorbent structure with first portion 355 including at least one dry dye of a first type for a liquid and second portion 360 including at least one dry dye of a second type for a liquid. Device 350 further includes support structure 365, lid structure 370, and clamping structure 375. Clamping structure 375 is positioned to maintain a relative position of support structure 365 and lid structure 370 to form a tapered internal chamber adjacent to the second end of the second portion 360 of the absorbent structure, the tapered internal chamber including an internal surface of a second end region of support structure 365 facing an internal surface of a second end region of lid structure 370, the tapered internal chamber including an outflow region.

Incorporation of Dye into Absorbent Structure

In an aspect, the at least one dry dye is incorporated into the absorbent structure by soaking at least a portion of the absorbent structure in a solution containing the at least one dry dye for a liquid. In an aspect, at least a portion of the absorbent structure is treated with a solution containing the at least one dye, the solvent portion of the solution removed by evaporation, resulting in the at least one dry dye left associated with the absorbent structure. For example, at least a portion of the absorbent structure may be soaked in a solution containing acridine orange dissolved in ethanol and left to dry. For example, at least a portion of the absorbent structure may be soaked in a commercially available dye solution, e.g., a ready to use Wright-Giemsa stain (from, e.g., Polysciences, Inc., Warrington, Pa.). In some embodiments, the solvent portion of the solution can include an aqueous liquid, e.g., water. In some embodiments, the solvent portion of the solution can include an organic solvent, e.g., ethanol, methanol, or other organic solvent. In some embodiments, the organic solvent can include dimethylsulfoxide (DMSO) or dimethylformamide (DMF). In an aspect, the choice of solvent for the dye solution will in part be dependent upon the solubility of a given dye in a chosen solvent, i.e., some chemical dyes are more or less soluble in aqueous solution. In some embodiments, the choice of solvent for the dye solution may be dependent upon how rapidly the solvent needs to be removed during the manufacturing process. For example, ethanol or methanol will be more rapidly evaporated than water from the absorbent structure.

In an aspect, the at least one dry dye is printed onto the absorbent structure. For example, the at least one dry dye is printed onto the absorbent structure using an ink jet printer. In an aspect, the at least one dry dye is printed in a pattern onto the absorbent structure. In an aspect, two or more dyes are printed in a pattern onto the absorbent structure. For example, the at least one dry dye for a liquid, e.g., a fluorescing dye, can be printed onto the absorbent structure, e.g., filter paper or nitrocellulose, using a piezoelectric noncontact printer (e.g., SciFLEXARRAYER S3, Scienion AG, Berlin Germany). In general, See, e.g., Fridley et al. (2012) "Controlled release of dry reagents in porous media for tunable temporal spatial distribution upon rehydration" Lab Chip 12:4321-4327, which is incorporated herein by reference.

Other Agents Incorporated into the Absorbent Structure

In some embodiments, one or more additional agents may be incorporated into the absorbent structure. In an aspect, the one or more additional agents include one or more agents configured to maintain the stability of the polar liquid as it migrates through the absorbent structure and the at least one dry dye for a liquid, non-limiting examples of which include an anti-coagulant, a buffer, a permeabilizer, or a fixative. In an aspect, the one or more additional agents include one or more agents to improve the solubility or rehydration of the at least one dry dye for a liquid in the polar liquid. In an aspect, the one or more additional agents include one or more agents intended to modify the flow rate of the polar liquid.

In an aspect, one or more anti-coagulants are incorporated into the absorbent structure to minimize clotting of a blood sample as it migrates from the first end of the absorbent structure to the second end of the absorbent structure. For example, at least a portion of the absorbent structure can include the anti-coagulant EDTA (ethylenediaminetetraacetic acid). Other non-limiting examples of anti-coagulants include heparin, citric acid monohydrate, dextrose monohydrate, sodium phosphate dihydrate, or adenine.

In an aspect, the one or more other agents can include an agent to maintain or alter the pH of the polar liquid to facilitate efficient staining of one or more cellular components in the polar liquid. For example, the one or more other agents can include a buffering agent, e.g., phosphate buffered saline, a dried form of which is solubilized or rehydrated in the presence of the polar liquid. In an aspect, the one or more other agents can include one or more agents configured to permeabilize or fix one or more cellular components of the polar liquid. For example, the one or more agents can include one or more mild detergents, e.g., Triton X-100. For example, the one or more agent can include one or more cross-linking agents, e.g., formaldehyde or paraformaldehyde.

In an aspect, the one or more other agents can include an agent to improve the solubility or rehydration of the at least one dry dye for a liquid in the polar liquid. For example, the one or more other agents can include one or more of a salt, a buffer, or a surfactant. For example, the one or more agents can include cyclodextrins or polyethylene glycol (PEG) complexed with the at least one dry dye for a liquid. For example, the one or more other agents can include serum albumin, sucrose, trehalose, or other agents that increase the viscosity of the polar liquid and increase the efficiency of dissolution of the dried dye. See, e.g., Fridley et al. (2012) "Controlled release of dry reagents in porous media for tunable temporal spatial distribution upon rehydration" Lab Chip 12:4321-4327, which is incorporated herein by reference.

In an aspect, the one or more other agents can include agents that modulate the flow of the polar liquid through the absorbent material. In an aspect, the one or more other agents can include one or more agents configured to alter the viscosity of the polar liquid, e.g., sucrose. In an aspect, the sucrose can be patterned onto the absorbent structure to modulate flow and/or rehydration time of the at least one dry dye for a liquid. See, e.g., Fridley et al. (2012) "Controlled release of dry reagents in porous media for tunable temporal spatial distribution upon rehydration" Lab Chip 12:4321-4327, which is incorporated herein by reference.

In an aspect, the one or more other agents are incorporated into the absorbent structure by soaking at least a portion of the absorbent structure in a solution containing the one or more other agents. In some embodiments, the one or more other agents are included in a solution including the at least one dry dye for a liquid. In some embodiments, the one or more other agents are applied separately. In some embodiments the one or more other agents are incorporated into a first portion of the absorbent structure while the at least one dry dye for a liquid is incorporated into a second portion of the absorbent structure. For example, an anti-coagulant may be incorporated into a first portion of the absorbent structure and a fluorescent dye, e.g., acridine orange, incorporated into a second portion of the absorbent structure such that a liquid sample, i.e., a blood sample, is treated with the anti-coagulant prior to staining with the fluorescent dye. In an aspect, the one or more other agents are printed onto the absorbent structure with, for example, an ink-jet type of printer.

Emergent Points of Flow

In an aspect, the second end of the absorbent structure can have a linear edge, e.g., perpendicular to the flow of polar liquid through the microfluidic microscopy device. In an aspect, the second end of the absorbent structure can include a non-linear edge. In an aspect, the rate of flow from the second end of the absorbent structure into the tapered internal chamber is dependent upon the number of emergent flow points. In an aspect, the emergent flow point from the second end of the absorbent structure creates a "capillary tubule" through which subsequent flow of the polar liquid into the tapered internal chamber progresses. In an aspect, the second end of the absorbent structure includes one emergent flow point, e.g., a point from which the polar liquid emerges from the second end of the absorbent structure and into the adjacent tapered internal chamber. In an aspect, the second end of the absorbent structure includes two or more emergent flow points, e.g., two or more points from which the polar liquid emerges from the second end of the absorbent structure and into the adjacent tapered internal chamber. In an aspect, the flow rate into the tapered internal chamber can be sped up or slowed down by modulating the number of emergent flow points.

Figure 4A:
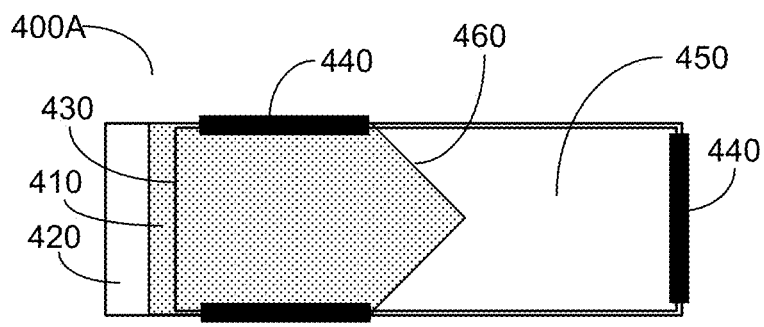
FIG. 4A is a schematic of a top view of a microfluidic microscopy device including a linear edge at the second end of an absorbent structure.
Figure 4B:
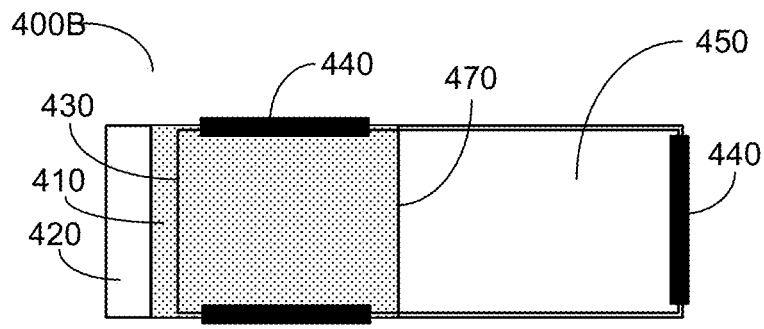
FIG. 4B is a schematic of a top view of a microfluidic microscopy device including an embodiment of a non-linear edge at the second end of an absorbent structure.
Figure 4C:
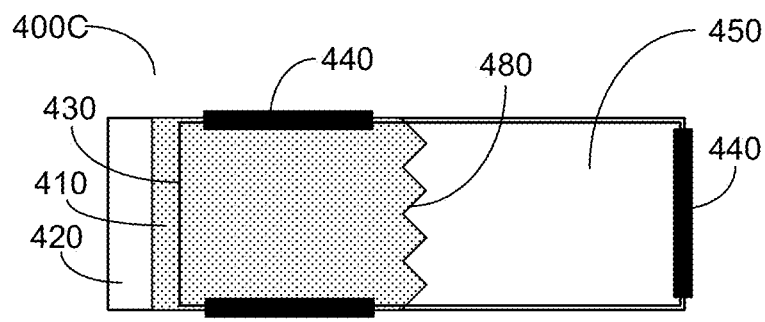
FIG. 4C is a schematic of a top view of a microfluidic microscopy device including an embodiment of a non-linear edge at the second end of an absorbent structure.
Figure 4D:
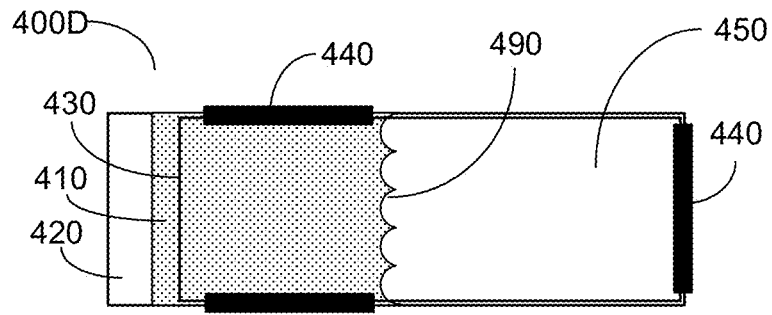
FIG. 4D is a schematic of a top view of a microfluidic microscopy device including an embodiment of a non-linear edge at the second end of an absorbent structure.

In an aspect, the number of emergent flow points is determined by the shape of the absorbent structure at the second end. FIGS. 4A-4D illustrates non-limiting embodiments of microfluidic microscopy devices including one or more emergent flow points based on the shape of the second end of the absorbent structure. Each device shown in FIGS. 4A-4D include absorbent structure 410, support structure 420, lid structure 430, and clamping structure 440. Absorbent structure 410 includes a hydrophilic region configured to convey a polar liquid from a first end to a second end of absorbent structure 410. In an aspect, absorbent structure 410 includes at least one dry dye for a liquid, absorbent structure 410 configured to convey the polar liquid from a first end to a second end of absorbent structure 410 through the at least one dry dye for a liquid. Clamping structure 440 is positioned to maintain a relative position of support structure 420 and lid structure 430 to form tapered internal chamber 450 (shown here from top view). FIG. 4A is a schematic of device 400A including absorbent structure 460 with a non-linear edge creating a single emergent point of flow. FIG. 4B is a schematic of device 400B including absorbent structure 410 with linear edge 470 perpendicular to the flow path from the first end of absorbent structure 410 to the second end of absorbent structure. Linear edge 470 creates at least one emergent flow path on one or both side edges of absorbent structure 410 (see FIG. 20B for a photographic example). FIGS. 4C and 4D include devices 400C and 400D with absorbent structure 410 with respective non-linear edges 480 and 490. Non-linear edges 480 and 490 include multiple possible emergent flow points from absorbent structure 410 into tapered internal chamber 450.

Support and Lid Structures

Returning to FIG. 2A, device 100 includes support structure 115 positioned adjacent to a first surface of absorbent structure 105 and lid structure 120 positioned adjacent to a second surface of absorbent structure 105. In an aspect, absorbent structure 105 forms a thin flat layer between a thin rigid support structure 115 and a thin non-rigid lid structure 120.

In an aspect, support structure 115 has a two-dimensional shape in plan view. In an aspect, support structure 115 has a thin, flat shape, e.g., a thin, rectangular shape. In an aspect, the support structure is about 0.2 mm to about 3.0 mm thick. For example, the support structure is 0.2 mm, 0.3 mm, 0.4 mm, 0.5 mm, 0.6 mm, 0.7 mm, 0.8 mm, 0.9 mm, 1.0 mm. 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.4 mm, 2.6 mm, 2.8 mm, 3.0 mm, 3.5 mm, 4.0 mm, 4.5 mm, 5.0 mm. In an aspect, the support structure is about 1.0 to about 1.2 mm thick. In an aspect, the support structure has a shape that defines the overall planar shape, e.g., length and width, of the device and is compatible for use with a microscope stage. For example, the support structure may include a shape compatible for use with a typical slide holder associated with a mechanically adjustable microscope stage. For example, the support structure may have a shape compatible for use with a microscope stage that includes one or more clips to hold the device on the microscope stage. In an aspect, the support structure can have a shape similar to a standard microscope slide, typically 75×25 mm with a 1 mm thickness. However, support structures of other dimensions are also contemplated, non-limiting examples of which include 75×38 mm; 75×51 mm; 102×76 mm; 102×83 mm; 127×102 mm; 152×114 mm; and 178×127 mm (from, e.g., Ted Pella, Inc., Redding, Calif.).

In an aspect, support structure 115 includes an optically transparent material suitable for light microscopy. In an aspect, an optically transparent material is defined as a material through which light can pass with minimal scattering or reflection. For example, light microscopy is dependent upon a light source emitting light through a sample on a microscope slide and into an objective. In general, the resolving power of the light microscopy is dependent upon the amount of light that is able to pass through the sample. In an aspect, the support structure is fabricated from optically transparent glass, non-limiting examples of which include soda line glass or borosilicate glass. For example, the support structure can include a standard borosilicate glass microscope slide (from, e.g., Ted Pella, Inc., Redding, Calif.). In an aspect, the support structure is fabricated from fused silica glass or synthetic quartz glass. For example, the support structure can include a standard sized quartz microscope slide (from, e.g., Ted Pella, Inc., Redding, Calif.). In an aspect, the support structure is fabricated from optically transparent plastic, non-limiting examples of which include vinyl, polyvinylchloride, polystyrene, ultraviolet transmittable acrylic, or Permanox™. For example, the support structure can include an optically transparent polyvinylchloride substrate including a hydrophilic coating as described in U.S. Pat. No. 5,021,129 to Karasawa & Hirohashi titled "Plastic Slides for Microscopes," which is incorporated herein by reference.

In some embodiments, it may not be necessary for both the support structure and the lid structure to be optically transparent. For example, in the instance where the at least one dry dye for a liquid is a fluorescing dye, only one surface of the tapered internal chamber may be required to be optically transparent to facilitate measurement of fluorescence in the chamber. In an aspect, the support structure may include a coating that is not optically transparent but enhances a fluorescent signal. For example, the support structure may include a reflective coating, e.g., an aluminum coating, to enhance fluorescence. See, e.g., Vink et al. (2013) "An automatic vision-based malaria diagnosis system" *J. Microscopy* 250:166-178, which is incorporated herein by reference.

Device 100 further includes lid structure 120 positioned adjacent to a second surface of absorbent material 105. In an aspect, lid structure 120 is a semi-rigid or deformable material, e.g., a flat thin sheet of non-rigid glass or plastic, allowing for a slight bend in lid structure 120 when held together with support structure 115 and absorbent structure 105 with clasping structure 125 to form tapered internal chamber 130. In an aspect, lid structure 120 is about 0.05 mm to about 5 mm thick. In an aspect, lid structure 120 is about 0.1 mm to about 0.5 mm thick. For example, lid structure 120 can be 0.05 mm, 0.06 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, 1.0 mm, 1.5 mm, 2.0 mm, 2.5 mm, 3.0 mm, 3.5 mm, 4.0 mm, 4.5 mm, or 5.0 mm thick.

In some embodiments, the lid structure is more flexible than the support structure so that at least one external surface, i.e., the support structure, of the device remains flat. For example, the lid structure may be deformable up to about 90 degrees. For example, the lid structure may be deformable by greater than 0 degrees but less than 1 degree. For example, the lid structure may be deformable by 1 degree, 2 degrees, 3 degrees, 4 degrees, 5 degrees, 6 degrees, 7 degrees, 8 degrees, 9 degrees, 10 degrees, 15 degrees, 20 degrees, 25 degrees, 30 degrees, 35 degrees, 40 degrees, 45 degrees, 50 degrees, 60 degrees, 70 degrees, 80 degrees, 90 degrees. In some embodiments, the degree to which the lid structure is flexed is dependent upon the thickness of the absorbent structure and the desired size of the tapered internal chamber.

In an aspect, lid structure 120 is fabricated from optically transparent glass, non-limiting examples of which include soda lime glass or borosilicate glass. In an aspect, the lid structure is fabricated from fused silica glass or synthetic quartz glass. For example, the lid structure can include a glass coverslip sized to cover at least a portion of the second surface of the absorbent structure and with a thickness of about 0.10 mm to 0.5 mm. Glass coverslips suitable for microscopy and of various sizes are commercially available (from, e.g., Ted Pella, Inc., Redding, Calif.). In an aspect, the lid structure includes optically transparent fused quartz. For example, the lid structure can include a 22×22×0.25 mm thick quartz coverslip (from, e.g., Ted Pella, Inc. Redding, Calif.). In an aspect, the lid structure includes optically transparent plastic. Non-limiting examples of optical quality plastic include polystyrene, polyvinylchloride, ultraviolet transmittable acrylic, Thermanoz™, or Permanox™ For example, the lid structure can include a thin non-rigid polyvinylchloride coverslip (from, e.g., Ted Pella, Inc., Redding Calif.).

In an aspect, the support structure and/or the lid structure includes a polymer, e.g., transparent optically transparent polymers like polymethylmethacrylate, polystyrene, polycarbonante, cyclo-olefin(co)polymer, polyesters, polyurethanes, and the like.

In an aspect, support structure 115 and lid structure 120 are constructed of the same material. For example, support structure 115 and lid structure 120 can both be constructed of thin pieces of glass or plastic sized for use on a microscope stage. In an aspect, support structure 115 and lid structure 120 include different materials. For example, support structure 115 may include a plastic, optically transparent or otherwise while lid structure 120 includes a thin piece of optically transparent glass. In an aspect, only a portion of either support structure 115 or lid structure 120 is fabricated from an optically transparent material. For example, in some embodiments, only those portions of the support structure and/or the lid structure involved in forming the tapered internal chamber are optically transparent and suitable for microscopy or other optical detection method.

In an aspect, the surface of the support structure and/or the lid structure includes a hydrophilic surface. In an aspect, the hydrophilic surface promotes spreading of a polar liquid into tapered internal chamber 130. In an aspect, the hydrophilic surface properties of the support structure and/or the lid structure are a function of the water contact angle, wherein the lower the water contact angle, the higher the hydrophilicity. In an aspect, a hydrophilic (or hydrophobic) property of a surface of the support structure and/or the lid structure can be defined based on the geometry of a water droplet on the surface, specifically the water contact angle between a droplet's edge and the surface underneath it. If the droplet spreads, the contact angle is less than 90 degrees and the surface is considered to be hydrophilic. If the droplet remains beaded-up on the surface, the contact angle is more than 90 degrees and the surface is considered to be hydrophobic. In an aspect, the surface chemistry of the support structure and/or the lid structure can be modified to increase hydrophilic or hydrophobic properties.

In an aspect, the hydrophilic surface is an inherent property of the material used to fabricate the support structure and/or the lid structure. In an aspect, the hydrophilic surface is generated using a plasma, corona, or ozone treatment. In an aspect, the hydrophilic surface is generated by applying a hydrophilic coating to a surface of the support structure and/or the lid structure. For example, at least a portion of the surface of the support structure and/or the lid structure can be treated with HydroLAST™ (from, e.g., AST Products, Inc., Billerica, Mass.). In an aspect, a surface of the support structure and/or the lid structure can be treated with hydrophilic polymers including carboxyl, hydroxyl, or amine functionalities that serve to loosely bind water. In an aspect, the hydrophilic polymers include ultra-high molecular weight polyethylene. See, e.g., U.S. Pat. No. 5,700,559 to Sheu & Loh titled "Durable Hydrophilic Surface Coatings," which is incorporated herein by reference. Other non-limiting examples of polymers for creating a hydrophilic surface include polyvinylpyrolidone (PVP), polyurethanes, polyacrylic acid (PPA), polyethylene oxide (PEO), and polysaccharide. In an aspect, at least a portion of the surface of the lid structure and the support structure are hydrophilic. In an aspect, only a portion of the internal surface of the second end region of the support structure and/or a portion of the internal surface of the second end region of the lid structure is hydrophilic. In an aspect, the hydrophilicity of the internal surface of the second end region of the support structure and/or the internal surface of the second end region of the lid structure promotes flow of the polar liquid from the second end of the absorbent structure and into the tapered internal chamber. In an aspect, the hydrophilicity of the one or more internal surfaces of the tapered internal chamber draws the polar liquid from the second end of the absorbent structure into the tapered internal chamber.

Clamping Structure

The microfluidic microscopy device of FIG. 2A includes clamping structure 125 positioned to maintain a relative position of the support structure and the lid structure to form the tapered internal chamber adjacent to the second end of the absorbent structure. FIGS. 5A-5C illustrate further aspects of a clamping structure. FIG. 5A illustrates a top view and a cross-sectional view of microfluidic microscopy device 100, such as described in FIGS. 1 and 2, with clamping structure 500. In the top view, clamping structure 500 is shown positioned along the edges of the device 100. In an embodiment clamping structure 500 includes a pinching or spring loaded clamping structure, e.g., binder clips. FIG. 5B illustrates a top view and a cross-sectional view of microfluidic microscopy device 100 with clamping structure 510. In the top view, clamping structure 510 is shown positioned along the edges of the device 100. In an aspect, clamping structure 510 extends along the entirety of the edges of device 100. In an embodiment, clamping structure 510 includes a sliding binding bar configured to slide along the external surfaces of the support structure and the lid structure. For example, clamping structure 510 can include a plastic or metallic sliding bar. FIG. 5C illustrates a top view and a cross-sectional view of microfluidic microscopy device 100 with clamping structure 520. In an aspect, clamping structure 520 includes a wrap-around structure that fits around three edges of device 100. For example, clamping structure 520 can include a piece of form fitting rubber, plastic or polyvinylchloride edge trim that covers the edge of the support structure and the lid structure. For example, a rubber clamping structure, e.g., a rubber seal, for wrapping around three sides of the device may be manufactured using a U-channel extrusion process (from, e.g., Western Rubber & Supply, Inc., Livermore, Calif.).

In some embodiments, the support structure and the lid structure are joined permanently using heat or an adhesive. For example, a plastic support structure and a plastic lid structure can be welded together around an absorbent structure using a heat source, e.g., a laser welder or a plastic welding gun (from, e.g., U.S. Plastic Corp., Lima, Ohio). For example, the support structure and the lid structure can be maintained in a relative position around the absorbent structure to form the tapered internal chamber using an optically transparent adhesive (from, e.g., 3M, St. Paul, Minn.). In an aspect, the support structure and the lid structure snap together around the absorbent structure, the support structure and the lid structure including some form of coupling means, e.g., holes and matching pins, to facilitate a snap closure.

Reservoir Structures

In an aspect, the microfluidic microscopy device includes a region at its first end that includes a sample reservoir. In an aspect, the sample reservoir is configured to hold at least a volume of polar liquid sufficient to fill the absorbent structure and the tapered internal chamber. In an aspect, the volume of polar liquid sufficient to fill the absorbent structure and the tapered internal chamber is dependent upon the dimensions and volume capacity of the absorbent structure and the tapered internal chamber. In an aspect, the volume of polar liquid includes 1-3 drops of polar liquid. For example, the volume of polar liquid, e.g., blood, can include 1-3 drops of blood from a finger stick. In an aspect, the volume of polar liquid is greater than 1 microliter and less than 1000 microliters. In an aspect, the volume of polar liquid is greater than 50 microliters and less than 500 microliters. For example, in some embodiments, the volume of polar liquid is 1 microliter, 5 microliters, 10 microliters, 20 microliters, 30 microliters, 40 microliters, 50 microliters, 60 microliters, 70 microliters, 80 microliters, 90 microliters, 100 microliters, 120 microliters, 140 microliters, 160 microliters, 180 microliters, 200 microliters, 300 microliters, 400 microliters, 500 microliters, 600 microliters, 700 microliters, 800 microliters, 900 microliters, or 1000 microliters. In an aspect, the sample reservoir is in fluid communication with the absorbent structure. In an aspect, the sample reservoir includes the first end of the absorbent structure. In an aspect, the sample reservoir includes a conduit, e.g., a channel, to the first end of the absorbent structure. For example, the sample reservoir may be in fluid communication with the first end of the absorbent structure through one or more capillary channels etch in a surface of the support structure.

Figure 6:
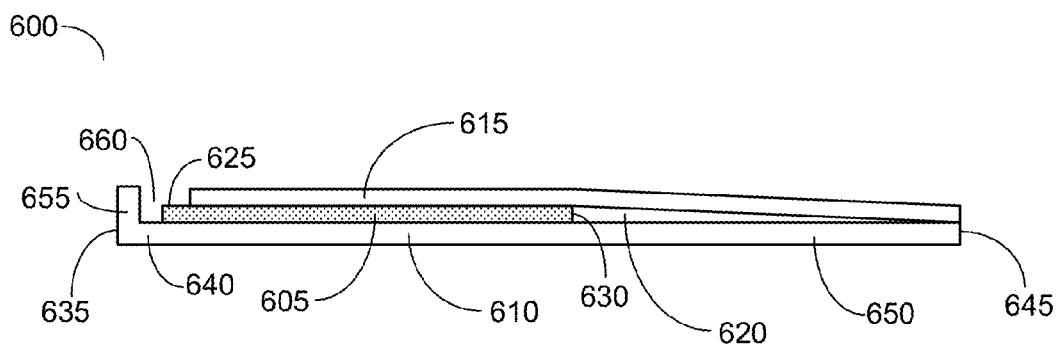
FIG. 6 is a schematic of a cross-section through a microfluidic microscopy device with a sample reservoir.

FIGS. 6-9 illustrate non-limiting embodiments of sample reservoirs incorporated into the microfluidic microscopy device. FIG. 6 is a schematic of a cross-section through microfluidic microscopy device 600. Device 600 includes an absorbent structure 605, a support structure 610, and lid structure 615. A second end region of support structure 610 and a second end region of lid structure 615 form tapered internal chamber 620. Absorbent structure 605 includes first end 625 and second end 630, wherein second end 630 is positioned adjacent to tapered internal chamber 620. Support structure 610 includes first end 635 including first end region 640 and second end 645 including second end region 650. First end region 640 of support structure 610 includes an outward extension 655 from the base of support structure 610 to form sample reservoir 660.

Figure 7:
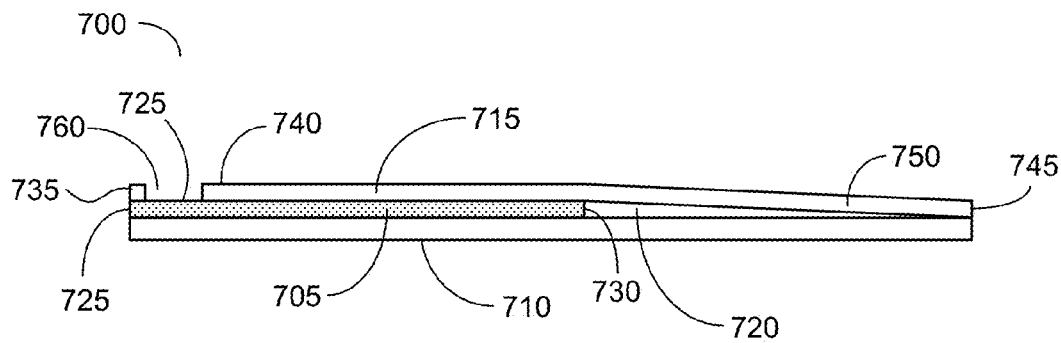
FIG. 7 is a schematic of a cross-section through a microfluidic microscopy device with a sample reservoir.

FIG. 7 is a schematic of a cross-section through microfluidic microscopy device 700. Device 700 includes absorbent structure 705, support structure 710, and lid structure 715. A second end region of support structure 710 and a second end region of lid structure 715 form tapered internal chamber 720. Absorbent structure 705 includes first end 725 and second end 730. Lid structure 715 includes first end 735 including first end region 740 and second end 745 including second end region 750. Lid structure 715 further includes an opening in first end region 740 defining access to sample reservoir 760. Sample reservoir 760 is in fluid communication with underlying absorbent structure 705. In this embodiment, absorbent structure 705 includes a region in proximity to first end 725 that is adjacent to a position adjacent to device 700, e.g., open to the air and accessible for application of a polar liquid. In some embodiments, sample reservoir 760 is in fluid communication with absorbent structure 705 through one or more channels, e.g., one or more capillary channels etched into support structure 710.

Figure 8:
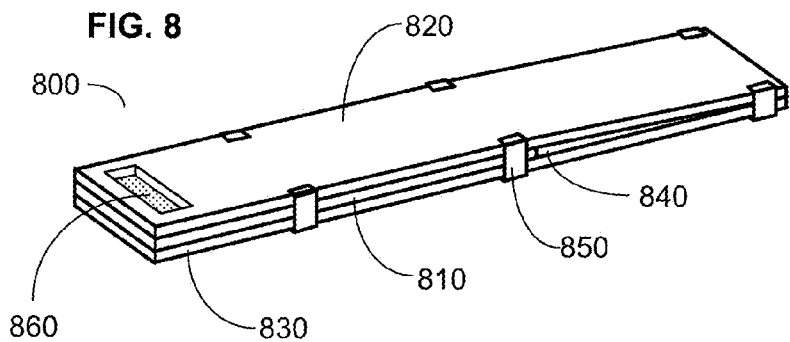
FIG. 8 is a schematic of a microfluidic microscopy device with a sample reservoir.

FIG. 8 is a schematic of a non-limiting embodiment of microfluidic microscopy device 800. Device 800 includes absorbent structure 810 positioned between lid structure 820 and support structure 830. Clamping structure 850 is positioned to maintain a relative position of lid structure 820 and support structure 830 to form tapered internal chamber 840. Lid structure 820 further includes an opening defining access to sample reservoir 860. Sample reservoir 860 is in fluid communication with underlying absorbent structure 810. In this embodiment, absorbent structure 810 includes a region at the first end that is adjacent to a position adjacent to device 800, e.g., open to the air and accessible for application of a polar liquid. In some embodiments, absorbent structure 810 is completely covered by lid structure 820 and support structure 830 and not open to a position adjacent to the device, i.e., the absorbent structure is not available for direct application of the polar liquid but receives the polar liquid from a sample reservoir. For example, the polar liquid may be added to a sample reservoir at the first end of the microfluidic microscopy device from which the polar liquid flows through one or more fluid channels to the first end of the absorbent structure.

Figure 9:
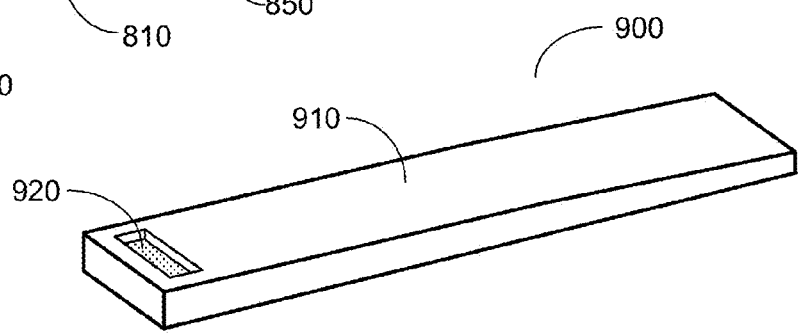
FIG. 9 is a schematic of a microfluidic microscopy device with a sample reservoir.

FIG. 9 is a schematic of a non-limiting embodiment of microfluidic microscopy device 900 including a sample reservoir. In this embodiment, the absorbent structure and the tapered internal chamber are completely enclosed with a housing structure 910. One surface of housing structure 910 includes sample reservoir 920 formed from an opening in housing structure 910 and allowing an internal absorbent structure to be open to a position adjacent to device 900, e.g., open to the air and accessible for application of a polar liquid to a surface of the absorbent structure or to a position adjacent to and in fluid communication with the absorbent structure.

Hydrophobic Region on Support and/or Lid Structures

In an aspect, a microfluidic microscopy device includes one or more hydrophobic regions on the internal surface of the second end region of the support structure and/or the lid structure. In an aspect, the one or more hydrophobic regions are configured to control the flow of polar liquid into the tapered internal chamber. In an aspect, the one or more hydrophobic regions are configured to control outflow or venting of air pushed out of the tapered internal chamber by the incoming polar fluid. In an aspect, the one or more hydrophobic regions include one or more hydrophobic guides for guiding air out of the tapered internal chamber as the polar liquid is filling the tapered internal chamber. In some embodiments, the hydrophobic regions are positioned along the edges of the support structure and/or the lid structure. In an aspect, the hydrophobic regions are positioned along the edges of the internal surfaces of the support structure and/or lid structure forming the tapered internal chamber. In an aspect, the hydrophobic regions positioned along the edges of the tapered internal chamber allow for the passage of air but create a barrier to the flow of polar liquid.

In an aspect, the one or more hydrophobic regions include one or more hydrophobic materials applied to one or more surfaces of the support structure and/or the lid structure. In an aspect, the one or more hydrophobic regions include one or more hydrophobic materials that increase the water contact angle, preferably to greater than 90 degrees. In an aspect, the one or more hydrophobic materials include one or more non-polar materials, non-limiting examples of which include waxes, oils, silicones, fluorocarbons, or fats. Other non-limiting examples of hydrophobic materials include silanes, including fluoroalkylsilanes, phenyl silanes, and chlorosilanes; nylon, alkyl ketene dimers, polydimethylsiloxane, polyethylene, polychlorotrifluoroethylene, polypropylene, poly t-butyl methacrylate, fluorinated ethylene propylene, hexatriacontane, polytetrafluoroethylene, poly (hexafluoropropylene) and polyisobutylene. See, e.g., U.S. Pat. No. 7,282,241 to Kim & Miller titled "Patterned, high surface area substrate with hydrophilic/hydrophobic contrast, and method of use," which is incorporated herein by reference.

In an aspect, the one or more hydrophobic regions are added to at least a portion of the internal surface of the second end region of the support structure and/or the internal surface of the second end region of the lid structure using any of a number of fabrication methods, non-limiting examples of which include photolithography, plotting, ink jet etching, plasma treatment, wax printing, ink jet printing, flexography printing, screen printing, or laser treatment. See, e.g., Li et al. (2012) "A perspective on paper-based microfluidics: Current status and future trends" *Biomicrofluidic* 6:011301, which is incorporated herein by reference.

Figure 10A:
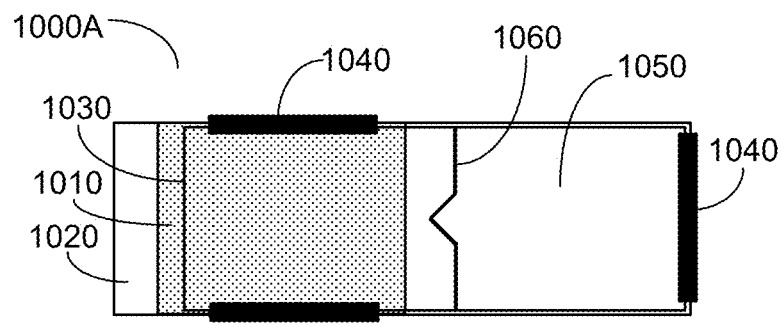
FIG. 10A is a schematic of a top view of a microfluidic microscopy device with a patterned hydrophobic region.
Figure 10B:
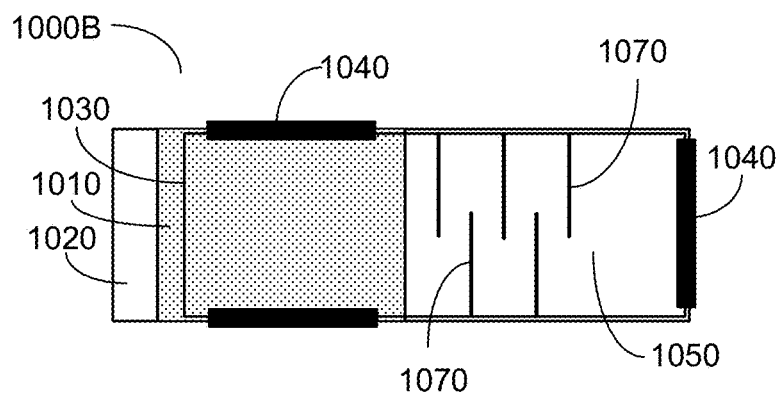
FIG. 10B is a schematic of a top view of a microfluidic microscopy device with a patterned hydrophobic region.
Figure 10C:
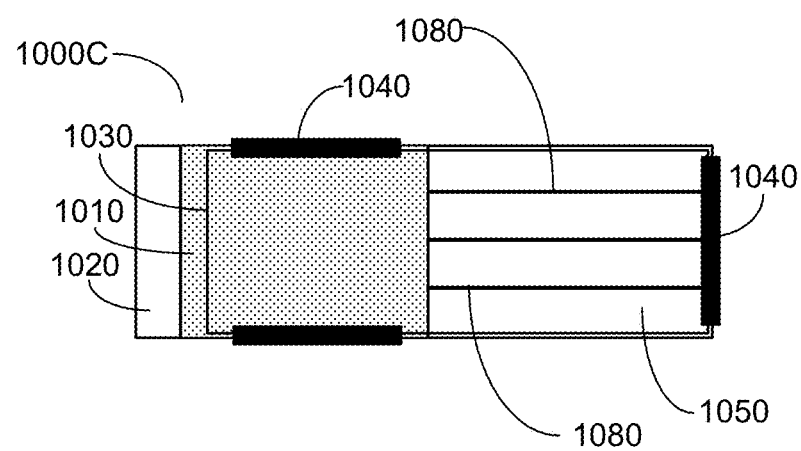
FIG. 10C is a schematic of a top view of a microfluidic microscopy device with a patterned hydrophobic region.

In some embodiments, the hydrophobic regions are patterned on one or more of the internal surfaces forming the tapered internal chamber. In an aspect, the one more hydrophobic regions are configured to channel the flow of polar liquid. See, e.g., U.S. Patent Application 2012/0097272 to Vulto et al. titled "Phaseguide patterns for liquid manipulation," which is incorporated herein by reference. In an aspect, the one or more hydrophobic regions are configured to channel air trapped within the tapered internal channel towards an outer unsealed edge of the tapered internal channel as the tapered internal chamber is being filled with the polar liquid. FIGS. 10A-10C show top view schematics of a microfluidic microscopy device with non-limiting examples of patterns for the hydrophobic regions. In each of FIGS. 10A-10C, the microfluidic microscopy device includes support structure 1020 positioned adjacent to a first surface adjacent of absorbent structure 1010 and lid structure 1030 positioned adjacent to a second surface of absorbent structure 1010. Clamping structure 1040 is positioned to maintain a relative position of support structure 1020 and lid structure 1030 to form tapered internal chamber 1050 (seen from the top) adjacent to the second end of absorbent structure 1010. Tapered internal chamber 1050 includes an internal surface of a second end region of support structure 1020 facing an internal surface of a second end region of lid structure 1030.

In FIG. 10A, device 1000A includes hydrophobic pattern 1060 patterned on the internal surface of the second end region of support structure 1020 and/or on the internal surface of the second end region of lid structure 1030. In this configuration, hydrophobic pattern 1060 acts as a "phaseguide" to direct flow of air towards the outer edges of tapered internal chamber 1050 as the chamber is being filled with polar liquid from absorbent structure 1010. In FIG. 10B, device 1000B includes hydrophobic pattern 1070 patterned on the internal surface of the second end region of support structure 1020 and/or on the internal surface of the second end region of lid structure 1030. Hydrophobic pattern 1070 includes a series of lines perpendicular to the flow of polar fluid into tapered internal chamber 1050. In this configuration, hydrophobic pattern 1070 acts as a "phaseguide" to direct flow of air towards the outer edges of tapered internal chamber 1050 as the chamber is being filled with polar liquid from absorbent structure 1010. In FIG. 10C, device 1000C includes hydrophobic pattern 1080 patterned on the internal surface of the second end region of support structure 1020 and/or on the internal surface of the second end region of lid structure 1030. Hydrophobic pattern 1080 includes a series of lines parallel to the flow of polar fluid into tapered internal chamber 1050. In this configuration, hydrophobic pattern 1080 acts as a "phaseguide" to direct flow of air towards the end edge of tapered internal chamber 1050 as the chamber is being filled with polar liquid from absorbent structure 1010.

In an aspect, a microfluidic microscopy device includes an absorbent structure with a first end and a second end, the absorbent structure including an interior hydrophilic region with at least one dry dye for a liquid, the absorbent structure configured to convey a polar liquid from the first end of the absorbent structure through the interior hydrophilic region and the at least one dry dye for a liquid to the second end of the absorbent structure; a support structure positioned adjacent to a first surface of the absorbent structure, the support structure including a first end and a second end, the second end of the support structure including a second end region positioned adjacent to the second end of the absorbent structure; a lid structure positioned adjacent to a second surface of the absorbent structure, the lid structure including a first end and a second end, the second end of the lid structure projecting beyond the second end of the absorbent structure, the second end of the lid structure including a second end region positioned adjacent to the second end of the absorbent structure and overlapping with the second end region of the support structure; a clamping structure positioned to maintain a relative position of the support structure and the lid structure to form a tapered internal chamber adjacent to the second end of the absorbent structure, the tapered internal chamber including an internal surface of the second end region of the support structure facing an internal surface of the second end region of the lid structure; and an interior hydrophobic region positioned adjacent to the interior hydrophilic region of the absorbent structure, a first end of the interior hydrophobic region extending beyond the first end of the lid structure and open to a position adjacent to the device and a second end of the interior hydrophobic region positioned adjacent to the tapered internal chamber.

Figure 11A:
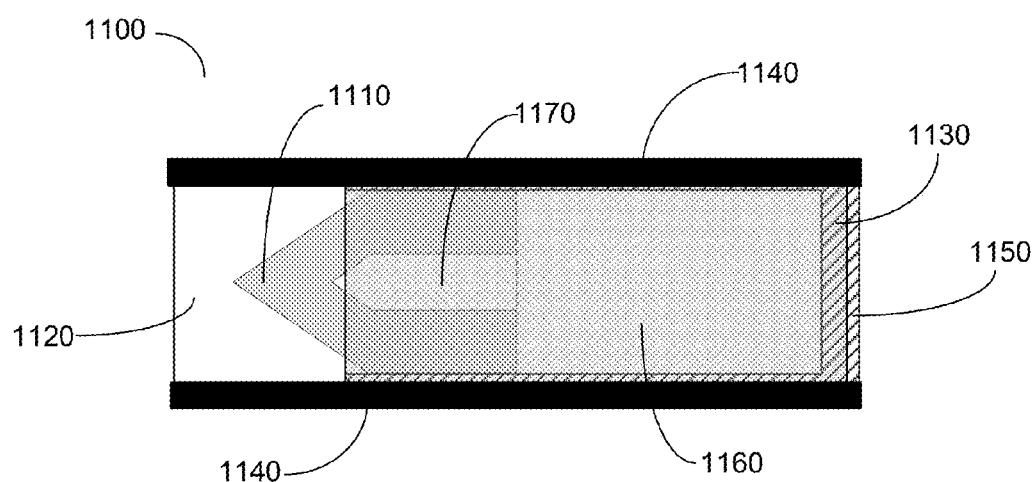
FIG. 11A is a schematic of a top view of a microfluidic microscopy device.
Figure 11B:
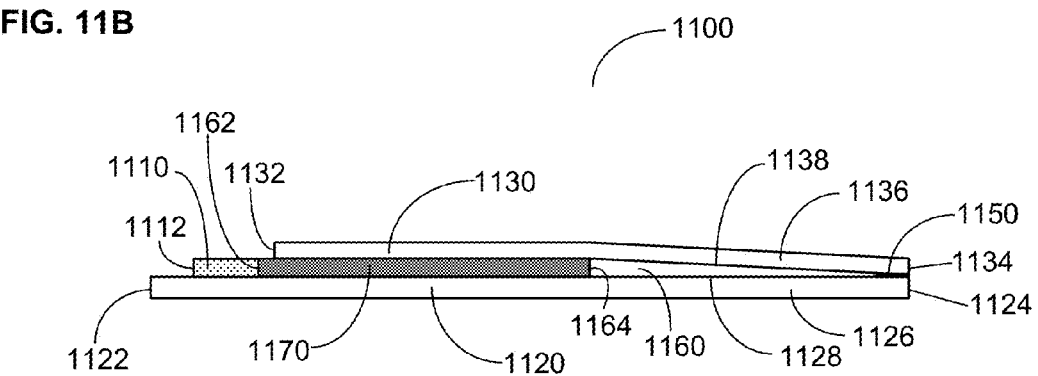
FIG. 11B is a schematic of a cross-sectional view of a microfluidic microscopy device.

FIGS. 11A and 11B illustrate aspects of an embodiment of a microfluidic microscopy device including an interior hydrophobic region configured to vent air from a tapered internal chamber during the liquid filling process. FIG. 11A is a top-view of a schematic of device 1100. Device 1100 includes absorbent structure 1110, support structure 1120, lid structure 1130, and clamping structure 1140. Absorbent structure 1110 includes at least one dry dye for a liquid. Support structure 1120 and lid structure 1130 are positioned adjacent to opposite surfaces of absorbent structure 1110. Device 1100 further includes hydrophobic region 1150 patterned around the edges of support structure 1120 and/or lid structure 1130. Hydrophobic region 1150 forms a barrier preventing the leakage of a polar liquid from device 1100. Clamping structure 1140 is positioned to maintain a relative position of support structure 1120 and lid structure 1130 to form tapered internal chamber 1160 adjacent to the second end of absorbent structure 1110. Device 1100 further includes interior hydrophobic region 1170 positioned adjacent to an interior hydrophilic region of absorbent structure 1110. Interior hydrophobic region 1170 is configured to vent air from tapered internal chamber 1160 during filling with a polar liquid.

FIG. 11B is a schematic of a cross-sectional view through device 1110 including a cross-sectional view through interior hydrophobic region 1170. Device 1100 includes absorbent structure 1110, support structure 1120, and lid structure 1130. Absorbent structure 1110 includes first end 1112. In this view, the second end of absorbent structure 1110 is not shown but is adjacent to tapered internal chamber 1160. Absorbent structure 1110 includes an interior hydrophilic region with at least one dry dye for a liquid. Absorbent structure 1110 is configured to convey a polar liquid from first end 1112 through the interior hydrophilic region and the at least one dry dye for a liquid to the second end of absorbent structure 1110. Support structure 1120 is positioned adjacent to a first surface of absorbent structure 1112 and interior hydrophobic region 1170. Support structure 1120 includes first end 1122 and second end 1124, second end 1124 including second end region 1126 positioned adjacent to second end of absorbent structure 1110. Lid structure 1130 is positioned adjacent to a second surface of absorbent structure 1110 and interior hydrophobic region 1170. Lid structure 1130 includes first end 1132 and second end 1134, second end 1134 of lid structure 1130 projecting beyond second end of absorbent structure 1110. Lid structure 1130 further includes second end region 1136 positioned adjacent to the second end of absorbent structure 1110 and overlapping with second end region 1126 of support structure 1120. Hydrophobic region 1150 forms a hydrophobic barrier at a between second end 1124 of support structure 1120 and second 1134 of lid structure 1130. Clamping structure (not shown in this view) is positioned to maintain a relative position of support structure 1120 and lid structure 1130 to form tapered internal chamber 1160 adjacent to the second end of absorbent structure 1110 and second end 1164 of interior hydrophobic region 1170. Tapered internal chamber 1170 includes internal surface 1128 of second end region 1126 of support structure 1120 facing internal surface 1138 of second end region 1136 of lid structure 1130. Interior hydrophobic region 1170 is positioned adjacent to hydrophilic region of absorbent structure 1110, first end 1162 of interior hydrophobic region 1170 extending beyond first end 1132 of lid structure 1130 and open to a position adjacent to the device and second end 1164 of interior hydrophobic region 1170 positioned adjacent to tapered internal chamber 1160.

In an aspect, the at least one interior hydrophobic region is configured to absorb the polar liquid at a slower rate than the surrounding regions of the absorbent structure. In an aspect, the at least one interior hydrophobic region is configured to allow escape of air moving in front of the polar liquid as it flows through the absorbent material and into the tapered internal chamber. The at least one hydrophobic region includes at least one edge on the second end of the absorbent material.

In an aspect, the interior hydrophobic region is constructed using any of a number of fabrication methods, non-limiting example of which include photolithography, plotting, ink jet etching, plasma treatment, wax printing, ink jet printing, flexography printing, screen printing, or laser treatment. In an aspect, the interior hydrophobic region is generated by physically blocking pores in the absorbent structure using, for example, photoresist and polydimethylsiloxane (PDMS). In an aspect, the interior hydrophobic region is generated by physical deposition of one or more reagents on or into the absorbent structure, for example, paraffin wax or polystyrene. In an aspect, the interior hydrophobic region is generated by chemical modification of the absorbent structure, for example, chemical modification with alkyl ketene dimer (AKD). For example, chemical modification of a cellulose-based absorbent structure can be achieved by applying agents that react with the —OH groups of cellulose, imparting hydrophobicity to the fibers. See, e.g., Li et al. (2012) "A perspective on paper-based microfluidics: Current status and future trends" *Biomicrofluidic* 6:011301, which is incorporated herein by reference. Other non-limiting examples of hydrophobic materials include silanes, including fluoroalkylsilanes, phenyl silanes, and chlorosilanes; nylon, polyethylene, polychlorotrifluoroethylene, polypropylene, poly t-butyl methacrylate, fluorinated ethylene propylene, hexatriacontane, polytetrafluoroethylene, poly(hexafluoropropylene) and polyisobutylene.

In an aspect, the entirety of the absorbent structure undergoes hydrophobization using one or more of the methods described herein followed by selective dehydrophobization to generate the interior hydrophilic regions of the absorbent structure. For example, an absorbent structure, e.g., filter paper, can be uniformly treated with polystyrene, wax or PDMS followed by selective dehydrophobization using an organic solvent to generate specific interior hydrophobic and interior hydrophilic regions filter paper. In an aspect, the absorbent structure undergoes selective hydrophobization to generate the interior hydrophobic regions. For example, chemical modification of the absorbent structure with alkyl ketene dimer cannot be reversed using organic solvents and is instead laid down in a specific pattern, e.g., using a modified ink jet printer.

In an aspect, the interior hydrophobic region is incorporated into the absorbent structure using one or more of the hydrophobic materials and/or methods described herein. In an aspect, the interior hydrophobic region is a separate structure that is integrated adjacent to one or more edges of the absorbent structure. In an aspect, the interior hydrophobic region includes one or more shapes or configurations to promote outflow of air from the tapered internal chamber as the chamber is filled with the polar liquid from the second end of the absorbent structure. In an aspect, the interior hydrophobic region associated with the absorbent structure extends from the second edge of the absorbent structure adjacent to the tapered internal chamber back to a portion of the absorbent structure open to the ambient atmosphere. For example, the interior hydrophobic region can include a first edge extended beyond the first edge of the lid structure and a second edge positioned adjacent to the tapered internal chamber.

Housing Structure

In an aspect, the microfluidic microscopy device includes an absorbent structure and tapered internal chamber fully enclosed in a housing structure to which a polar liquid is added at one end. In an aspect, all or part of the housing structure is optically transparent and suitable for microscopy. For example, all or part of the housing structure can be manufactured from optically transparent plastic. For example, all or part of the housing structure can be manufactured from optically transparent glass.

Figure 12A:
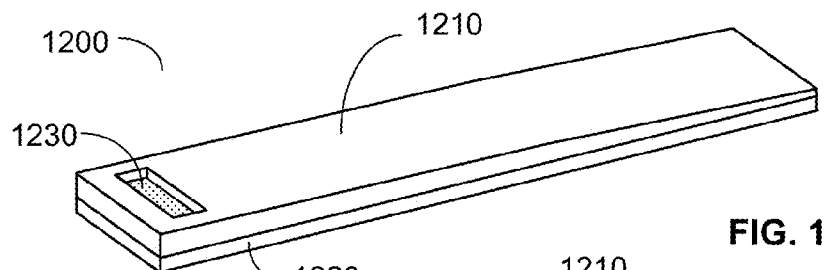
FIG. 12A is a schematic of a microfluidic microscopy device.
Figure 12B:
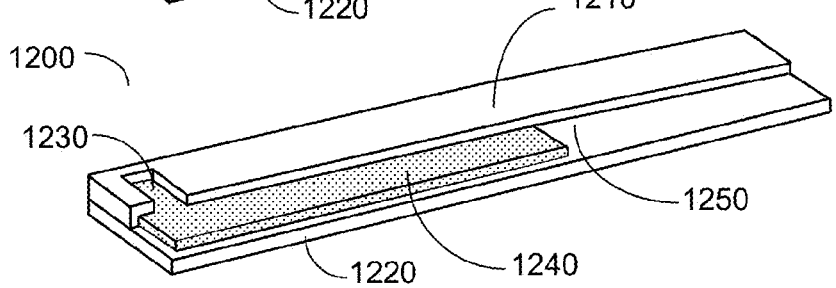
FIG. 12B is a schematic of a cut-away view of a microfluidic microscopy device such as shown in FIG. 12A.

FIGS. 12A and 12B show schematics of an embodiment of a microfluidic microscopy device including a housing structure. FIG. 12A is a schematic of device 1200 including lid structure 1210 and support structure 1220 forming two sides of the housing structure. Lid structure 1210 and support structure 1220 are positioned adjacent to opposite sides of an enclosed absorbent structure. Lid structure 1210 further includes an opening forming a sample reservoir 1230 that allows access to the absorbent structure for application of a polar liquid. Lid structure 1210 and support structure 1220 are sealed together along the edges to form the housing structure. In an aspect, lid structure 1210 and support structure 1220 are glued together along the edges to form the cassette. In an aspect, lid structure 1210 and support structure 1220 are fused together around the absorbent structure to form the housing structure. For example, a plastic lid structure 1210 and a plastic support structure 1220 may be fused together using standard methods. In an aspect, lid structure 1210 and support structure 1220 snap together over the absorbent structure to form the housing structure. FIG. 12B is a schematic of a cut-away view of device 1200. In this view, absorbent structure 1240 is seen positioned between lid structure 1210 and support structure 1220. Also visible is tapered internal chamber 1250 formed from clamping or enclosing absorbent structure 1240 between lid structure 1210 and support structure 1220. At least a portion of lid structure 1210 and/or support structure 1220 is optically transparent, e.g., optically transparent plastic or glass, in the portion forming tapered internal chamber 1250 and suitable for microscopy.

Figure 13A:
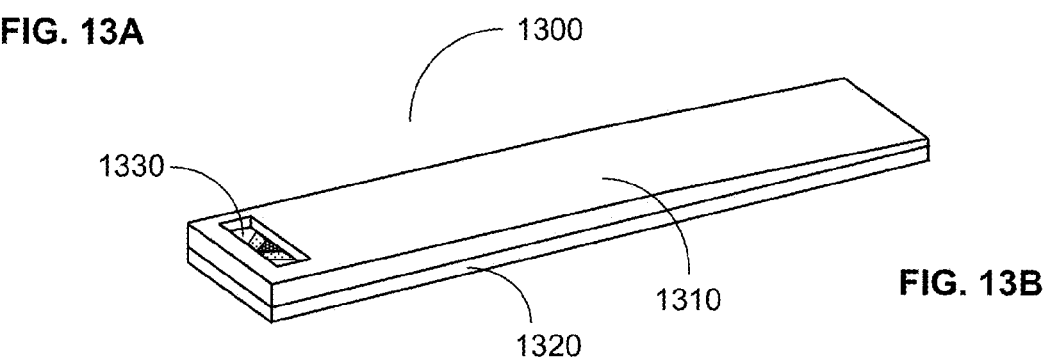
FIG. 13A is a schematic of a microfluidic microscopy device.
Figure 13B:
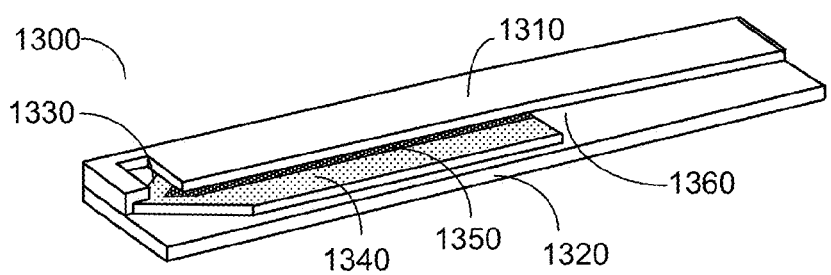
FIG. 13B is a schematic of a cut-away view of a microfluidic microscopy device such as shown in FIG. 13A.

FIGS. 13A and 13B show schematics of another embodiment of a microfluidic microscopy device including an absorbent structure and a tapered internal chamber fully enclosed in a housing structure. Device 1300 includes lid structure 1310 and support structure 1320 forming the housing structure. Lid structure 1310 and support structure 1320 are positioned adjacent to opposite sides of an enclosed absorbent structure. In this example, the absorbent structure is similar to that shown in FIG. 11A and includes an interior hydrophobic region for venting air trapped in the tapered internal chamber formed from an internal surface of lid structure 1310 facing an internal surface of support structure 1320. Lid structure 1310 further includes an opening forming a sample reservoir 1330 that allows access to the absorbent structure for application of a polar liquid. FIG. 13B is a schematic of a cut-away view of device 1300. In this view, absorbent structure 1340 is seen positioned between lid structure 1310 and support structure 1320. Also visible is tapered internal chamber 1360 formed from clamping or enclosing absorbent structure 1340 between lid structure 1310 and support structure 1320. At least a portion of lid structure 1310 and/or support structure 1320 is optically transparent in the portion forming tapered internal chamber 1360 and suitable for microscopy. For example, all or part of lid structure 1310 and/or support structure 1320 can be manufactured from optically transparent plastic. For example, all or part of lid structure 1310 and/or support structure 1320 can be manufactured from optically transparent glass. Also visible is hydrophobic region 1350 with a first end exposed to the outside through sample reservoir 1330 and a second end adjacent to tapered internal chamber 1360. Hydrophobic region 1350 is configured to vent air from tapered internal chamber 1360 back out through sample reservoir 1330 to allow complete filling of tapered internal chamber 1360 with a polar liquid.

Lateral Flow Assay

In an aspect, the microfluidic microscopy device includes a lateral flow assay. In an aspect, a polar liquid is applied to a first end of the microfluidic microscopy device and a first fraction of the polar liquid migrates through an absorbent structure including at least one dry dye for a liquid and a second fraction of the polar liquid migrates through a lateral flow assay. In an aspect, the lateral flow assay is incorporated into the absorbent structure. In an aspect, the lateral flow assay is part of a separate structure that is positioned adjacent to the absorbent structure with access to the flow of applied polar liquid. In an aspect, the at least one lateral flow assay includes one or more reagents for detecting analytes associated with a medical condition. Non-limiting examples of medical conditions include malaria, HIV-AIDS, bacterial infection, tuberculosis, diabetes, kidney dysfunction, blood dysfunction, or other medical conditions. For example, the at least one lateral flow assay can include an immunochromatographic test for malaria, e.g., an immunoassay for *P. falciparum* histidine-rich protein-2 (pfHRP2), and *Plasmodium* spp. lactose dehydrogenase (pLDH). See, e.g., Moody (2002) "Rapid Diagnostic Tests for Malaria Parasites" *Clinical Microbiology Reviews* 15:66-78, which is incorporated herein by reference. Other non-limiting examples of analytes include glucose, protein, nitrite, uric acid, ketones, lactate, pH, human IgG, total iron, pathogenic bacteria, ABO antigens, alkaline phosphates, cholesterol, ascorbic acid, or HIV-1 antigen. In an aspect, the at least one lateral flow assay includes components to produce at least one of a colorimetric readout, an electrochemical readout, a chemiluminescence readout, or an electrochemiluminescence readout. For example, the at least one lateral flow assay can include an immunoassay for gp41, an HIV-1 antigen, that produces an enzymatic or chemical color-change reaction that is visible to the unaided eye. For example, the at least one lateral flow assay can include an immunoassay for rapid blood typing. See, e.g., Al-Tamimi et al. (2012) "Validation of paper-based assay for rapid blood typing" *Anal. Chem.* 84:1661-1668, which is incorporated herein by reference. A recent review of paper-based lateral flow assays is provided by Yetisen et al. (2013) "Paper-based microfluidic point-of-care diagnostic devices" *Lab Chip* 13:2210-2251, which is incorporated herein by reference.

Figure 14:
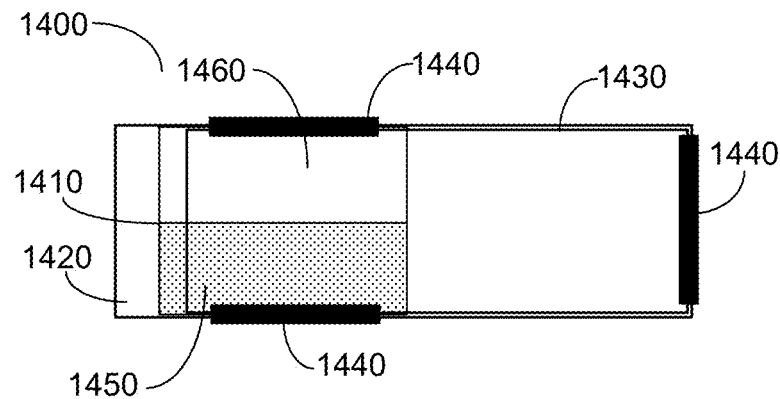
FIG. 14 is a schematic of top view of a microfluidic microscopy device including a lateral flow assay.
Figure 15:
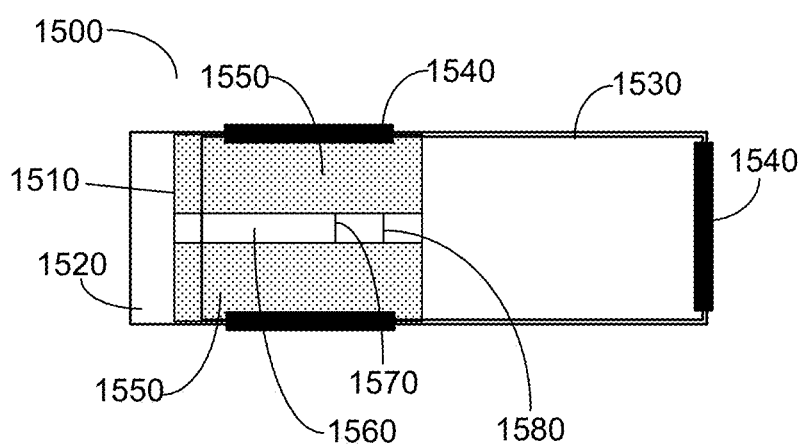
FIG. 15 is a schematic of a top view of a microfluidic microscopy device including a lateral flow assay.
Figure 16:
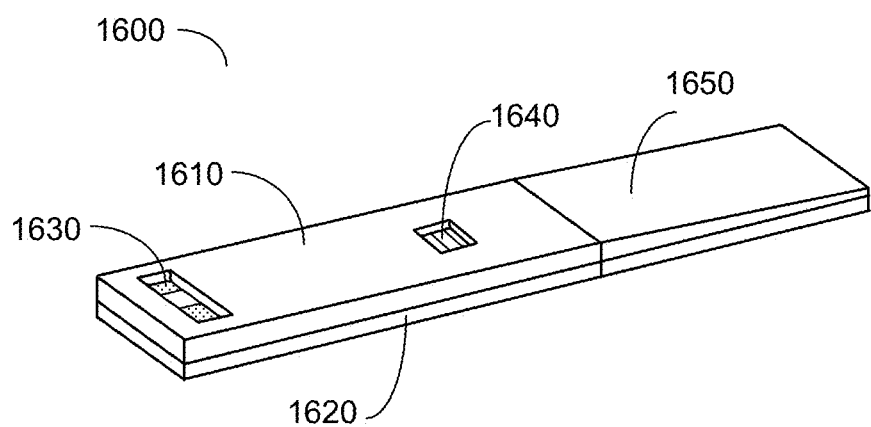
FIG. 16 is a schematic of a microfluidic microscopy device including a lateral flow assay.

FIGS. 14, 15, and 16 illustrate non-limiting embodiments of a microfluidic microscopy device including a lateral flow assay. FIG. 14 is a schematic of microfluidic microscopy device 1400. Device 1400 includes absorbent structure 1410, support structure 1420, lid structure 1430, and clamping structure 1440. Absorbent structure 1410 includes a first portion 1450 including at least one dry dye for a liquid and a second portion 1460 including a lateral flow assay. In this embodiment, a polar liquid is applied to the first end of device 1400 and allowed to migrate in parallel through first portion 1450 and second portion 1460. For example, one or more cells in a polar liquid, e.g., blood, may be stained with at least one dry dye for a liquid, e.g., acridine orange, while migrating through first portion 1450 and in parallel, one or more components in the polar liquid, e.g., an antigen, may be detected using the lateral flow assay in second portion 1460. FIG. 15 is a schematic of another embodiment of a microfluidic microscopy device. Device 1500 including absorbent structure 1510, support structure 1520, lid structure 1530, and clamping structure 1540. Absorbent structure 1510 further includes first portion 1550 including at least one dry dye for a liquid and second portion 1560 including a lateral flow assay. Second portion 1560 including a lateral flow assay further includes test line 1570 and control line 1580. For example, a positive result can be indicated by appearance or change in appearance of the test line and the control line in response to interaction of an antigen in the polar liquid with an antibody portion of the lateral flow assay. FIG. 16 is a schematic of another embodiment of a microfluidic microscopy device. Device 1600 includes a lid structure 1610 and a support structure 1620 enclosing an absorbent structure including a first portion with at least one dry dye for a liquid and a second portion with a lateral flow assay. Lid structure 1610 includes an opening defining a sample reservoir 1630. Lid structure 1610 further includes an opening defining results window 1640 where results of a lateral flow assay may be read, e.g., a test line and a control line. Device 1600 further includes tapered internal chamber 1650 formed from lid structure 1610 and support structure 1620 and including at least one optically transparent portion suitable for microscopy.

FIG. 17 illustrates aspects of a method for preparing a liquid sample with a microfluidic microscopy device. The method includes in block 1700, receiving a liquid sample at a first end of a microfluidic microscopy device, the microfluidic microscopy device including an absorbent structure with a first end and a second end, the absorbent structure including an interior hydrophilic region with at least one dry dye for a liquid; a support structure positioned adjacent to a first surface of the absorbent structure, the support structure including a second end region positioned adjacent to the second end of the absorbent structure; a lid structure positioned adjacent to a second surface of the absorbent structure, the second end of the lid structure projecting beyond the second end of the absorbent structure, the second end of the lid structure including a second end region positioned adjacent to the second end of the absorbent structure and overlapping with the second end region of the support structure; and a clamping structure positioned to maintain a relative position of the support structure and the lid structure to form a tapered internal chamber adjacent to the second end of the absorbent structure, the tapered internal chamber including an internal surface of the second end region of the support structure facing an internal surface of the second end region of the lid structure, the tapered internal chamber including an outflow region; in block 1710, migrating the liquid sample from the first end of the absorbent structure to the second end of the absorbent structure through the interior hydrophilic region and the least one dry dye for a liquid; in block 1720, dissolving the at least one dry dye for a liquid in the liquid sample while migrating the liquid sample through the interior hydrophilic region; in block 1730, migrating the liquid sample with the dissolved at least one dry dye for a liquid from the second end of the absorbent structure into a tapered internal chamber; and in block 1740, filling the tapered internal chamber with the liquid sample with the dissolved at least one dry dye for a liquid while pushing air out of the tapered internal chamber through the outflow region.

In an aspect, receiving the liquid sample at the first end of the microfluidic microscopy device includes receiving the liquid sample at the first end of the absorbent structure. In an aspect, the method includes receiving a liquid sample that is a polar liquid. In an aspect, the method includes receiving the liquid sample as one or more drops applied directly to the first end of the absorbent structure. For example, the liquid sample can be received as one or more drops of liquid, e.g., a blood sample, applied directly to the first end of the absorbent structure using a syringe needle, a pipette, or capillary pipette. In an aspect, receiving the liquid sample at the first end of the absorbent structure may require adding a drop of liquid sample, waiting for the drop to migrate into the absorbent structure before adding subsequent drops.

In an aspect, receiving the liquid sample at the first end of the microfluidic microscopy device includes receiving the liquid sample from a sample reservoir positioned at the first end of the microfluidic microscopy device, the sample reservoir in fluid communication with the first end of the absorbent structure. For example, receiving the liquid sample can include adding one or more drops of liquid sample, e.g., blood, to a sample reservoir adjacent to and in fluid communication with the first end of the absorbent structure. In an aspect, the method includes drawing the liquid sample from the sample reservoir into the first end of the absorbent material by capillary action.

In an aspect, the method includes receiving a blood sample at the first end of the microfluidic microscopy device. In an aspect, the method includes receiving the blood sample directly from a finger stick. For example, the liquid sample can be received at the first end of the absorbent structure by touching the first end of the absorbent structure with a bleeding portion of a finger pricked with a lancet. For example, the method can include receiving a blood sample from a drop of blood from a blood draw of an individual. In an aspect, the method includes receiving other examples of body fluids at the first end of the microfluidic microscopy device. Non-limiting examples of body fluids include amniotic fluid, bile, cerebrospinal fluid, peritoneal fluid, pleural fluid, saliva, seminal fluid, synovial fluid, tears, sweat, vaginal secretion, or urine.

In an aspect, the method includes receiving a blood or body fluid sample that is infected with a pathogen. In an aspect, the pathogen includes a parasite, e.g., a form of *Plasmodium*. For example, the method includes receiving a blood sample from an individual in a geographical region, e.g., Central Africa, where malaria is endemic. For example, the method includes receiving a blood sample from an individual suspected of being infected with the malaria-causing parasite *Plasmodium falciparum* and using the microfluidic microscopy device to stain the cells associated with the received blood sample. The method may further include providing and using an optical detector, e.g., a microscope, to qualify and/or quantify potentially infected cells in the tapered internal chamber of the device.

In an aspect, the method includes receiving a blood or body fluid sample that includes other pathogens including, but not limited to, bacteria, e.g., *Escherichia coli, Streptococcus* or *Staphylococcus*, or viruses, e.g., human immunodeficiency virus (HIV), hepatitis B, or hepatitis C. In an aspect, the method includes receiving a blood or body fluid sample that includes other cell types associated with pathology, e.g., metastatic tumor cells.

In an aspect, the method includes migrating the liquid sample from the first end of the absorbent structure to the second end of the absorbent structure at a fixed flow rate.

In an aspect, the method includes migrating the liquid sample from the first end of the absorbent structure to the second end of the absorbent structure at a variable flow rate. In an aspect, the method includes migrating the liquid sample at a variable flow rate dictated by one or more properties of the absorbent structure. In an aspect, the method includes migrating the liquid sample at a variable flow rate dictated by a shape of the absorbent structure. For example, the flow rate through the absorbent structure may be modulated by the presence of bottlenecks cut into the absorbent structure to alter the flow path. In an aspect, the method includes migrating the liquid sample at a variable rate dictated by one or more hydrophobic regions incorporated into the absorbent structure. For example, the flow rate through the absorbent structure may be modulated by the presence of channels or bottlenecks formed by one or more hydrophobic regions incorporated into the absorbent structure.

In an aspect, the method further includes staining one or more cellular components of the liquid sample with the at least one dry dye for a liquid while migrating the liquid sample from the first end of the absorbent structure through the interior hydrophilic region to the second end of the absorbent structure. In an aspect, the method includes staining one or more cellular components in a blood sample, e.g., red blood cells, white blood cells, and/or platelets. In an aspect, the method includes staining other components of a body fluid, non-limiting examples of which include bacteria, viruses, or metastatic tumor cells.

In an aspect, the staining intensity of the cellular components of the liquid sample is dependent upon the residence time of the liquid sample in the absorbent structure, e.g., the amount of time that the liquid sample is exposed to the at least one dry dye for a liquid. In an aspect, the staining intensity of the cellular components of the liquid sample is dependent on the concentration and ease of rehydration of the at least one dry dye for a liquid in the absorbent structure. For example, the higher the concentration of dry dye present in the absorbent structure or the more readily the dry dye is rehydrated in the migrating liquid sample, the higher the concentration of solubilized dye available for staining the cellular components of the liquid sample. In an aspect, the staining intensity of the cellular components of the liquid sample is dependent upon a balance between a filling rate, e.g., the rate of flow through the absorbent structure and filling of the tapered internal chamber, and a concentration of the at least one dry dye for a liquid.

In an aspect, the method further includes migrating the liquid sample from a first region of the absorbent structure including at least one first dry dye for a liquid to a second region of the absorbent structure including at least one second dry dye for a liquid. For example, the method can include migrating the liquid sample through a first region of the absorbent structure that includes a first dye, e.g., eosin, followed by migrating the liquid sample through a second region of the absorbent structure that includes a second dye, e.g., hematoxylin. Non-limiting examples of absorbent structures including two or more regions with two or more dry dyes for a liquid for use in differential staining of the cellular components of a liquid sample have been described above herein and in FIGS. 3A-3J.

In an aspect, the method further includes removing at least a portion of the dissolved at least one dry dye for a liquid by migrating the liquid sample through a portion of the absorbent structure devoid of the at least one dry dye for a liquid. For example, a portion of the absorbent structure can be used to remove that portion of the dissolved dry dye for a liquid that has not been incorporated into one or more cells in the liquid sample. In an aspect, removing at least a portion of the dissolved at least one dry dye for a liquid in the absorbent structure reduces the background color or fluorescence measured with an optical detector in the tapered internal chamber. For example, the method can include migrating the liquid sample through a first region of the absorbent structure including a fluorescing dye, e.g., acridine orange, to a second region of the absorbent structure lacking a dry dye to remove excess acridine orange prior to migrating the liquid sample into the tapered internal chamber for optical detection.

In an aspect, the method includes migrating the liquid sample through a first region of the absorbent structure including at least one first dry dye for a liquid to a second region of the absorbent structure lacking a dry dye to a third region of the absorbent structure including at least one second dry dye for a liquid to a fourth region of the absorbent structure lacking a dry dye and into the tapered internal chamber. For example, the method can include migrating the liquid sample through a first region of the absorbent structure including a nuclear stain, e.g., methylene blue and/or Azure B, to differentially stain nuclei of one or more cells in the liquid sample, to a second region lacking a dry dye to remove excess nuclear stain, to a third region of the absorbent structure including a cytoplasmic stain, e.g., eosin Y, to differentially stain the cytoplasm of one or more cells in the liquid sample, to a fourth region lacking a dry dye to remove excess cytoplasmic stain, and into the tapered internal chamber for optical detection.

The method includes migrating the liquid sample with the dissolved at least one dry dye for a liquid from the second end of the absorbent structure into the tapered internal chamber. In an aspect, the method includes migrating the liquid sample with the dissolved at least one dry dye for a liquid from the second end of the absorbent structure into the tapered internal chamber from a single point. For example, the method can include using an absorbent structure that includes a shape at the second end that creates a single emergent flow point for flow of liquid from the absorbent structure and into the tapered internal chamber.

In an aspect, the method includes migrating the liquid sample with the dissolved at least one dry dye for a liquid from the second end of the absorbent structure into the tapered internal chamber from two or more points. For example, the method can include using an absorbent structure that includes a shape at the second end of the absorbent structure that creates two or more emergent flow points for flow of liquid from the absorbent structure into the tapered internal chamber. Non-limiting examples of absorbent structures with linear and non-linear edges have been described above herein and in FIGS. 4A-4D. In an aspect, the method includes modulating the rate of flow from the second end of the absorbent structure and into the tapered internal chamber by altering the number of emergent flow points.

The method includes pushing the air out of the tapered internal chamber through an outflow region as the tapered internal chamber is filling with liquid. In an aspect, the method includes pushing the air out of the tapered internal chamber through a hydrophobic region at the outer edges of the tapered internal chamber. For example, air trapped in the tapered internal chamber during filling with the liquid sample can be pushed out through a silane-based hydrophobic region at the outer edges of an otherwise unsealed tapered internal chamber. For example, the hydrophobic region at the outer edges of the tapered internal chamber can act as a barrier to flow of the liquid sample while allowing air to vent out of the tapered internal chamber.

In an aspect, the method includes pushing the air out of the tapered internal chamber through a hydrophobic region patterned on at least one of the internal surface of the second end region of the support structure or the internal surface of the second end region of the lid structure. For example, the method can include pushing the air out of the tapered internal chamber through a hydrophobic region positioned at one or more unsealed edges of the tapered internal chamber. For example, the method can include pushing the air out of the tapered internal chamber along one or more hydrophobic regions patterned perpendicular to the liquid flow and spreading out toward the side edges of the tapered internal chamber. For example, the method can include pushing the air out of the tapered internal chamber along hydrophobic regions patterned parallel to the liquid flow and spreading out towards the end edge of the tapered internal chamber. Non-limiting examples of patterned hydrophobic regions have been described above herein and in FIGS. 10A-10C.

In an aspect, the method includes pushing air out of the tapered internal chamber back through an interior hydrophobic region incorporated into the absorbent structure. For example, the method can include pushing air out of the tapered internal chamber using an interior hydrophobic region such as illustrated in FIG. 11A and is described in more detail in Example 2.

FIG. 18 illustrates aspects of a method for analyzing a liquid sample in a tapered internal chamber. The method includes providing an optical detector in block 1800; and in block 1810, using the optical detector to measure an optical property of a liquid sample in a tapered internal chamber of a microfluidic microscopy device, the microfluidic microscopy device including an absorbent structure with a first end and a second end, the absorbent structure including an interior hydrophilic region with at least one dry dye for a liquid, the absorbent structure configured to convey the liquid sample from the first end of the absorbent structure through the interior hydrophilic region and the at least one dry dye for a liquid to the second end of the absorbent structure; a support structure positioned adjacent to a first surface of the absorbent structure, the support structure including a first end and a second end, the second end of the support structure including a second end region positioned adjacent to the second end of the absorbent structure; a lid structure positioned adjacent to a second surface of the absorbent structure, the lid structure including a first end and a second end, the second end of the lid structure projecting beyond the second end of the absorbent structure, the second end of the lid structure including a second end region positioned adjacent to the second end of the absorbent structure and overlapping with the second end region of the support structure; a clamping structure positioned to maintain a relative position of the support structure and the lid structure to form the tapered internal chamber, the tapered internal chamber including an internal surface of the second end region of the support structure facing an internal surface of the second end region of the lid structure, the tapered internal chamber including an outflow region.

In an aspect, the method includes providing a microscope as an optical detector. In an aspect, the method includes providing a laboratory light microscope. Non-limiting examples of microscopy techniques for use with a light microscope include bright field microscopy, dark field microscopy, phase contrast microscopy, and fluorescence microscopy. In an aspect, the microfluidic microscopy device is sized to fit on a microscope specimen stage, as described above herein. In an aspect, the microscope can include a field-portable, lensfree microscope. See, e.g., Isikman et al. (2011) "Field-portable lensfree tomographic microscope" *Lab Chip* 11:2222-2230; and Bishara et al. (2011) "Handheld, lensless microscope identifies malaria parasites" *SPIE Newsroom* DOI:10.1117/2.1201107.003812, which are incorporated herein by reference. In an aspect, the microscope is part of a smart phone. See, e.g., Wei et al. (2013) "Fluorescent imaging of single nanoparticles and viruses on a smart phone" *ACS Nano* DOI: 10.1021/nn4037706, which is incorporated herein by reference.

In an aspect, the method includes providing a spectrophotometer as an optical detector. For example, a spectrophotometer can be added to a microscope to enable spectroscopy measurements (308 PV Microscope Spectrophotometer, CRAIC Technologies, San Dimas, Calif.). In an aspect, the method includes providing a spectrofluorometer. For example, a spectrofluorometer can be used to measure and record fluorescence spectra emitted from a fluorescent dye or dyes associated with the liquid sample in the tapered internal chamber. In an aspect, the spectrophotometer is connected to a computing device and part of an automated detection system.

In an aspect, the method includes using the optical detector to measure a fluorescence intensity of the liquid sample in the tapered internal chamber. In an aspect, the method includes using the optical detector to measure a fluorescence intensity of a liquid sample that includes a polar liquid. In an aspect, the method includes using the optical detector to measure a fluorescence intensity of one or more components of a body fluid. For example, the method can include using the optical detector to measure a fluorescence intensity of a liquid sample, e.g., a blood sample, stained with a fluorescing dye, e.g., acridine orange, while migrating through the absorbent structure. In an aspect, the optical detector includes a light source, e.g., a lamp, a laser, or light emitting diode with or without excitation filters to excite a fluorophore associated with a fluorescing dye at an appropriate wavelength. For example, the optical detector can include a xenon arc lamp or mercury-vapor lamp and excitation filters. For example, the optical detector can include a light emitting diode light source emitting at a specific wavelength, e.g., 520 nm, for use with fluorescing dyes that are excited at or around 520 nm. Non-limiting examples of fluorescing dyes have been described above herein. In an aspect, the method includes using the optical detector to measure a fluorescence intensity of at least one fluorescing dye that is evenly dispersed in the liquid sample. In an aspect, the method includes using the optical detector to measure a fluorescence intensity of at least one fluorescing dye concentrated in a cellular component of the liquid sample, e.g., concentrated in DNA or RNA of the cellular component.

In an aspect, the method includes using the optical detector to measure a color intensity of the liquid sample in the tapered internal chamber. In an aspect, the method includes using the optical detector to measure a color intensity of a liquid sample that includes a polar liquid. In an aspect, the method includes using the optical detector to measure a color intensity of one or more components of a body fluid. For example, the method can include using the optical detector to detect colorimetric staining of one or more cellular components in the liquid sample in the tapered internal chamber. For example, the method can include using an optical light microscope to assess the presence of cells in the tapered internal chamber that are differentially stained with the at least one dry dye for a liquid, e.g., a Giemsa stain.

In an aspect, the method includes using the optical detector to measure an optical property associated with one or more cellular components in the liquid sample in the tapered internal chamber. In an aspect, the optical property is a fluorescence intensity or a color intensity associated with the one or more cellular components in the liquid sample. For example, the method can include using the optical detector, e.g., a fluorescence microscope, to measure a fluorescence property, e.g., a green fluorescence property, associated with one or more cellular components in the liquid sample stained with a fluorescing dye, e.g., acridine orange. For example, the method can include using the optical detector, e.g., a brightfield microscope, to measure a color intensity, e.g., purple and pink, associated with one or more cellular components in the liquid sample stained with a color stain, e.g., the components of a Giemsa stain. In an aspect, the method includes differentiating types of cells in the liquid sample based on the optical properties of the liquid sample in the tapered internal chamber. For example, the method includes using the optical properties of the cellular components of the liquid sample in the tapered internal chamber to differentiate white blood cells from red blood cells. For example, the method includes using the optical properties of the cellular components of the liquid sample in the tapered internal chamber to differentiate *Plasmodium*-infected and -uninfected red blood cells. For example, the method includes using the optical properties of the cellular components of the liquid sample in the tapered internal chamber to determine a life-cycle stage of a parasite. For example, the method includes using the optical properties of the cellular components of the liquid sample in the tapered internal chamber to differentiate between different types of parasites, e.g., *Plasmodium falciparum* versus *Plasmodium vivax*. For example, *P. falciparum* infected blood samples are characterized by the presence of young trophozoites (i.e., rings) in the red blood cells while *P. vivax* infected blood samples have enlarged red blood cells and the appearance of granules (i.e., Schuffner's dots) in the red blood cell cytoplasm. In the case of parasite infection, identification of the parasite type present in a blood sample can be used to inform treatment options, e.g., artemisinin versus chloroquine.

In an aspect, the method includes using the optical detector to measure the optical property of the liquid sample at two or more points along a microscopy viewing region of decreasing depth of the tapered internal chamber. For example, the microscopy viewing region at that portion of the tapered internal chamber nearest the second end of the absorbent structure will have greater field of depth than the microscopy viewing region at that portion of the tapered internal chamber where the internal surfaces of the second end regions of the support structure and the lid structure come together. For example, the microscopy viewing region of decreasing depth can be used to simulate a thick smear, e.g., with multiple layers of cells, and a thin smear, e.g., with a monolayer of cells.

In an aspect, the method includes using the optical detector to count one or more cell types in the liquid sample in the tapered internal chamber. In an aspect, the method includes manually counting the one or more cell types in the liquid sample in the tapered internal chamber. For example, a technician may use a microscope to count one or more cell types, e.g., one or more blood cells in a blood sample, in the tapered internal chamber. In an aspect, the method includes automatically counting one or more cell types, e.g., one or more fluorescently labeled cells in a blood sample, in the tapered internal chamber. For example, an optical detector, e.g., a microscope with fluorescence capability and an image capture device connected to a computer, can be used to automatically recognize and count one or more fluorescently labeled cells in the liquid sample. See, e.g., Kachouie et al. (2009) "Arraycount, an algorithm for automatic cell counting in microwell arrays" *Biotechniques* 47:x-xvi; and Vink et al. (2013) "An automatic vision-based malaria diagnosis system" *J. Microscopy* 250:166-178, which are incorporated herein by reference.

In an aspect, the method includes using the optical detector to count one or more cell types in the liquid sample in the tapered internal chamber to determine a medical diagnosis. In an aspect, the method includes using the optical detector to count *Plasmodium*-infected red blood cells in a blood sample in the tapered internal chamber of the microfluidic microscopy device. For example, the method can include counting *Plasmodium*-infected red blood cells relative to other components of the liquid sample in the tapered internal chamber to determine the degree of parasitemia. For example, parasitemia associated with malaria can be reported as the number of parasites per microliter of blood (parasites/ul) from a thick blood smear, wherein the microliters of blood are estimated by counting the number of white blood cells in a blood sample (approximately 8000 white blood cells per microliter). In some embodiments, the number of parasites per 200 white blood cells can be used to estimate the number of parasites per microliter. For example, the number of asexual parasites and white blood cells can be counted in each microscopic field, e.g., 25 microscopic fields, until the overall white blood cell count reaches 200. The number of parasites per 200 white blood cells can be counted and multiplied by 40 to give an estimate of the number of parasites per 8000 white blood cells and therefore the number of parasites per microliter. Alternatively, an estimate of the number of parasites per red blood cells can be used.

In an aspect, the method further includes calculating a volume calibration by using the optical detector to measure the optical property of the liquid sample in the tapered internal chamber. In an aspect, volume calibration is based on the intensity of a background fluorescence at various points in the tapered internal chamber. In an aspect, the background intensity measured using the optical detector scales linearly with the thickness of the tapered internal chamber area. It is anticipated that the highest level of background fluorescence will be measured at the largest depth of the tapered internal chamber, e.g., adjacent to the second edge of the absorbent structure. It is anticipated that the lowest level of background fluorescence will be measured at the smallest depth of the tapered internal chamber, e.g., where the lid structure and the support structure meet at their respective second ends. In an aspect, a calibration curve can be generated using the fluorescence intensity in combination with known depths at various points in the tapered internal chamber. In an aspect, the volume calibration for a given microscopic field can be combined with a number of positively stained cells in the microscopic field to generate a calculated number of positively stained cells per volume, e.g., cells/microliter.

In an aspect, the method further includes generating a diagnosis regarding a medical condition by using the optical detector to measure the optical property of the liquid sample in the tapered internal chamber. In an aspect, the method includes generating a diagnosis of parasitemia, e.g., malaria, by using the optical detector to measure an optical property of the liquid sample, e.g., a blood sample, in the tapered internal chamber. For example, the method includes generating a diagnosis of malaria by using an optical detector, e.g., a fluorescence microscope, to measure the optical properties, e.g., fluorescence properties, of one or more cellular components of a blood sample in the tapered internal chamber of a microfluidic device, the blood sample stained with acridine orange. The method can include generating a diagnosis regarding other medical conditions, non-limiting examples of which include a bacterial infection, a viral infection, cancer, and/or metastasis based on the type and number of cellular components detected with the optical detector in a liquid sample in the tapered internal chamber. For example, the presence of white and/or red blood cells in urine may indicate a urinary tract or kidney infection. For example, the presence of red blood cells and/or bacteria in pleural fluid may indicate a pulmonary infection or other pulmonary pathology, e.g., malignancy or infarction.

Non-limiting embodiments of the devices and methods described herein are presented in the following examples.

Example 1

Microscopic View of Cells within a Tapered Internal Chamber of a Microfluidic Microscopy Device In this example, a polar liquid, i.e., a *Plasmodium*-infected blood sample, was examined in a tapered internal chamber of a microfluidic microscopy device using brightfield and fluorescence microscopy.

Figure 19A:
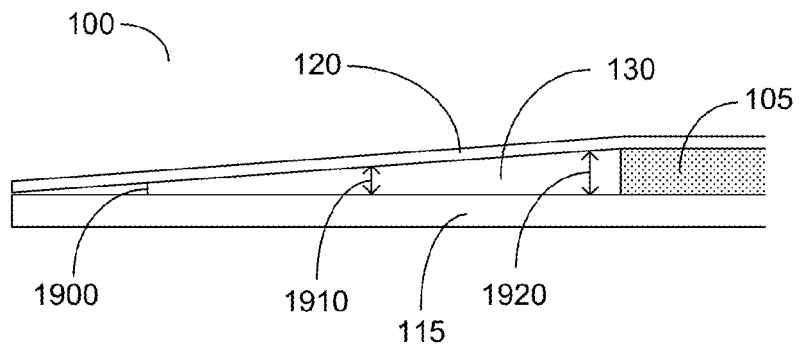
FIG. 19A is a schematic of a side view of a cross-section through the tapered internal chamber of a microfluidic microscopy device.

FIG. 19A shows a schematic of a side view cross-section through the tapered internal chamber of a microfluidic microscopy device 100. Tapered internal chamber 130 of device 100 is formed from a second end region of support structure 115 and a second end region of lid structure 120. The distance between an internal surface of the second end region of support structure 115 and an internal surface of the second end region of lid structure 120 varies along the length of tapered internal chamber 130, shown in the schematic diagram as thin depth 1900 representative of a "thin smear"; medium depth 1910 representative of a "medium smear"; and thick depth 1920 representative of a "thick smear" proximal to the second end absorbent structure 105.

Figure 19B:
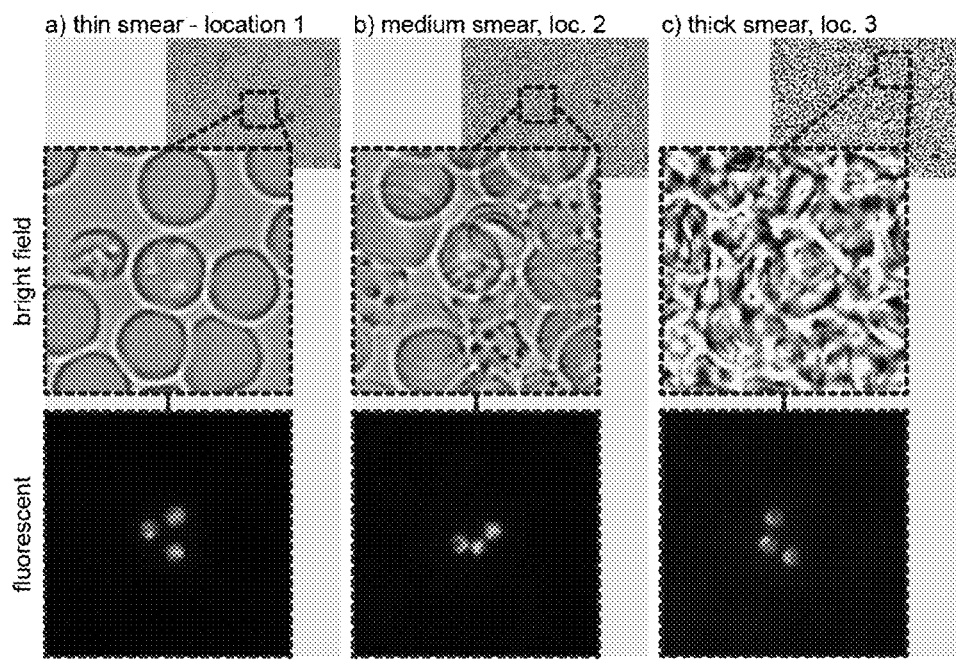
FIG. 19B shows micrographs taken at various depths along a tapered internal chamber.

FIG. 19B shows micrographs of the *Plasmodium*-infected blood sample taken at various depths along the tapered internal chamber. In this example, the *Plasmodium*-infected blood sample was applied to the first end of the microfluidic microscopy device and migrated through an absorbent structure, e.g., a piece of filter paper, which included dried acridine orange. DNA and RNA associated with cellular components of the *Plasmodium*-infected blood sample were stained with the acridine orange while migrating through the absorbent structure and into the tapered internal chamber of the microfluidic microscopy device. DNA staining with acridine orange is detected with excitation wavelength of 500 nm and an emission wavelength of 526 nm. RNA staining with acridine orange is detected with excitation wavelength of 460 and emission wavelength of 650. Three regions of the tapered internal chamber, e.g., at thin depth 1900, medium depth 1910, and thick depth 1920, were examined by both bright field and fluorescence microscopy using a 60× objective without oil immersion. For each panel, brightfield and fluorescence images were captured without moving the microscope stage. Panel a) shows brightfield and fluorescent micrographs of a "thin smear" taken at a thin depth, e.g., thin depth 1900, along the length of the tapered internal chamber. The cells shown in the brightfield micrograph form a monolayer at this depth. The fluorescent micrograph shows fluorescent staining associated with DNA/RNA of *Plasmodium* in infected red blood cells. Panel b) shows brightfield and fluorescent micrographs of a "medium smear" taken at a medium depth, e.g., medium depth 1910, along the length of the tapered internal chamber. The cells in the brightfield micrograph form several layers of cells. The fluorescent micrograph shows fluorescent staining associated with DNA/RNA of *Plasmodium* in an infected red blood cell. Panel c) shows brightfield and fluorescent micrographs of a "thick smear" taken at a thick depth, e.g., thick depth 1920, along the length of the tapered internal chamber. The cells in the brightfield micrograph form multiple layers of cells. The fluorescent micrograph shows fluorescent staining associated with DNA/RNA of *Plasmodium* in an infected red blood cell.

Example 2

Filling the Tapered Internal Chamber of a Microfluidic Microscopy Device from the Absorbent Structure and Removing Air In this example, an interior hydrophobic region was incorporated into the absorbent structure of a microfluidic microscopy device to facilitate removal of air from the tapered internal chamber during filling with a polar liquid.

Figure 20A:
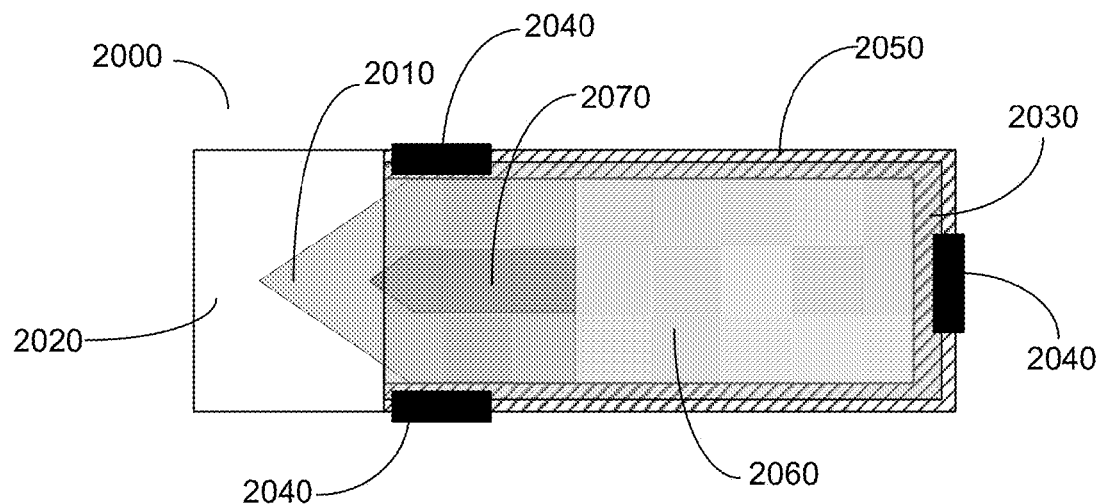
FIG. 20A is a schematic of a top view of a microfluidic microscopy device.

FIG. 20A shows a top view schematic of the device used in the example. Device 2000 includes absorbent structure 2010, support structure 2020, and lid structure 2030 positioned together with clamping structure 2040 to form a tapered internal chamber. Absorbent structure 2010 includes at least one dry dye for a liquid. Support structure 2020 and lid structure 2030 are positioned adjacent of opposite surfaces of absorbent structure 2010. Device 2000 further includes hydrophobic region 1150 patterned on the surface of support structure 2020. Hydrophobic region 2050 forms a barrier preventing the leakage of a polar liquid from device 2020. Clamping structure 2040 is positioned to maintain a relative position of support structure 2020 and lid structure 2030 to form tapered internal chamber 2060 adjacent to the second end of absorbent structure 2010. Device 2000 further includes interior hydrophobic region 2070 positioned adjacent to an interior hydrophilic region of absorbent structure 2010. Interior hydrophobic region 2070 is configured to vent air from tapered internal chamber 2060 during filling with a polar liquid.

In this example, a piece of paper towel was cut into the 5-sided shape shown in FIG. 20A for use as absorbent structure 2010. A small piece was further cut from the 5-sided shape piece of paper towel and treated with perfluorodecyltrichlorosilane using vapor phase deposition to generate interior hydrophobic region 2070. The small piece of treated paper towel was reinserted into the larger untreated piece of paper towel and positioned between a support structure 2020, e.g., a standard 75×25 mm microscope slide and a lid structure 2030, e.g., a glass coverslip, and clamped together with a clamping structure 2040, e.g., small binder clips. One of the flat surfaces of the microscope slide was coated on the edges with perfluorodecyltrichlorosilane using vapor phase deposition with a mask to generate a hydrophobic barrier to prevent the polar liquid from spilling out the sides of the device.

Figure 20B:
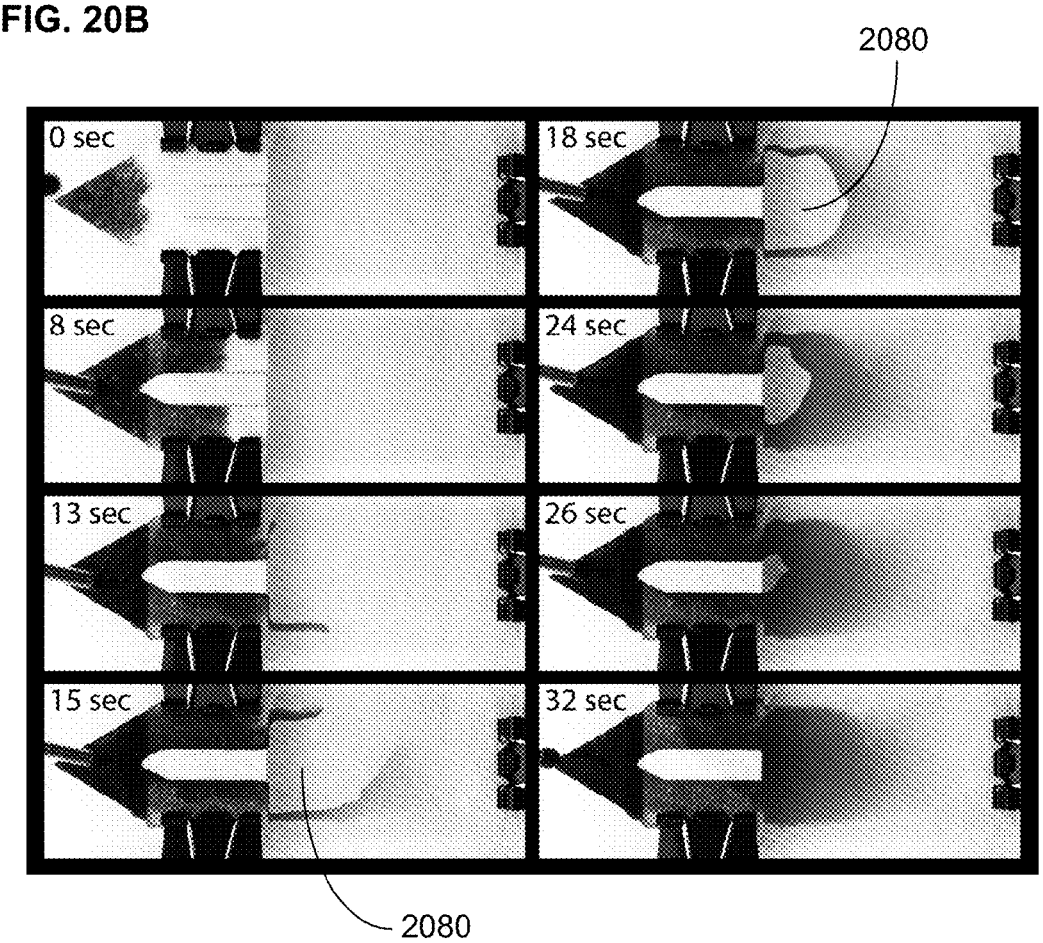
FIG. 20B shows photographs depicting flow of a polar liquid through a microfluidic microscopy device over time.

FIG. 20B shows a series of photographs taken over time depicting migration of a polar fluid, e.g., blood, through the paper towel absorbent structure and into the tapered internal chamber with concomitant removal of trapped air from the tapered internal chamber. A sample of blood was added at time 0 to the first end of the 5-sided piece of paper towel and allowed to migrate by capillary action. At 8 seconds, the blood had migrated through most of the 5-sided piece of paper towel, avoiding the perfluorodecyltrichlorosilane treated, i.e., interior hydrophobic region, of the paper towel. At 13 seconds, the blood was observed migrating from the paper towel and into the tapered internal chamber formed from the space generated by clamping the microscope slide and the coverslip on either side of the 5-sided piece of paper towel. At 15 seconds, the blood was observed filling the side walls of the device and an air bubble 2080 began to be apparent. At 18, 24, and 26 seconds, air bubble 2080 was progressively decreased in size as it was vented back through the interior hydrophobic region of the paper towel. By 32 seconds, the tapered internal chamber was completely filled with the blood sample, with no remaining observable air bubbles.

Aspects of the subject matter described herein are set out in the following numbered paragraphs:

1. In some embodiments, a microfluidic microscopy device includes: an absorbent structure with a first end and a second end, the absorbent structure including an interior hydrophilic region, the absorbent structure configured to convey a polar liquid from the first end of the absorbent structure through the interior hydrophilic region to the second end of the absorbent structure; a support structure positioned adjacent to a first surface of the absorbent structure, the support structure including a first end and a second end, the second end of the support structure including a second end region positioned adjacent to the second end of the absorbent structure; a lid structure positioned adjacent to a second surface of the absorbent structure, the lid structure including a first end and a second end, the second end of the lid structure projecting beyond the second end of the absorbent structure, the second end of the lid structure including a second end region positioned adjacent to the second end of the absorbent structure and overlapping with the second end region of the support structure; and a clamping structure positioned to maintain a relative position of the support structure and the lid structure to form a tapered internal chamber adjacent to the second end of the absorbent structure, the tapered internal chamber including an internal surface of the second end region of the support structure facing an internal surface of the second end region of the lid structure, the tapered internal chamber including an outflow region.
2. The device of paragraph 1, wherein the absorbent structure includes an absorbent paper structure.
3. The device of paragraph 1, wherein the absorbent structure includes at least one of glass fiber, silica fiber, nitrocellulose, cellulose ester, polyether sulfone, polysulfone, polyethylene, tetrafluoride, polyvinylidene fluoride, polycarbonate, polypropylene, polyamide, nylon, polyester, cotton, or stainless steel fiber.
4. The device of paragraph 1, wherein the first end of the absorbent structure includes a first end region open to a position adjacent to the device and configured to receive the polar liquid.
5. The device of paragraph 1, wherein the absorbent structure is configured to convey the polar liquid from the first end of the absorbent structure through the interior hydrophilic region to the second end of the absorbent structure and into the tapered internal chamber.
6. The device of paragraph 1, wherein the second end of the absorbent structure includes a linear edge.
7. The device of paragraph 1, wherein the second end of the absorbent structure includes a non-linear edge.
8. The device of paragraph 1, wherein the second end of the absorbent structure includes one emergent flow point.
9. The device of paragraph 1, wherein the second end of the absorbent structure includes two or more emergent flow points.
10. The device of paragraph 1, wherein the absorbent structure is fabricated from a hydrophilic material.
11. The device of paragraph 1, wherein the interior hydrophilic region is integral to the absorbent structure.
12. The device of paragraph 1, wherein the interior hydrophilic region is printed onto the absorbent structure.
13. The device of paragraph 1, wherein the polar liquid includes a body fluid.
14. The device of paragraph 13, wherein the body fluid includes blood.
15. The device of paragraph 13, wherein the body fluid includes at least one of amniotic fluid, bile, cerebrospinal fluid, peritoneal fluid, pleural fluid, saliva, seminal fluid, synovial fluid, sweat, tears, vaginal secretion, or urine.
16. The device of paragraph 1, wherein the absorbent structure further includes at least one dry dye for a liquid, the absorbent structure configured to convey the polar liquid from the first end of the absorbent structure through the hydrophilic region and the at least one dry dye for a liquid to the second end of the absorbent structure.
17. The device of paragraph 16, wherein the at least one dry dye for a liquid is of a chemical structure to stain one or more components in the polar liquid upon contact with the polar liquid.
18. The device of paragraph 17, wherein the one or more components in the polar liquid include one or more cells.
19. The device of paragraph 16, wherein the at least one dry dye for a liquid is of a type to stain *Plasmodium*-infected cells.
20. The device of paragraph 16, wherein a portion of the absorbent structure includes the at least one dry dye for a liquid.
21. The device of paragraph 16, where at least one first portion of the absorbent structure includes at least one dry dye of a first type for a liquid and at least one second portion of the absorbent structure includes at least one dry dye of a second type for a liquid.
22. The device of paragraph 21, wherein the at least one first portion of the absorbent structure including the at least one dry dye of the first type for a liquid is positioned in a region which is parallel to the at least one second portion of the absorbent structure including the at least one dry dye of the second type for a liquid and perpendicular to flow of the polar liquid from the first end of the absorbent structure to the second end of the absorbent structure.
23. The device of paragraph 16, wherein the at least one dry dye for a liquid includes at least one fluorescent dye.
24. The device of paragraph 16, wherein the at least one dry dye for a liquid comprises at least one of eosin, hematoxylin, methylene blue, Giemsa stain, or Wright stain.
25. The device of paragraph 1, wherein the absorbent structure further includes at least one anti-coagulant.
26. The device of paragraph 1, wherein the absorbent structure further includes at least one of an acid, a base, or a buffer.
27. The device of paragraph 1, wherein the absorbent structure further includes at least one lateral flow assay.
28. The device of paragraph 27, wherein the at least one lateral flow assay includes at least one of an immunological assay, enzymatic assay, chemical assay, or DNA amplification.
29. The device of paragraph 27, wherein the at least one lateral flow assay includes a colorimetric readout, an electrochemical readout, a fluorescent readout, a chemiluminescent readout, or an electrochemiluminescent readout.
30. The device of paragraph 1, wherein the absorbent structure further includes an interior hydrophobic region.
31. The device of paragraph 30, wherein the interior hydrophobic region includes at least one of silane, polydimethylsiloxane, wax, polystyrene, or alkyl ketene dimer.
32. The device of paragraph 30, wherein the interior hydrophobic region is printed onto the absorbent structure.
33. The device of paragraph 30, wherein the interior hydrophobic region is part of an air outflow region.
34. The device of paragraph 30, wherein the interior hydrophobic region is positioned adjacent to and parallel with the interior hydrophilic region of the absorbent structure, a first end of the interior hydrophobic region extending beyond the first end of the lid structure and open to a position adjacent to the device and a second end of the interior hydrophobic region positioned adjacent to the tapered internal chamber.
35. The device of paragraph 30, wherein the interior hydrophobic region includes a separate structure positioned adjacent to at least a portion of the absorbent structure and in a flow path of the polar liquid.
36. The device of paragraph 1, further includes a second absorbent structure, the second absorbent structure including a first end and a second end, the first end of the second absorbent structure adjacent to the second end of the absorbent structure and configured to convey the polar liquid from the second end of the absorbent structure to the first end of the second absorbent structure and through to the second end of the second absorbent structure and into the tapered internal chamber.

37. The device of paragraph 36, wherein the second absorbent structure includes at least one dry dye for a liquid.
38. The device of paragraph 1, wherein the support structure is rigid.
39. The device of paragraph 1, wherein at least a portion of the support structure is optically transparent and suitable for microscopy.
40. The device of paragraph 1, wherein at least a portion of the second end region of the support structure is optically transparent and suitable for microscopy.
41. The device of paragraph 1, wherein the support structure is fabricated from glass.
42. The device of paragraph 41, wherein the glass includes borosilicate glass, fused silica glass, or synthetic quartz glass.
43. The device of paragraph 1, wherein the support structure is fabricated from plastic.
44. The device of paragraph 43, wherein the plastic includes vinyl, polyvinylchloride, polystyrene, or ultraviolet transmittable acrylic.
45. The device of paragraph 1, wherein the first end of the support structure includes a first end region positioned adjacent to the first end of the absorbent structure.
46. The device of paragraph 45, wherein the first end region of the support structure includes a sample reservoir.
47. The device of paragraph 46, wherein the sample reservoir is formed from one or more wall structures extending outward from a surface of the first end region of the support structure.
48. The device of paragraph 45, wherein the first end region of the support structure includes one or more capillary channels in fluid communication with the first end of the absorbent structure.
49. The device of paragraph 1, wherein the lid structure is semi-rigid.
50. The device of paragraph 1, wherein at least a portion of the lid structure is optically transparent and suitable for microscopy.
51. The device of paragraph 1, wherein at least a portion of the second end region of the lid structure is optically transparent and suitable for microscopy.
52. The device of paragraph 1, wherein the lid structure is fabricated from glass.
53. The device of paragraph 52, wherein the glass includes borosilicate glass, fused silica glass, or synthetic quartz glass.
54. The device of paragraph 1, wherein the lid structure is fabricated from plastic.
55. The device of paragraph 54, wherein the plastic includes vinyl, polyvinylchloride, polystyrene, or ultraviolet transmittable acrylic.
56. The device of paragraph 1, wherein the first end of the lid structure includes a first end region, the first end region positioned adjacent to the first end region of the absorbent structure.
57. The device of paragraph 56, wherein the first end region of the lid structure includes a sample access region.
58. The device of paragraph 57, wherein at least part of the sample access region includes the first end of the absorbent structure.
59. The device of paragraph 1, wherein the clamping structure includes one or more binding bars.
60. The device of paragraph 1, wherein the clamping structure includes a structure wrapping around three sides of the support structure and the lid structure and leaving the first end of the absorbent structure accessible.
61. The device of paragraph 1, wherein the clamping structure includes at least one of an adhesive, glue, or heat seal.
62. The device of paragraph 1, wherein the tapered internal chamber includes a decreasing distance between the internal surface of the second end region of the support structure and the internal surface of the second end region of the lid structure.
63. The device of paragraph 62, wherein a maximum distance between the internal surface of the second end region of the support structure and the internal surface of the second end region of the lid structure forming the tapered internal chamber is defined by a thickness of the second end of the absorbent structure positioned adjacent to the tapered internal chamber.
64. The device of paragraph 62, wherein a minimum distance between the internal surface of the second end region of the support structure and the internal surface of the lid structure forming the tapered internal chamber is defined by a distance between the internal surface of the second end region of the support structure and the internal surface of the second end region of the lid structure when the clamping structure is in position.
65. The device of paragraph 62, wherein the decreasing distance between the internal surface of the second end region of the support structure and the internal surface of the second end region of the lid structure defines a microscopy viewing region of decreasing depth.
66. The device of paragraph 1, wherein the outflow region of the tapered internal chamber includes an air outflow region.
67. The device of paragraph 1, wherein the outflow region of the tapered internal chamber includes a liquid outflow region.
68. The device of paragraph 1, wherein the outflow region of the tapered internal chamber includes a hydrophobic region.
69. The device of paragraph 1, wherein the outflow region is positioned at one or more outer edges of the tapered internal chamber.
70. The device of paragraph 1, wherein at least a portion of the internal surface of the second end region of the support structure or the internal surface of the second end region of the lid structure forming the tapered internal chamber includes a hydrophobic region.
71. The device of paragraph 70, wherein the hydrophobic region includes a phase guide to convey air out of the tapered internal chamber.
72. The device of paragraph 70, wherein the hydrophobic region includes a hydrophobic material.
73. The device of paragraph 72, wherein the hydrophobic material includes at least one of wax, silane, nylon, polyethylene, polypropylene, polystyrene, polydimethylsiloxane, polytetrafluoroethylene, polychlorotrifluoroethylene, poly t-butyl methacrylate, hexatriacontane, poly (hexafluoropropylene), or polyisobutylene.
74. The device of paragraph 70, wherein the hydrophobic region is positioned along at least one outer edge of the tapered internal chamber.
75. The device of paragraph 70, wherein the hydrophobic region forms a hydrophobic barrier positioned along at least one outer edge of the tapered internal chamber.
76. The device of paragraph 70, wherein the hydrophobic region defines a flow channel.
77. The device of paragraph 70, wherein the hydrophobic region includes a pattern of hydrophobic material.
78. The device of paragraph 77, wherein the pattern of hydrophobic material forms a flow channel.

79. The device of paragraph 77, wherein the pattern of hydrophobic material includes one or more line of hydrophobic material positioned parallel to flow of the polar liquid into the tapered internal chamber.
80. The device of paragraph 77, wherein the pattern of hydrophobic material includes one or more lines of hydrophobic material positioned perpendicular to flow of the polar liquid into the tapered internal chamber.
81. The device of paragraph 77, wherein the internal surface of the second end region of the support structure or the internal surface of the second end region of the lid structure includes two or more hydrophobic regions.
82. The device of paragraph 1, wherein the tapered internal chamber forms a decreasing gradient volume of the polar liquid.
83. The device of paragraph 1, wherein one or more outer edges of the tapered internal chamber away from the absorbent structure are at least partially unsealed.
84. The device of paragraph 1, wherein combination of the absorbent structure, the support structure, and the lid structure are sized for use with a microscope.
85. In some embodiments, a microfluidic microscopy device includes: an absorbent structure with a first end and a second end, the absorbent structure including an interior hydrophilic region with at least one dry dye for a liquid, the absorbent structure configured to convey a polar liquid from the first end of the absorbent structure through the interior hydrophilic region and the at least one dry dye for a liquid to the second end of the absorbent structure; a support structure positioned adjacent to a first surface of the absorbent structure, the support structure including a first end and a second end, the second end of the support structure including a second end region positioned adjacent to the second end of the absorbent structure; a lid structure positioned adjacent to a second surface of the absorbent structure, the lid structure including a first end and a second end, the second end of the lid structure projecting beyond the second end of the absorbent structure, the second end of the lid structure including a second end region positioned adjacent to the second end of the absorbent structure and overlapping with the second end region of the support structure; a clamping structure positioned to maintain a relative position of the support structure and the lid structure to form a tapered internal chamber adjacent to the second end of the absorbent structure, the tapered internal chamber including an internal surface of the second end region of the support structure facing an internal surface of the second end region of the lid structure; and an interior hydrophobic region positioned adjacent to the interior hydrophilic region of the absorbent structure, a first end of the interior hydrophobic region open to a position adjacent to the device and a second end of the interior hydrophobic region positioned adjacent to the tapered internal chamber.
86. The device of paragraph 85, wherein the absorbent structure includes an absorbent paper structure.
87. The device of paragraph 85, wherein the absorbent structure includes at least one of glass fiber, silica fiber, nitrocellulose, cellulose ester, polysulfone, polyether sulfone, polyethylene tetrafluoride, polyvinylidene fluoride, polycarbonate, polypropylene, polyamide, polyester, or cotton.
88. The device of paragraph 85, wherein the first end of the absorbent structure includes a first end region open to a position adjacent to the device and configured to receive the polar liquid.
89. The device of paragraph 85, wherein the absorbent structure is configured to convey the polar liquid from the first end of the absorbent structure through the interior hydrophilic region and the at least one dry dye for a liquid to the second end of the absorbent structure and into the tapered internal chamber.
90. The device of paragraph 85, wherein the second end of the absorbent structure includes a linear edge.
91. The device of paragraph 85, wherein the second end of the absorbent structure includes a non-linear edge.
92. The device of paragraph 85, wherein the second end of the absorbent structure includes one emergent flow point.
93. The device of paragraph 85, wherein the second end of the absorbent structure includes two or more emergent flow points.
94. The device of paragraph 85, wherein the absorbent structure is fabricated from a hydrophilic material.
95. The device of paragraph 85, wherein the interior hydrophilic region is printed onto the absorbent structure.
96. The device of paragraph 85, wherein the polar liquid includes a body fluid.
97. The device of paragraph 96, wherein the body fluid includes blood.
98. The device of paragraph 96, wherein the body fluid includes at least one of amniotic fluid, bile, cerebrospinal fluid, peritoneal fluid, pleural fluid, saliva, seminal fluid, synovial fluid, tears, sweat, vaginal secretion, or urine.
99. The device of paragraph 85, wherein the at least one dry dye for a liquid is of a chemical structure to stain one or more components in the polar liquid upon contact with the polar liquid.
100. The device of paragraph 99, wherein the one or more components of the polar liquid include one or more cells.
101. The device of paragraph 85, wherein the at least one dry dye for a liquid is of a type to stain *Plasmodium*-infected cells.
102. The device of paragraph 85, wherein at least one first portion of the absorbent structure includes at least one dry dye of a first type for a liquid and at least one second portion of the absorbent structure includes at least one dry dye of a second type for a liquid.
103. The device of paragraph 102, wherein the at least one first portion of the absorbent structure including the at least one dry dye of the first type for a liquid is positioned in a region which is parallel to the at least one second portion of the absorbent structure including the at least one dry dye of the second type for a liquid and perpendicular to flow of the polar liquid from the first end of the absorbent structure to the second end of the absorbent structure.
104. The device of paragraph 85, wherein the at least one dry dye for a liquid includes at least one fluorescent dye.
105. The device of paragraph 85, wherein the at least one dry dye for a liquid includes at least one of eosin, hematoxylin, azure, methylene blue, Giemsa stain, or Wright stain.
106. The device of paragraph 85, wherein the absorbent structure further includes at least one anti-coagulant.
107. The device of paragraph 85, wherein the absorbent structure further includes at least one of an acid, a base, or a buffer.
108. The device of paragraph 85, wherein the absorbent structure further includes at least one lateral flow assay.
109. The device of paragraph 108, wherein the at least one lateral flow assay includes at least one of an immunological assay, enzymatic assay, chemical assay, or DNA amplification assay.

110. The device of paragraph 108, wherein the at least one lateral flow assay includes at least one of a colorimetric readout, an electrochemical readout, a fluorescent readout, a chemiluminescent readout, or an electrochemiluminescent readout.

111. The device of paragraph 85, further including a second absorbent structure, the second absorbent structure including a first end and a second end, the first end of the second absorbent structure adjacent to the second end of the absorbent structure and configured to convey the polar liquid from the second end of the absorbent structure to the first end of the second absorbent and through to the second end of the second absorbent structure and into the tapered internal chamber.

112. The device of paragraph 111, wherein the second absorbent structure includes at least one dry dye for a liquid.

113. The device of paragraph 85, wherein the support structure is rigid.

114. The device of paragraph 85, wherein at least a portion of the support structure is optically transparent and suitable for microscopy.

115. The device of paragraph 85, wherein the support structure is fabricated from glass.

116. The device of paragraph 85, wherein the support structure is fabricated from plastic.

117. The device of paragraph 85, wherein the first end of the support structure includes a first end region positioned adjacent to the first end of the absorbent structure.

118. The device of paragraph 117, wherein the first end region of the support structure includes a sample reservoir.

119. The device of paragraph 118, wherein the sample reservoir is formed from one or more wall structures extending outward from a surface of the first end region of the support structure.

120. The device of paragraph 117, wherein the first end region of the support structure includes one or more capillary channels in fluid communication with the first end of the absorbent structure.

121. The device of paragraph 85, wherein the lid structure is semi-rigid.

122. The device of paragraph 85, wherein at least a portion of the lid structure is optically transparent and suitable for microscopy.

123. The device of paragraph 85, wherein the lid structure is fabricated from glass.

124. The device of paragraph 85, wherein the lid structure is fabricated from plastic.

125. The device of paragraph 85, wherein the first end of the lid structure includes a first end region, the first end region positioned adjacent to the first end of the absorbent structure.

126. The device of paragraph 125, wherein the first end region of the lid structure includes a sample access region.

127. The device of paragraph 126, wherein at least a portion of the sample access region includes the first end of the absorbent structure.

128. The device of paragraph 85, wherein the clamping structure includes one or more binding bars.

129. The device of paragraph 85, wherein the clamping structure includes a structure wrapping around three sides of the support structure and the lid structure and leaving the first end of the absorbent structure accessible.

130. The device of paragraph 85, wherein the clamping structure includes at least one of an adhesive, glue, or heat seal.

131. The device of paragraph 85, wherein the tapered internal chamber includes a decreasing distance between the internal surface of the second end region of the support structure and the internal surface of the second end region of the lid structure.

132. The device of paragraph 131, wherein a maximum distance between the internal surface of the second end region of the support structure and the internal surface of the second end region of the lid structure forming the tapered internal chamber is defined by a thickness of the second end of the absorbent structure positioned adjacent to the tapered internal chamber.

133. The device of paragraph 131, wherein the minimum distance between the internal surface of the second end region of the support structure and the internal surface of the second end region of the lid structure is defined by a distance between the internal surface of the second end region of the support structure and the internal surface of the second end region of the lid structure when the clamping structure is in position.

134. The device of paragraph 131, wherein the decreasing distance between the internal surface of the second end region of the support structure and the internal surface of the second end region of the lid structure defines a microscopy viewing region of decreasing depth.

135. The device of paragraph 85, wherein the tapered internal chamber forms a decreasing gradient volume of the polar liquid.

136. The device of paragraph 85, wherein one or more outer edges of the tapered internal chamber away from the absorbent structure are at least partially unsealed.

137. The device of paragraph 85, wherein the interior hydrophobic region includes at least one of silane, polydimethylsiloxane, wax, polystyrene, or alkyl ketene dimer.

138. The device of paragraph 85, wherein the interior hydrophobic region is printed onto the absorbent structure.

139. The device of paragraph 85, wherein the interior hydrophobic region is part of an air outflow region.

140. The device of paragraph 85, wherein the interior hydrophobic region is positioned adjacent to and parallel with the interior hydrophilic region of the absorbent structure, a first end of the interior hydrophobic region extending beyond the first end of the lid structure and open to a position adjacent to the device and a second end of the interior hydrophobic region positioned adjacent to the tapered internal chamber.

141. The device of paragraph 85, wherein the interior hydrophobic region includes a separate structure positioned adjacent to at least a portion of the absorbent structure and in a flow path of the polar liquid.

142. The device of paragraph 85, wherein the tapered internal chamber further includes an outflow region.

143. The device of paragraph 142, wherein the outflow region of the tapered internal chamber includes a hydrophobic region.

144. The device of paragraph 143, wherein the hydrophobic region is positioned at one or more outer edges of the tapered internal chamber.

145. The device of paragraph 143, wherein the hydrophobic region forms a hydrophobic barrier positioned along at least one outer edge of the tapered internal chamber.

146. The device of paragraph 143, wherein the hydrophobic region defines a flow channel.

147. The device of paragraph 143, wherein the hydrophobic region includes a phase guide to convey air out to the tapered internal chamber.
148. The device of paragraph 143, wherein the hydrophobic region includes a pattern of hydrophobic material on at least a portion of the internal surface of the second end region of the support structure or the internal surface of the second end region of the lid structure forming the tapered internal chamber.
149. The device of paragraph 148, wherein the pattern of hydrophobic material includes one or more lines of hydrophobic material positioned parallel to flow of the polar liquid into the tapered internal chamber.
150. The device of paragraph 148, wherein the pattern of hydrophobic material includes one or more lines of hydrophobic material positioned perpendicular to flow of the polar liquid into the tapered internal chamber.
151. The device of paragraph 85, wherein combination of the absorbent structure, the support structure, and the lid structure are sized for use with a microscope.
152. The device of paragraph 85, further including a housing formed from the support structure and the lid structure, the housing enclosing the absorbent structure and the tapered internal chamber.
153. In some embodiments, a method of preparing a liquid sample includes: receiving the liquid sample at a first end of a microfluidic microscopy device, the microfluidic microscopy device including an absorbent structure with a first end and a second end, the absorbent structure including an interior hydrophilic region with at least one dry dye for a liquid; a support structure positioned adjacent to a first surface of the absorbent structure, the support structure including a first end and a second end, the second end of the support structure including a second end region positioned adjacent to the second end of the absorbent structure; a lid structure positioned adjacent to a second surface of the absorbent structure, the lid structure including a first end and a second end, the second end of the lid structure projecting beyond the second end of the absorbent structure, the second end of the lid structure including a second end region positioned adjacent to the second end of the absorbent structure and overlapping with the second end region of the support structure; and a clamping structure positioned to maintain a relative position of the support structure and the lid structure to form a tapered internal chamber, the tapered internal chamber including an internal surface of the second end region of the support structure facing an internal surface of the second end region of the lid structure, the tapered internal chamber including an outflow region; migrating the liquid sample from the first end of the absorbent structure to the second end of the absorbent structure through the interior hydrophilic region including the at least one dry dye for a liquid; dissolving the at least one dry dye for a liquid in the liquid sample while migrating the liquid sample through the interior hydrophilic region; migrating the liquid sample with the dissolved at least one dry dye for a liquid from the second end of the absorbent structure into the tapered internal chamber; and filling the tapered internal chamber with the liquid sample with the dissolved at least one dry dye for a liquid while pushing air out of the tapered internal chamber through the outflow region.
154. The method of paragraph 153, wherein receiving the liquid sample at the first end of the microfluidic microscopy device includes receiving the liquid sample at the first end of the absorbent structure.
155. The method of paragraph 153, wherein receiving the liquid sample at the first end of the microfluidic microscopy device includes receiving the liquid sample into a sample reservoir positioned at the first end of the microfluidic device, the sample reservoir in fluid communication with the first end of the absorbent structure.
156. The method of paragraph 153, wherein receiving the liquid sample at the first end of the microfluidic microscopy device includes receiving a body fluid sample at the first end of the microfluidic microscopy device.
157. The method of paragraph 153, wherein receiving the liquid sample at the first end of the microfluidic microscopy device includes receiving a blood sample at the first end of the microfluidic microscopy device.
158. The method of paragraph 153, wherein migrating the liquid sample from the first end of the absorbent structure to the second end of the absorbent structure includes migrating the liquid sample at a fixed flow rate.
159. The method of paragraph 153, wherein migrating the liquid sample from the first end of the absorbent structure to the second end of the absorbent structure includes migrating the liquid sample at a variable flow rate dictated by one or more properties of the absorbent structure.
160. The method of paragraph 159, wherein migrating the liquid sample at a variable flow rate dictated by one or more properties of the absorbent structure includes migrating the liquid sample at a variable flow rate dictated by a shape of the absorbent structure.
161. The method of paragraph 159, wherein migrating the liquid sample at a variable flow rate dictated by one or more properties of the absorbent structure includes migrating the liquid sample at a variable flow rate dictated by one or more hydrophobic regions incorporated into the absorbent structure.
162. The method of paragraph 153, further including staining one or more cellular components of the liquid sample with the at least one dry dye for a liquid while migrating the liquid sample from the first end of the absorbent structure through the interior hydrophilic region to the second end region of the absorbent structure.
163. The method of paragraph 153, further comprising migrating the liquid sample from a first region of the absorbent structure including at least one first dry dye for a liquid to a second region of the absorbent structure including at least one second dry dye for a liquid.
164. The method of paragraph 153, further including removing at least a portion of the dissolved at least one dry dye for a liquid by migrating the liquid sample through a portion of the absorbent structure configured to retain the at least a portion of the dissolved at least one dry dye for a liquid.
165. The method of paragraph 153, wherein migrating the liquid sample with the dissolved at least one dry dye for a liquid from the second end of the absorbent structure into the tapered internal chamber includes migrating the liquid sample with the dissolved at least one dry dye for a liquid from the second end of the absorbent structure into the tapered internal chamber from a single point.
166. The method of paragraph 153, wherein migrating the liquid sample with the dissolved at least one dry dye for a liquid from the second end of the absorbent structure into the tapered internal chamber includes migrating the liquid sample with the dissolved at least one dry dye for a liquid from the second end of the absorbent structure into the tapered internal chamber from two or more points.

167. The method of paragraph 153, wherein pushing the air out of the tapered internal chamber through the outflow region includes pushing the air out of the tapered internal chamber through a hydrophobic region positioned at one or more outer edges of the tapered internal chamber.

168. The method of paragraph 153, wherein pushing the air out of the tapered internal chamber through the outflow region includes pushing the air out of the tapered internal chamber through a hydrophobic region patterned on at least one of the internal surface of the second end region of the support structure or the internal surface of the second end region of the lid structure.

169. The method of paragraph 153, wherein pushing the air out of the tapered internal chamber through the outflow region includes pushing the air out of the tapered internal chamber back through an interior hydrophobic region incorporated into the absorbent structure.

170. In some embodiments, a method of analyzing a liquid sample includes providing an optical detector; and using the optical detector to measure an optical property of a liquid sample in a tapered internal chamber of a microfluidic microscopy device, the microfluidic microscopy device including an absorbent structure with a first end and a second end, the absorbent structure including an interior hydrophilic region with at least one dry dye for a liquid, the absorbent structure configured to convey the liquid sample from the first end of the absorbent structure through the interior hydrophilic region and the at least one dry dye for a liquid to the second end of the absorbent structure; a support structure positioned adjacent to a first surface of the absorbent structure, the support structure including a first end and a second end, the second end of the support structure including a second end region positioned adjacent to the second end of the absorbent structure; a lid structure positioned adjacent to a second surface of the absorbent structure, the lid structure including a first end and a second end, the second end of the lid structure projecting beyond the second end of the absorbent structure, the second end of the lid structure including a second end region positioned adjacent to the second end of the absorbent structure and overlapping with the second end region of the support structure; and a clamping structure positioned to maintain a relative position of the support structure and the lid structure to form a tapered internal chamber, the tapered internal chamber including an internal surface of the second end region of the support structure facing an internal surface of the second end region of the lid structure, the tapered internal chamber including an outflow region.

171. The method of paragraph 170, wherein providing an optical detector includes providing a microscope.

172. The method of paragraph 170, wherein providing an optical detector includes providing a spectrophotometer.

173. The method of paragraph 170, wherein using the optical detector to measure the optical property of the liquid sample in the tapered internal chamber of the microfluidic microscopy device includes using the optical detector to measure a fluorescence intensity of the liquid sample in the tapered internal chamber.

174. The method of paragraph 170, wherein using the optical detector to measure the optical property of the liquid sample in the tapered internal chamber of the microfluidic microscopy device includes using the optical detector to measure a color intensity of the liquid sample in the tapered internal chamber.

175. The method of paragraph 170, wherein using the optical detector to measure the optical property of the liquid sample in the tapered internal chamber of the microfluidic microscopy device includes using the optical detector to measure an optical property associated with one or more cellular components in the liquid sample in the tapered internal chamber.

176. The method of paragraph 170, wherein using the optical detector to measure the optical property of the liquid sample in the tapered internal chamber of the microfluidic microscopy device includes using the optical detector to measure the optical property of the liquid sample at two or more points along a microscopy viewing region of decreasing depth of the tapered internal chamber.

177. The method of paragraph 170, wherein using the optical detector to measure the optical property of the liquid sample in the tapered internal chamber of the microfluidic microscopy device includes using the optical detector to count on to more cell types in the liquid sample in the tapered internal chamber.

178. The method of paragraph 170, further including calculating a volume calibration by using the optical detector by using the optical detector to measure the optical property of the liquid sample in the tapered internal chamber.

179. The method of paragraph 170, further including generating a diagnosis regarding a medical condition by using the optical detector to measure the optical property of the liquid sample in the tapered internal chamber.

One skilled in the art will recognize that the herein described components, devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A microfluidic microscopy device comprising:
an absorbent structure with a first end and a second end, the absorbent structure including an interior hydrophilic region;
a support structure positioned adjacent to a first surface of the absorbent structure, the support structure including a first end and a second end, the second end of the support structure including a second end region positioned extending beyond the second end of the absorbent structure;
a lid structure positioned adjacent to a second surface of the absorbent structure, the lid structure including a first end and a second end, the second end of the lid structure extending beyond the second end of the absorbent structure, the second end of the lid structure including a second end region positioned extending beyond the second end of the absorbent structure and overlapping with the second end region of the support structure; and
a clamping structure positioned to maintain a relative position of the support structure and the lid structure to form a tapered internal chamber extending beyond the second end of the absorbent structure, the tapered internal chamber including an internal surface of the second end region of the support structure facing an internal surface of the second end region of the lid structure, the tapered internal chamber including an outflow region;
wherein the absorbent structure is configured to convey a polar liquid from the first end of the absorbent structure through the interior hydrophilic region to the second end of the absorbent structure and into the tapered internal chamber.

2. The device of claim 1, wherein the second end of the absorbent structure comprises a non-linear edge.

3. The device of claim 1, wherein the absorbent structure further comprises at least one lateral flow assay.

4. The device of claim 1, wherein the absorbent structure further comprises an interior hydrophobic region as part of an air outflow region.

5. The device of claim 1, further comprising:
a second absorbent structure, the second absorbent structure including a first end and a second end, the first end of the second absorbent structure adjacent to the second end of the absorbent structure and configured to convey the polar fluid from the second end of the absorbent structure to the first end of the second absorbent structure and through to the second end of the second absorbent structure and into the tapered internal chamber.

6. The device of claim 1, wherein at least a portion of the support structure is optically transparent and suitable for microscopy.

7. The device of claim 1, wherein the first end of the support structure comprises a first end region positioned adjacent to the first end of the absorbent structure, the first end region of the support structure including a sample reservoir.

8. The device of claim 7, wherein the first end region of the support structure comprises one or more capillary channels in fluid communication with the first end of the absorbent structure.

9. The device of claim 1, wherein the lid structure is semi-rigid.

10. The device of claim 1, wherein at least a portion of the lid structure is optically transparent and suitable for microscopy.

11. The device of claim 1, wherein the first end of the lid structure comprises a first end region, the first end region of the lid structure positioned adjacent to the first end of the absorbent structure and including a sample access region.

12. The device of claim 1, wherein the tapered internal chamber comprises a decreasing distance between the internal surface of the second end region of the support structure and the internal surface of the second end region of the lid structure, the decreasing distance between the internal surface of the second end region of the support structure and the internal surface of the second end region of the lid structure defining a microscopy viewing region of decreasing depth.

13. The device of claim 1, wherein the outflow region of the tapered internal chamber comprises a hydrophobic region.

14. The device of claim 1, wherein at least a portion the internal surface of the second end region of the support structure or the internal surface of the second end region of the lid structure forming the tapered internal chamber comprises a hydrophobic region, the hydrophobic region including a pattern of hydrophobic material.

15. The device of claim 1, wherein the tapered internal chamber forms a decreasing gradient volume of the polar liquid.

16. The device of claim 1, wherein one or more outer edges of the tapered internal chamber away from the absorbent structure are at least partially unsealed.

* * * * *

UNITED STATES PATENT AND TRADEMARK OFFICE
CERTIFICATE OF CORRECTION

PATENT NO. : 9,453,996 B2
APPLICATION NO. : 14/061009
DATED : September 27, 2016
INVENTOR(S) : Charles Delahunt et al.

Page 1 of 1

It is certified that error appears in the above-identified patent and that said Letters Patent is hereby corrected as shown below:

In the Claims

Column 58, line 10, claim 14 - "wherein at least a portion the" should read --wherein at least a portion of the--

Signed and Sealed this
Twentieth Day of December, 2016

Michelle K. Lee
*Director of the United States Patent and Trademark Office*